United States Patent [19]

Schwartz et al.

[11] Patent Number: 5,001,119
[45] Date of Patent: Mar. 19, 1991

[54] 16-SUBSTITUTED ANDROSTANES AND 16-SUBSTITUTED ANDROSTENES

[76] Inventors: Arthur G. Schwartz, 220 Locust St., Philadelphia, Pa. 19106; Marvin L. Lewbart, 546 E. Saint Andrews Dr., Media, Pa. 19063

[21] Appl. No.: 126,215

[22] Filed: Nov. 25, 1987

[51] Int. Cl.$^5$ .......................... A61K 31/56; C07J 9/00
[52] U.S. Cl. .................................. 514/177; 514/178; 514/885; 514/886; 514/887; 514/888; 514/889; 514/894; 514/896; 514/897; 514/903; 514/908; 514/934; 552/508; 552/528; 552/539; 552/650; 552/651; 540/41; 540/45; 540/46
[58] Field of Search ................. 514/177, 178, 885, 86, 514/887, 888, 889, 894, 896, 897, 903, 908, 934; 260/397.3, 397.4, 397.45; 540/41, 45, 46

[56] References Cited

U.S. PATENT DOCUMENTS 3,391,166 7/1968 Klimstra .
3,471,480 10/1969 Fritsch et al. .
3,471,526 10/1969 Klimstra et al. .
3,976,691 8/1976 Middleton et al. .
4,628,052 12/1986 Peat et al. .

FOREIGN PATENT DOCUMENTS 0133995 3/1985 European Pat. Off. .
210665 2/1987 European Pat. Off. .
1239306 4/1964 Fed. Rep. of Germany .
2035738 6/1970 Fed. Rep. of Germany .
2705917 2/1977 Fed. Rep. of Germany .
2317934 2/1977 France .
989503 8/1963 United Kingdom .

OTHER PUBLICATIONS

Hydroxy Steroids Part XVII The 5α-Androstane-16,-17-diols and Related Compounds Combe et al. J. Chem. Soc. (©(1971) 2300-2304.
Hydroxy Steroids Part XVIII Reactions of 17β-–Chloro-16α,17α-Epoxy-5α-Androstane and the Preparation of 17β-Iodo-16α,17αEpoxy-5α Androstane J. Chem Soc (PKI) (1972) 486-491.
Hanson, et al., *Perkin Transactions I*, (1977), pp. 499-501.
Chemical Abstracts, 89, 1058656, (1978).
Numazawa, et al. *Steroids*, 32, 519-527 (1978).
Abou-Gharbia, et al., *Journal of Pharmaceutical Sciences*, 70, 1154-1157 (1981).
Pashko, et al., *Carcinogenesis*, 2, 717-721 (1981).
Raineri and Levy, *Biochemistry*, 9, 2233-2243 (1970).
Robinson, et al., *J. Org. Chem.* 28, 975 (1963).
Neef, et al., *J. of Org. Chem.*, 43, 4679-4680 (1978).
Gordon, et al. *Cancer Research* 46, 3389-3395 (1986).

Julian, et al. in *JACS*, 70, 3872-3876 (1948).
Ross, et al. in *J. Chem. Soc.*, 25-27 (1945).
Crabb, et al. in *J.C.S. Parkin I*, 1041-1045 (1981).
Chemical Abstracts 92, 215616v (1980).
Bird, et al. in *J.C.S. Perkin I*, 750-755 (1980).
Kirk, et al., in *J.C.S. Perkin I*, 762-779 (1976).
Chemical Abstracts, 79, 42729 (1973).
Denny, et al., in *J.C.S. Perkin I*, 486-492 (1972).
Bridgeman, et al. in *J. Chem. Soc. C*, 250 (1970).
Mailloux, et al. in *Bulletin de la Societe Chimique de France*, 617-621 (1969).
Chemical Abstracts, 67, 54331k (1967).
Catsoulacos, et al. in *J. Org. Chem.*, 32, 3723-3724 (1967).
Sheppard, et al. in *Some Chemistry of 13-Iso—steriods*, 2551-2558 (1977).
Pelc, et al. in *Collection Czechoslov. Chem. Commun.* 31, 1064-1071 (1966).
Klimstra, et al., in *Journal of Med. Chem.*, 9, 924-929 (1966).

*Primary Examiner*—Asok Pal
*Assistant Examiner*—James Saba
*Attorney, Agent, or Firm*—Scully, Scott, Murphy & Presser

[57] ABSTRACT

Compounds of the formula:

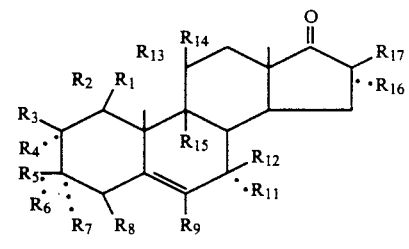

and

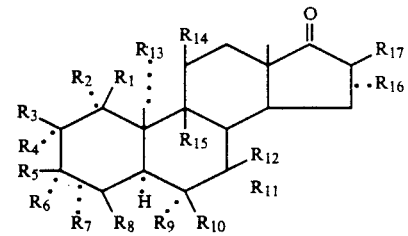

are useful as anti-cancer, anti-obesity, anti-diabetic, anti-coronary agents, anti-aging agents, anti-hypolipidemic agents and anti-autoimmune agents.

100 Claims, No Drawings

16-SUBSTITUTED ANDROSTANES AND 16-SUBSTITUTED ANDROSTENES

BACKGROUND OF THE INVENTION

This invention relates to novel steroids and more particularly to androsterone derivatives useful as anti-cancer, anti-obesity, anti-diabetic, and hypolipidemic agents and useful in combatting coronary diseases.

Dehydroepiandrosterone (DHEA) and DHEA-sulfate are major adrenal secretory products in humans. The plasma concentration of DHEA-sulfate, which next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease," Eur. J. Cancer, 8, 131–137 (1972); Bulbrook, et al., "Relation between urinary androgen and corticoid excretion and subsequent breast cancer," Lancet, 2, 395–398 (1971); Rose, et al., "Plasma dehydroepiandrosterone sulfate, androstenedione and cortisol, and urinary free cortisol excretion in breast cancer," Eur. J. Cancer, 13, 43–47 (1977); Wang, et al., "Studies of the sulfate esters of dehydroepiandorsterone and androsterone in the blood of women with breast cancer," Eur. J. Cancer, 10, 477–482 (1974); and Zumoff, et al., "Abnormal 24-hr mean plasma concentrations of dehydroisoandrosterone and dehydroisoandrosterone sulfate in women with primary operable breast cancer," Cancer Research, 41, 3360–3363, Sept., 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493–496 (1972) and Marks, et al., "Inhibition of mammalian glucose-6-phosphate dehydrogenase by steroids," Proc. Nat'l Acad. Sci, U.S.A., 46, 477–452 (1960). Moreover, Yen, et al., "Prevention of obesity in A$^{vy}$/a mice by dehydroepiandrosterone," Lipids, 12, 409–413 (1977), reported that long-term administration of DHEA to VY-A$^{vy}$/a mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-0-tetradecanoylphorbol-13-acetate, to stimulate $^3$H-thymidine incorporation in mouse epidermis and in a cultured rat kidney epithelial cell line. See, Schwartz, "Inhibition of spontaneous breast cancer formation in female C3H-A$^{vy}$/a mice by long-term treatment with dehydroepiandrosterone, Cancer Res., 39, 1129–1132 (1979); and Schwartz, et al., "Dehydroepiandrosterone: an anti-obesity and anti-carcinogenic agent," Nut. Cancer 3, 46–53 (1981).

Ben-David, et al., "Anti-hypercholesterolemic effect of dehydroepiandrosterone in rats," Proc. Soc. Expt. Biol. Med., 125, 1136–1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16α-bromoepiandrosterone are inhibitors of Epstein-Barr virus-induced transformation of human lymphocytes and that 16α-bromoepiandrosterone is a more potent inhibitor of mammalian G6PDH than DHEA. See, Schwartz, et al. Carcinogensis, Vol. 2 No. 7, 683–686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

Besides DHEA, other steroids are known in the art.

Great Britain Patent No. 989,503 to Burn, et al. discloses 6,16β-dimethyl-3β-hydroxyandrost-5-en-17-ones. These compounds are disclosed to be useful as possessing pituitary inhibiting action.

U.S. Pat. No. 2,833,793 to Dodson, et al. discloses 1β,3β-dihydroxy-5-androsten-17-one as an androgenic and anabolic agent.

U.S. Pat. No. 2,911,418 to Johns, et al. discloses 16α-chloro-3β-hydroxyandrost-5-en-17-one and 3β-hydroxy-16α-iodoandrost-5-en-17-one as an anti-androgen.

Goldkamp, et al. in U.S. Pat. No. 3,148,198 disclose that 16α,16β-difluoro-3β-hydroxyandrost-5-en-17-one possess androgenic properties.

French Application No. FR-A 2,317,934 discloses the following compounds:

3β-hydroxy-16ξ-methylandrost-5-en-17-one
3β-hydroxy-16ξ-ethylandrost-5-en-17-one
3β-hydroxy-16ξ-isopropylandrost-5-en-17-one U.S. Pat. No. 3,976,691 discloses the following compounds:

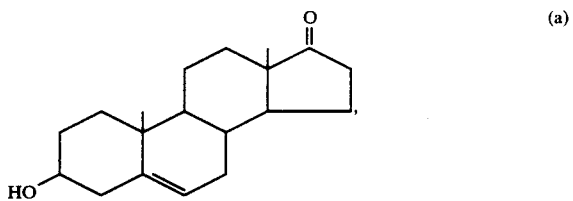

(a)

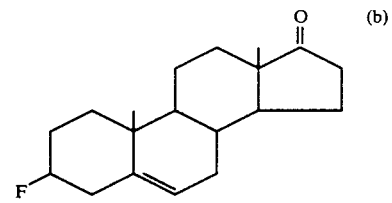

(b)

U.S. Pat. No. 3,471,480 to Fritsch, et al. discloses the following compounds which are useful as progestational agents:

(a) 3β-iodo-Δ⁵-6-methyl-17-oxoandrostene
(b) 3β-chloro-Δ⁵-6-methyl-17-oxoandrostene
(c) 3β-hydroxy-Δ⁵-6-methyl-17-oxoandrostene Hanson, et al. in Perkin Transactions I, 1977, pp. 499–501, disclose 3β,4β-dihydroxyandrost-5-en-17-one. No utility is disclosed.

Chemical Abstract 89:105866b discloses that 3β-hydroxy-5α-androstan-17-one can be hydroxylated in the 15α-position. Furthermore, said reference teaches that hydroxylation of 3β-hydroxy-5αandrosten-17-one gave both the 7α and 7β-hydroxyisoandrosterones.

Numazawa, et al. in *Steroids*, 32, 519–527 disclose 3β,16α-dihydroxyandrost-5-en-17-one. No utility is disclosed.

DE-A-2,035,738 discloses 7α-Methyl-3β-hydroxy-5-androsten-17-one and 6,7α-dimethyl-3β-hydroxy-5-androsten-17-one.

DE-A No. 2 705917 discloses 3β,16β-dihydroxy-5-androsten-17-one.

The Annual Report of the Fels Research Institute, pp. 32–33, (1979–1980) discloses the following compounds as having tumor-preventive, anti-obesity and anti-aging qualities:

3β-hydroxy-16α-bromo-5α-androstan-17-one
3β-hydroxy-16α-chloro-5α-androstan-17-one
3β-hydroxy-16α-fluoro-5α-androstan-17-one
3β-hydroxy-16α-iodo-5α-androstan-17-one
3β-hydroxy-16α-bromoandrost-5-ene-17-one
16αbromoandrostan-17-one Abou-Gharbia, et al. in *Journal of Pharmaceutical Sciences*, 70, 1154–1156 (1981) disclose the syntheses of:
3β-hydroxy-16α-chloro-5α-androstan-17-one,
3β-hydroxy-16α-fluoro-5α-androstan-17-one,
3β-hydroxy-16α-bromo-5α-androstan-17-one,
3β-hydroxy-16α-iodo-5α-androstan-17-one.

Pashko, et al. in *Carcinogenesis*, 2, 717–721 (1981) disclose that 16α-Br-epiandrosterone is more active than DHEA in inhibiting G6PDH and in reducing the rate of [³H] thymidine incorporation into mouse breast epithilum and epidermis. The authors suggest that this compound may be useful in suppressing breast cancer development.

Neef, et al. in *Journal of Org. Chem.*, 43, 4679–4680 disclose the syntheses of 3β-hydroxy-16α-methyl-5-androsten-17-one and 3β-hydroxy-16β-methyl-5-androsten-17-one.

Robinson, et al. in *Journal of Org. Chem.*, 28, 975–980 (1963) disclose the synthesis of 3β-hydroxy-16α,16β-difluoro-5-androsten-17-one, and 16-formyl-5-androstene-3βol-17-one.

Raineri, et al. in *Biochemistry*, 9, 2233–2243 (1970) tested the inhibitory activity of the following steroids on NADP and NAD linked activity of glucose 6-phosphate dehydrogenase:

3β-hydroxy-5α-androstan-17-one
3β-hydroxy-5β-androstan-17-one
3α-hydroxy-5α-androstan-17-one
11β-hydroxy-5α-androstan-17-one
3α-hydroxy-4α-methyl-5αandrostan-17-one
3α-hydroxy-7α-methyl-5αandrostan-17-one
3β-hydroxy-7α-methyl-5βandrostan-17-one
3β-hydroxy-16α-bromo-5αandrostan-17-one
3β-chloro-5α-androstan-17-one.

Gordon, et al. in Cancer Research 46, 3389–3395 (1986) disclose that DHEA, 16α-bromoepiandrosterone, epiandrosterone, 3β-hydroxy-5α-pregnan-20-one, 5α-androstan-17-one and 5α-androstan-3β,16α-diol-17-one are inhibitors of glucose 6-phosphate dehydrogenase. Furthermore, said reference discloses that testosterone, 17β-Estradiol, 5-androstene-3β,17βdiol, dehydroepiandrosterone-3-sulfate and 5α-androstan-17β-ol are noninhibitors of glucose-6-phosphate dehydrogenase. The reference suggests that there is a general correlation between the structure requirements for blocking differentiation to adipocytes and inhibiting glucose-6-phosphate dehydrogenase.

Julian, et al. in JACS, 70, 3872–3876 (1948) discloses the preparation of 16-dimethylaminomethyldehydroisoandrosterone and 16-methylenedehydroisoandrosterone acetate.

Ross, et al. in J. Chem. Soc., 25, (1945) disclose the synthesis of 16-isopropylidene-5-androstene-17-one.

Peat in U.S. Pat. No. 4,028,052 discloses compositions containing the following compounds as the active ingredient:

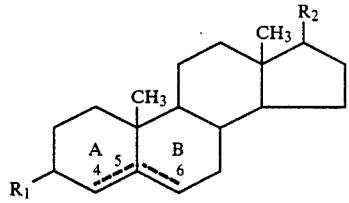

wherein R₁ is O or OH and R₂ is O, or OH; and which may contain one double bond in ring A and/or ring B or tocopherol.

The compounds are alleged to be useful in treating rhemumatoid arthritis, osteoarthritis and arthritas associated with psoriases and with lupus and other autoimmune diseases and also for treating non-specific joint pain associated with stress.

SUMMARY OF THE INVENTION

The present invention relates to novel steroids which are useful as cancer-preventive agents, anti-obesity agents, anti-hyperglycemic agents, anti-aging agents, anti-hypercholesterolemic agents and anti-autoimmune agents.

Moreover, the present invention is directed to novel steroids, useful as anti-cancer, anti-obesity, anti-hyperglycemic, anti-aging and anti-hypercholesterolemic agents, which do not evidence estrogenic effects.

Finally, the present invention is directed to the process for the treatment and/or prevention of cancer, obesity, aging, diabetes and hyperlipidemia.

Therefore, the present invention provides novel steroids of the general formula:

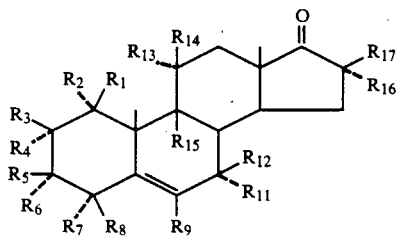

wherein $R_1$, $R_2$, $R_3$, $R_4$, $R_5$, $R_6$, $R_7$, $R_8$, $R_{11}$, $R_{12}$, $R_{13}$, $R_{14}$ and $R_{15}$ are independently hydrogen, lower alkyl, halogen, hydroxy or lower alkoxy;

$R_9$ is hydrogen, lower alkyl or halogen; and $R_{16}$ and $R_{17}$ are independently hydrogen, amino, loweralkylamino, diloweralkylamino, aminoloweralkyl, loweralkyl aminolower alkyl, diloweralkylaminolower alkyl, loweralkoxyloweralkyl, lower alkoxy, hydroxy lower alkyl, monohaloloweralkyl, dihaloloweralkyl, trihaloloweralkyl, loweralkanoyl, formyl, lower carbalkoxy, or lower alkanoyloxy or $R_{16}$ and $R_{17}$ taken together with the carbons to which they are attached form a lower cycloalkyl or a cyclic ether containing one ring oxygen atom and up to 5 ring carbon atoms with the proviso that when $R_5$ is hydroxy and $R_1$, $R_2$, $R_3$, $R_4$, $R_6$, $R_7$, $R_8$, $R_9$, $R_{11}$, $R_{12}$, $R_{13}$, $R_{14}$ and $R_{15}$ are hydrogen, then $R_{16}$ is other than $CH_2N(CH_3)$ and with the further proviso that $R_{16}$ and $R_{17}$ are not hydrogen simultaneously.

Further objectives are accomplished herein by providing novel steroids of the formula:

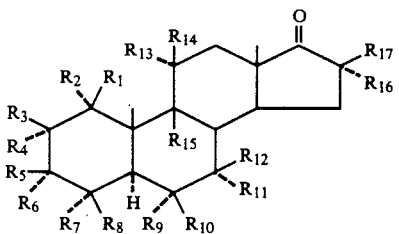

wherein $R_1$, $R_2$, $R_3$, $R_4$, $R_5$, $R_6$, $R_7$, $R_8$, $R_{11}$, $R_{12}$, $R_{13}$, $R_{14}$ and $R_{15}$ are independently hydrogen, lower alkyl, halogen, hydroxy or lower alkoxy;

$R_9$ and $R_{10}$ are independently loweralkyl, hydrogen or halogen; and $R_{16}$ and $R_{17}$ are independently amino, lower alkylamino, diloweralkyl amino, aminoloweralkyl, loweralkyl aminoloweralkyl, diloweralkylamino loweralkyl, lower alkoxy, hydroxyloweralkyl, monohaloloweralkyl, loweralkoxyloweralkyl, loweralkanoyl, formyl, lower carbalkoxy, hydrogen or lower alkanoyloxy; or $R_{16}$ and $R_{17}$ taken together with the carbon to which they are attached form a lower cycloalkyl or a cyclic ether containing one ring oxygen atom and up to 5 ring carbon atoms, with the further proviso that $R_{16}$ and $R_{17}$ are not hydrogen simultaneously.

The present invention is also directed to processes for the prophylaxis and/or treatment of cancer, obesity, aging, diabetes and hyperlipidemia and autoimmune diseases, such as lupus erthematosus or Coomb's positive hemolytic anemia, comprising administering to a host, e.g., mammals, a therapeutically effective amount of the aforeidentified steroids.

More particularly, the steroids of the present invention have the general formulae:

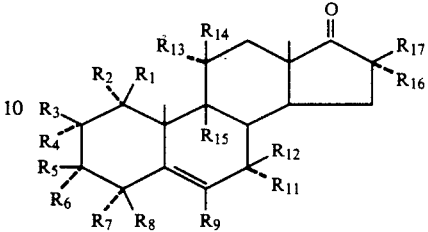

and

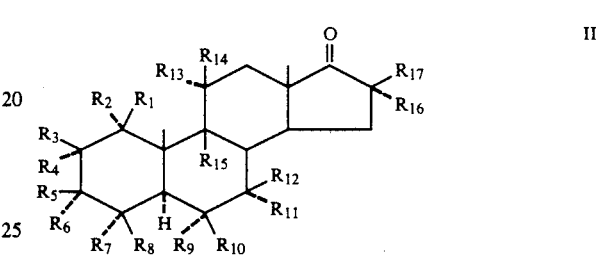

wherein $R_1$–$R_{16}$ are as defined hereinbefore. The $R_1$–$R_{16}$ substituents are designated as being in the α-position by means of a broken line (-----) joining the substituent to the steroid nucleus, the substituents are designated as being in the β-position by means of a solid line (———) joining the substituent to the steroid nucleus and in those cases in which the substituent may be either in the α- or β-position the substituents are indicated as being joined to the steroid nucleus by a wavy line. Furthermore, in accordance with I.U.P.A.C. nomenclature, the carbon atoms of the steroids of the present invention are numbered as follows and the steroids have the designated I.U.P.A.C. stereochemistry:

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging, anti-autoimmune and anti-hypercholesterolemic agents, but unlike DHEA are more potent and exhibit very little or no estrogenic effect. Furthermore, unlike DHEA, compounds of the present invention do not induce liver enlargement and increased catalase activity.

In the present invention, the alkyl groups are preferably lower alkyl, which may be straight or branched chain, and which contain up to 6 carbon atoms. Examples include methyl, ethyl, propyl, isopropyl, butyl, isobutyl, pentyl, amyl and the like. A preferred alkyl group contains 1–3 carbons. The most preferred alkyl group is methyl.

The alkoxy groups are preferably lower alkoxy, which may be straight or branched chain and which contain up to 6 carbon atoms. Examples include methoxy, ethoxy, propoxy, isopropoxy, butoxy, isobutoxy, pentoxy and the like. An especially preferred alkoxy group contains 1–3 carbons. The most preferred alkoxy group is methoxy.

The halo atoms are preferably Br, F or Cl, especially F.

Moreover, it is preferred that at most one of the substituents, $R_1$, $R_2$, $R_3$, $R_4$, $R_7$, $R_8$ $R_9$, $R_{11}$, $R_{12}$, $R_{13}$, $R_{14}$, $R_{15}$ or $R_{10}$, whenever present, are hydrogen. In the most preferred embodiment $R_1$, $R_2$, $R_3$, $R_4$, $R_7$, $R_8$, $R_9$, $R_{11}$, $R_{12}$, $R_{13}$, $R_{14}$, $R_{15}$ and $R_{10}$, whenever present, are hydrogen.

The cycloalkyl groups are saturated cyclic hydrocarbons containg 3–10 ring carbon atoms and containing up to a total of 16 carbon atoms. The cyclic compounds may themselves be mono or disubstituted with alkyl, halogen, hydroxy, lower alkoxy, amino, loweralkylamino, diloweralkylamino, aminoloweralkyl, loweralkyl, lower alkoxy lower alkyl, lower alkoxy, hydroxyloweralkyl, monohaloloweralkyl, dihaloloweralkyl, trihaloloweralkyl, loweralkanoyl, formyl, lower carbalkoxy or lower alkanoyloxy. It is preferred that the cycloalkyl groups are lower cycloalkyl groups, that is, contain 3–6 ring carbon atoms and up to a total of 10 carbon atoms. Examples of cycloalkyl groups include cyclopropyl, cyclobutyl, cyclopentyl, cyclohexyl, cycloheptyl, cyclooctyl, decalinyl, norbornyl, and the like.

The cyclic ether derivative contain 1 oxygen ring atom and up to 5 carbon ring atoms. The cyclic compounds may themselves be mono- or disubstituted with alkyl, halogen, hydroxy, lower alkoxy, amino, loweralkylamino, diloweralkylamino, carboxy, lower carbalkoxy, lower alkanoyloxy, lower alkanoyl and the like. Examples include oxycyclopropyl (epoxide or oxirane ring), oxycyclobutyl, tetrahydrofuryl, and tetrahydropyranyl. It is preferred that the cyclic ether is an oxirane ring.

Preferred embodiments of the compounds of Formula I have the formula:

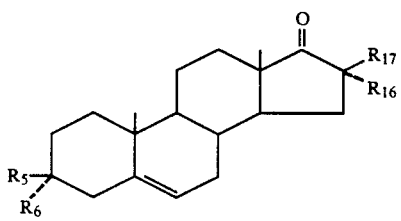

III wherein $R_5$, $R_6$, $R_{16}$ and $R_{17}$ are as defined above. Especially preferred compounds of Formula I have the formula:

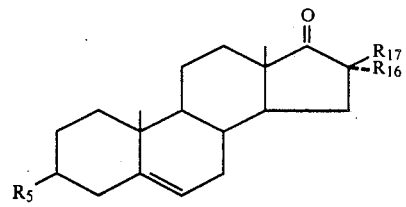

IV wherein $R_5$, $R_{16}$ and $R_{17}$ are as defined above.

Preferred compounds of Formula II have the formula:

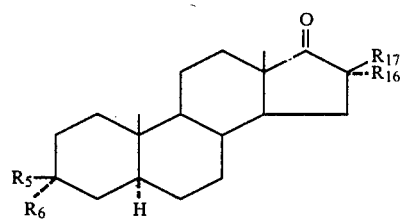

V wherein $R_5$, $R_6$, $R_{16}$ and $R_{17}$ are defined above. Especially preferred compounds of Formula II have the formula:

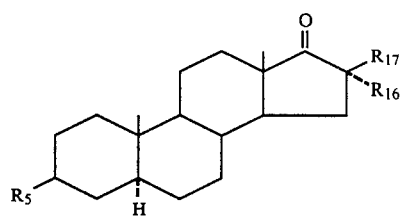

VI wherein $R_5$, $R_{16}$ and $R_{17}$ are as defined above.

In all of the compounds described hereinabove, it is preferred that $R_5$ and $R_6$ are independently hydrogen or lower alkyl. In the most preferred embodiment, $R_5$ is hydrogen or lower alkyl and $R_6$ is hydrogen. The most preferred alkyl group of $R_5$ is methyl.

Preferred substituents of $R_{16}$ and $R_{17}$ include hydrogen, methoxy, trifluoromethyl, difluoromethyl, monofluoromethyl, hydroxymethyl, dimethylaminomethyl or carbomethoxy. Furthermore, when $R_{16}$ and $R_{17}$ taken together to which they are attached form a cycloalkyl group, the most preferred cycloalkyl group is cyclopropyl.

Additional variations in the structural formula representing the instant compounds can be effected without significantly altering the therapeutic properties. For example, the alkyl moieties can be substituted by one or more of a variety of substituents, such as hydroxy, halogen, alkyl and the like.

The procedures described hereinbelow are representative of the processes for preparing compounds of the present invention. For example, even though the procedures are shown for the preparation of compounds wherein $R_{19}$ is $CH_3$, the procedures are also applicable for the preparation of other compounds within the scope of the present invention. Furthermore, the procedures described hereinbelow are also applicable to those steroids which have additional substituents than those depicted hereinbelow. If substituents on the steroidal ring are themselves reactive under the reaction conditions then these substituents can themselves be protected according to chemical techniques known in the art. A variety of protecting groups known in the art may be employed. Examples of many of these possible groups may be found in "Protective Groups in Organic Synthesis," by J. W. Green, John Wiley and Sons, 1981.

If more than one substituent is to be added to the steroidal ring, the substituents can be added in any order, except it is preferred that halogens are added last.

Finally, the procedures described hereinbelow are applicable to all the steroids of the present invention, regardless of whether a double bond is present in the 5,6 position of the steroidal ring. Moreover, those steroids of Formula II can be prepared from the corresponding steroids of Formula I by techniques known to one skilled in the art, e.g., by catalytic hydrogenation using, e.g., $H_2/Pd$, $H_2/Pt$ or $H_2/Ni$.

The steroids of the present invention may be prepared in accordance with conventional organic synthesis from known compounds or readily preparable intermediates.

An exemplary general procedure for the synthesis of the α-alkoxy and alkanoyloxy substituent is as follows:

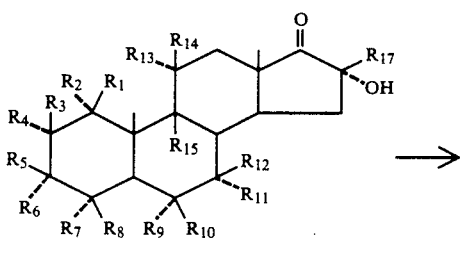

VII

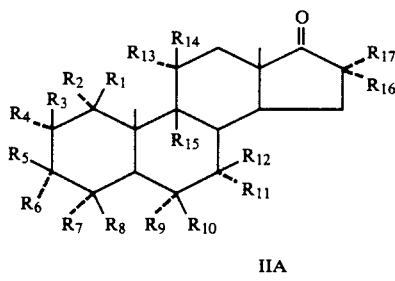

IIA wherein $R_1$–$R_{15}$ and $R_{17}$ are as described hereinabove, and $R_{16}$ in IIA is loweralkoxy or loweralkanoyloxy.

The alkoxy substituent in IIA can be added to the steroid ring by reacting VII under Williamson reaction conditions with RX where X is an organic leaving group such as halide, tosylate or mesylate and R is lower alkyl. Any base normally employed to deprotonate an alcohol may be used such as sodium hydride, sodium amide, sodium, sodium hydroxide, triethylamino or diisopropyl ethylamine. Reaction temperatures are in the range of −78° C. to reflux. The reaction is carried out in a solvent that will dissolve both reactants and is inert to both reactants and products as well. Solvents include, but are not limited to diethyl ether, tetrahydrofuran, N,M-dimethylformamide, methylene chloride, and the like.

The ketone and the hydroxy group, if any, should be protected with protecting groups known in the art. Examples of many of the possible protecting groups that may be utilized are found in "Protective Groups in Organic Synthesis," by T. W. Green. John Wiley and Sons, 1981. For example, the ketone may be protected as the ethylene ketal.

Alternatively, the methoxy substituent is formed by reacting VII in an inert solvent such as methylene chloride with boron trifluoride and etheral diazomethane, according to the procedure of Caserio, et al., JACS, 80, 2584 (1958). Similarly, the ethoxy subsituent is formed by reacting the corresponding alcohol in an inert solvent, such as methylene chloride with boron trifluoride and etheral diazoethane, generated in situ.

The alkanoyloxy substituent is formed by reacting VII with $$\underset{\text{RC—OH}}{\overset{\overset{\displaystyle O}{\parallel}}{}}$$

wherein R is lower alkyl under Fischer esterification conditions, i.e., in the presence of an acid, such as HCl, $H_2SO_4$ or p-toluenesulfonic acid. Alternatively, VII can be reacted with the acid halide $$\underset{\text{RC—X,}}{\overset{\overset{\displaystyle O}{\parallel}}{}}$$

where R is as defined hereinabove and X is halide under esterification conditions. Reaction temperatures are in the range of −78° C. to reflux. The reaction is carried out in a solvent that will dissolve both reactants and is inert to both reactants and products as well. Solvents include, but are not limited to, diethyl ether, tetrahydrofuran, N,N-dimethylformamide, methylene chloride and the like.

Similarly, by interchaging the OH group and $R_{16}$ and using the reaction conditions described hereinabove, the corresponding 16 β-loweralkoxy or alkanoyloxy can be prepared from the corresponding 16 β-hydroxy substituent.

An exemplary procedure for the preparation of 16 α and 16 β carboxy is as follows:

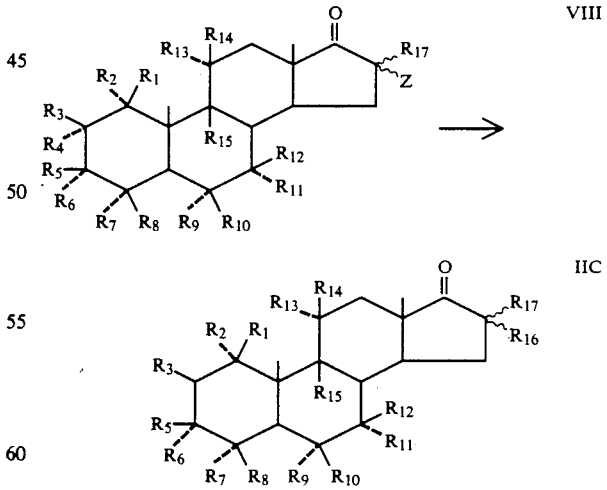

wherein $R_1$–$R_{15}$ are as described above with the proviso that none are halo, $R_{16}$ is carboxy or carbalkoxy, $R_{17}$ is amino, lower alkylamino, diloweralkyl amino, aminoloweralkyl, loweralkyl aminoloweralkyl, diloweralkylamino loweralkyl, lower alkoxy, hydroxyloweralkyl, monohaloloweralkyl, loweralkoxy-loweralkyl, loweralkanoyl, formyl, lower carbalkoxy or lower alkanoyloxy and Z is a good leaving group such as halide, chloride or bromide, mesylate or tosylate.

The carboxy substituent in IIC can be added to the ring by reacting VIII with a cyanide ion, such as NaCN, followed by acid or base hydrolysis of the resulting cyanide, using such reagents as concentrated hydrochloric acid or sulfuric acid or aqueous NaOH containing about 6 to 12% $H_2O_2$. The reaction temperatures for both of these reactions are in the range of −78° C. to reflux. The reactions can be carried out in a solvent that will dissolve the reactants and is inert to both the reactants and products. Solvents include, but are not limited to, dimethyl sulfoxide, diethyl ether, tetrahydrofuran, N,N-dimethyl-formamide, methylene chloride crown ethers and the like.

Alternatively, the halide in VIII can be converted to the corresponding organometallic compound, e.g., a Grignard reagent using the procedures known in the art and adding the reacting Grignard reagent to dry ice, followed by acid hydrolysis, thereby forming the carboxylic acid. If the molecule contains groups which are reactive towards the Grignard reagent, e.g., ketones, hydroxy, amino, then these groups should be protected with protecting groups known in the art. Examples of many of the possible protecting groups that may be utilized are found in "Protective Groups in Organic Synthesis," by T. W. Green, John Wiley and Sons, 1981. For example, the ketone may be protected as the ethylene ketal.

The carboxy substituent synthesized hereinabove can be converted to carbalkoxy by a Fischer esterification, or by reaction with the acid chloride according to the procedures discussed herein supra.

Similarly, by using the reaction conditions discussed hereinabove, and by starting with a molecule wherein $R_{16}$, as defined in the claims, replaces $R_{17}$, the stereochemical isomer of IIC can be formed.

An exemplary procedure for the preparation of an 16-ξ-amino subsituents is as follows:

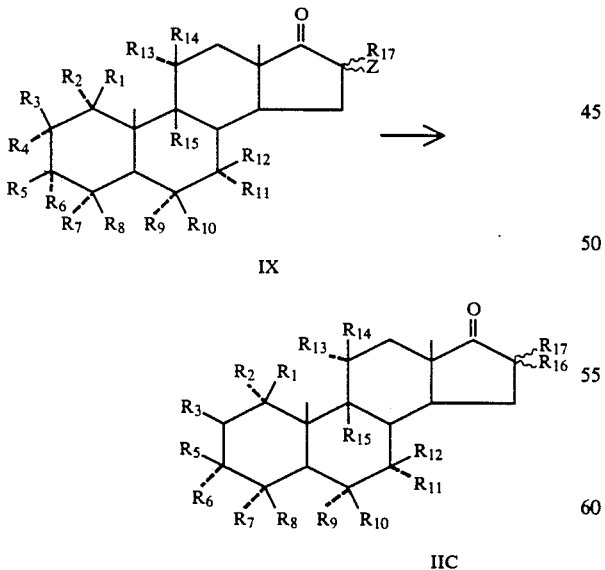

wherein $R_1$–$R_{15}$ are as defined hereinabove with the proviso that none are halo, $R_{16}$ is amino or alkylamino or dialkylamino and $R_{17}$ is independently amino, loweralkylamino, diloweralkylamino, aminoloweralkyl, loweralkyl aminolower alkyl, diloweralkylaminolower alkyl, loweralkoxyloweralkyl, lower alkoxy, hydroxy lower alkyl, monohaloloweralkyl, dihaloloweralkyl, trihaloloweralkyl, loweralkanoyl, formyl, lower carbalkoxy, or lower alkanoyloxy and Z is halo, such as chloride, bromide, mesylate or tosylate.

The amino group can be added by reacting IX with liquid ammonia under conditions known in the art. Reaction temperatures are in the range of −78° C. to reflux. The reaction can be carried out in a solvent that will dissolve both reactants and is inert to both reactants and products as well. Solvents include, but are not limited to diethyl ether, tetrahydrofuran, N,N-dimethylformamide, methylene chloride and the like.

The amine can also be prepared by a Hofmann degradation of the corresponding amide using bromine and a strong base, such as sodium hydroxide or sodium methoxide. The amide in turn can be synthesized from the reaction of ammonia with an acid chloride which is derived from reacting the carboxylic acid prepared according to the procedure described hereinabove with a chlorinating agent such as thionyl chloride, phosphorus trichloride and phosphorus pentachloride.

Another method for the formation of the amine is the catalytic reduction of the 16-nitro substituent with hydrogen over palladium, platinum or nickel or with lithium aluminum hydride. The nitro group can be prepared by reacting the corresponding alkyl halide with nitride according to procedures known in the art.

The primary amine can also be prepared from reacting IX when Z is halide with hexamethylene tetramine followed by cleavage of the resulting salt with ethanolic hydrochloric acid in accordance with Delepine reaction conditions.

The alkylamino substituent can be prepared by reacting an alkyl halide with an excess of the amine generated hereinabove according to the procedures known in the art. Similarly, the dialkylamino substituent can be prepared by reacting an excess of the alkylamino with an alkyl halide according to procedures known in the art. In the case wherein the alkyl groups in alkylamino or dialkylamino is methyl or ethyl, an amine can be reacted with diazomethane or diazoethane generated in situ, respectively in the presence of a catalyst such as $BF_3$ or cuprous cyanide.

Similarly, using the procedures discussed hereinabove, and by starting with a molecule wherein $R_{17}$ is replaced by $R_{16}$, as defined in the claims, the corresponding stereoisomer of IIC can be prepared.

Formylation at carbon-16 can be effected by reducing the 16 acyl halide formed hereinabove with lithium tri-t-butoxy aluminum hydride in diglyme at −78° C. under Rosenmund reduction reaction conditions. Other reduction systems include palladium on charcoal as the catalyst with ethyl diisopropylamine as the acceptor of HCl and acetone as the solvent. In both of these cases, it is preferable that the ketone at C-17 be protected with protecting groups knonw in the art. Examples of many of the possible protecting groups that may be utilized are found in "Protective Groups in Organic Synthesis" by T. W. Green, John Wiley and Sons, 1981. For example, the ketone may be protected as the ethylene ketal.

Alternatively, the carboxylic acid esters generated hereinabove can be reduced to aldehydes with (isoBu)$_2$AlH at −70° C., with diamino-aluminum hydrides, and with $NaAlH_4$ at −65° C. to −45° C. according to the procedures known in the art.

The 16-formyl group can also be prepared by reducing an excess of the amide prepared hereinabove with LiAlH₄ according to procedures known in the art.

In both of these reactions, as before, the C-17 keto group should be protected with a protecting group.

The 16-formyl group can be prepared by reacting the 16-halo substituent with sodium tetracarbonyl-ferrate (II) in the presence of triphenylphosphine followed by quenching the product thereof with acetic acid:

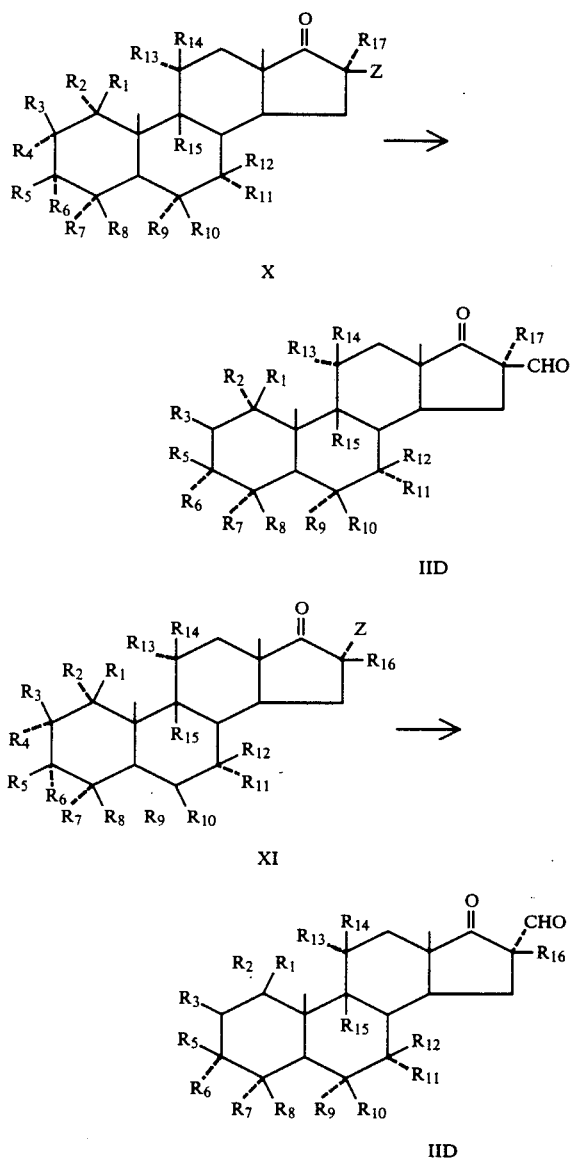

The reagent Na₂Fe(CO)₄ can be prepared by treatment of iron pentacarbonyl with sodium amalgam in tetrahydrofuran.

The lower alkanoyl groups can be prepared by reacting the 16-halo groups discussed hereinabove with sodium tetracarbonylferrate (II) in the presence or absence of triphenylphosphine and reacting the product therefrom with an alkyl halide according to the procedures of Collman, et al., JACS 94, 1788 (1972).

Alternatively, the 16-halo substituent can be converted to a Grignard reagent, which subsequently reacts with a lower alkanal or lower alkanone, thereby forming an alcohol intermediate which is then oxidized with a strong oxidizing agent, such as acid dichromate, potassium permaganate, bromine, manganese dioxide, ruthenium tetoxide, Jones reagent, and the like. In this sequence of reaction, the ketone at carbon-17 must be protected with protecting groups known in the art, e.g., as an ethylene ketal, prior to the formation of the Grignard.

An internal ketone, i.e., a C-16 substituent wherein the carbonyl group is on a carbon which is not α to the steroidal ring, can be prepared according to the procedures outlined hereinabove from the appropriate internal alcohol or halide:

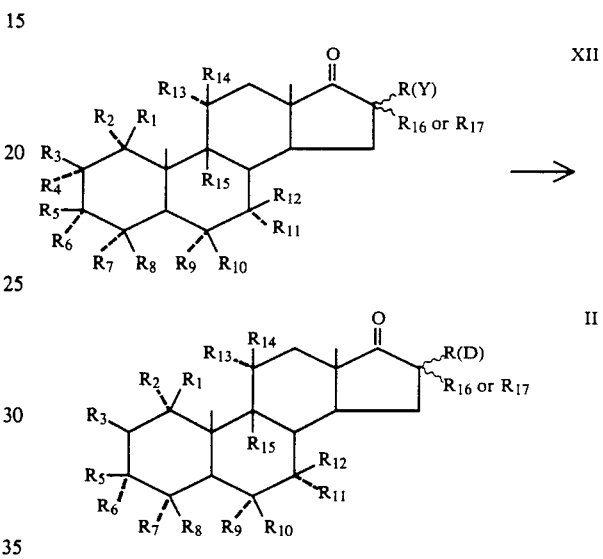

wherein $R_1$–$R_{15}$ are as defined hereinabove and $R_{16}$ and $R_{17}$, whichever is present is amino, loweralkylamino, diloweralkylamino, aminoloweralkyl, loweralkyl aminolower alkyl, diloweralkylaminolower alkyl, loweralkoxyloweralkyl, lower alkoxy, hydroxy lower alkyl, monohaloloweralkyl, dihaloloweralkyl, trihaloloweralkyl, loweralkanoyl, formyl, lower carbalkoxy, or lower alkanoyloxy; R(Y) is an alkyl group substituted with a hydroxy group or a halide group and R(D) is an alkyl group containing an oxo group.

The alkyl substituted halo group and hydroxy groups can be prepared according to the procedures described hereinafter.

For example, the 16 α-trihalo alkyl derivative can be prepared by the exemplary procedure described hereinbelow:

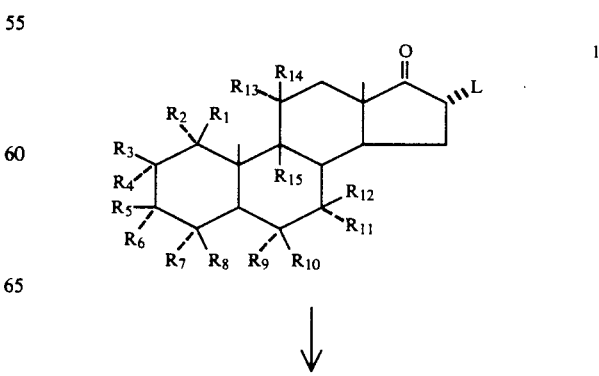

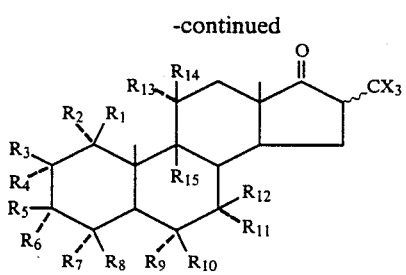

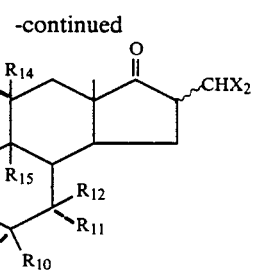

In the above scheme, $R_1$–$R_{15}$ is as described hereinabove, L is a good leaving group known to one skilled in the art such as bromo, chloro, tosylate, mesylate and X is halo, i.e., fluorine, bromo, chloro or iodo.

Treatment of 5 α-androstan-17-one(1) or the corresponding 5 androsten-17-one with a trihalomethyl metal reagent such as trifluoromethyl copper according to the procedure by Koba Yashi et al. in Tetrahedron Letters, 42,4071 (1979) affords the corresponding 16-trihalomethyl substituent.

An exemplary procedure for the preparation for the dihaloalkyl substituent is shown hereinbelow:

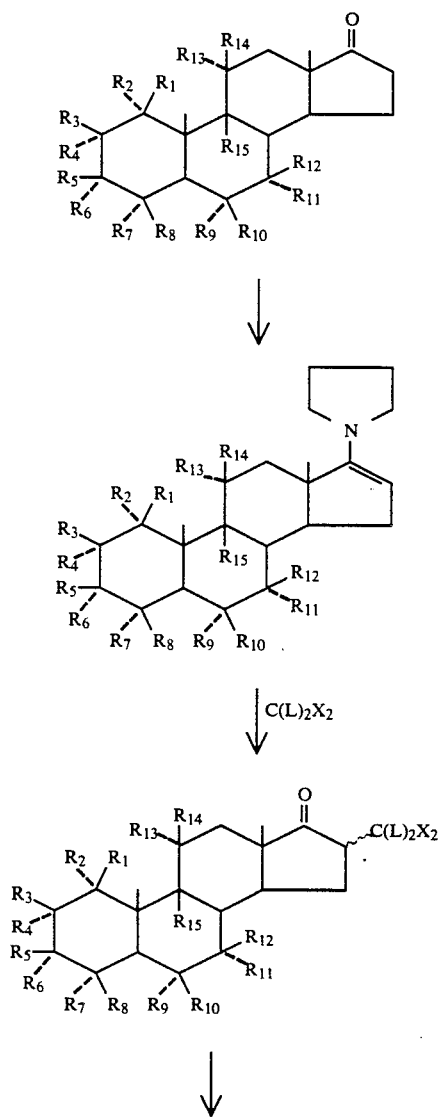

In the above scheme, $R_1$–$R_{15}$ are as defined hereinabove, X is halo and L is a good leaving group such as bromo, chloro, mesylate, tosylate and the like.

5 α-androstan-17-one(1) derivative or the corresponding 5-androsten-17-one is converted to its enamine (2) under Stork enamine reaction conditions. (See, Stork, et al. JACS 85, 207 (1963); Kuehne, Synthesis 510–537 (1970)). The corresponding enamine is converted to the dihaloalkyl e.g., $CHF_2$, by reacting 2 with a dihalo substituent having a good leaving group such as bromo, chloro, mesylate or tosylate. Removal of the leaving group such as by treatment with Lewis acid (e.g., Zn/ACOH) affords the 16-dihalo derivative (3).

The preparation of aminomethyl groups at C-16 can be effected by catalytic reduction of the 16-CN substituent prepared hereinabove using hydrogen on palladium, platinum or nickel or with lithium aluminum hydride. The 16-aminoalkyl substituent can be reacted with alkyl halides to form the 16-alkylaminoalkyl and dialkylaminoalkyl in accordance with the procedure described hereinabove. Alternatively, the steroid of Formula XIII can be reacted with alkylamino according to the procedure of Julian, et al. JACS, 70, 3872 (1948):

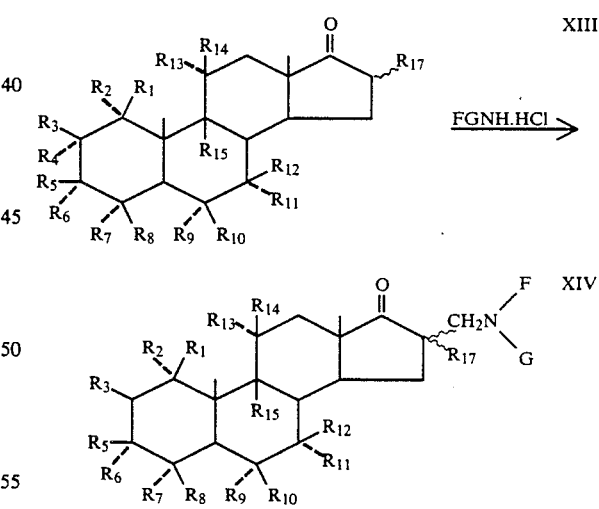

wherein $R_1$–$R_{15}$ are as defined hereinabove, and F and G are independently hydrogen or loweralkyl and $R_{17}$ is amino, loweralkylamino, diloweralkylamino, aminoloweralkyl, loweralkyl aminolower alkyl, diloweralkylaminolower alkyl, loweralkoxyloweralkyl, lower alkoxy, hydroxy lower alkyl, monohaloloweralkyl, dihaloloweralkyl, trihaloloweralkyl, loweralkanoyl, formyl, lower carbalkoxy, or lower alkanoyloxy.

Similarly, by substituting $R_{16}$ for $R_{17}$ in XIII, the corresponding stereochemical isomer of XIV can be prepared.

If a longer amine chain is desired, then a compound of Formula III can be reacted with a strong base, such as t-BuOK, sodium pentoxide, NaNH$_2$, sodium, n-BuLi and the like followed by an amine substituted alkyl halide according to procedures known in the art. Alternatively, the 16-halo derivative of XIII can be reacted with an amine-substituted R$_2$CuLi:

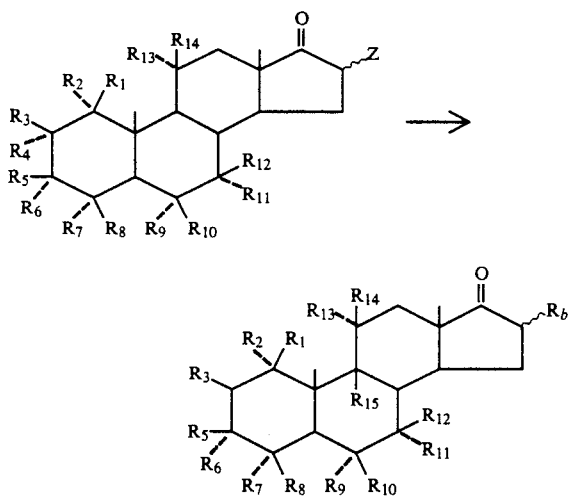

wherein R' is an alkyl group containing an amine functionality and R$_b$ is an alkyl group containing an amine moiety, R$_1$–R$_{15}$ is as defined hereinabove and Z is a halide. The R'$_2$CuLi, reagents can be prepared by mixing two mole of R'Li with 1 mole of cuprous halide in ether at a low temperature or by dissolving an alkyl copper compound in an alkyl lithium solution.

The hydroxyalkyl substituent can be prepared by reacting XIII with an alkoxy substituted R$_2$'CuLi according to the procedure described hereinabove, followed by aqueous acid hydrolysis, thereby forming the 16-alkylhydroxy groups.

A 16 hydroxy methyl substituent can be prepared by formylation of the 17-ones, followed by reduction thereof in accordance with the procedure of C. H. Robinson, et al., J. Org. Chem., 28, 975 (1963).

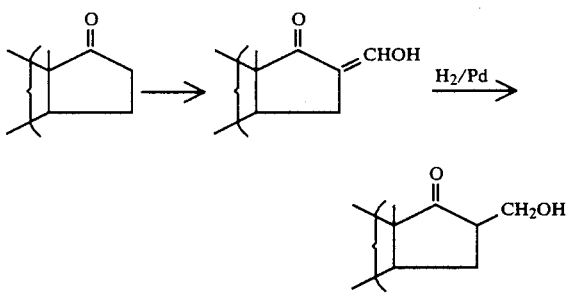

In the reaction sequence hereinabove, the formulae therein are only focusing on the chemistry of the D-ring of the steroids. The A, B, and C rings with the substituents attached thereto, as defined, hereinabove are presumed to be present.

The 16 alkyl halo groups are prepared from the hydroxy group formed hereinabove by methods known in the art. The 16 alkyl chloro substituent can be prepared from the reaction of the corresponding alcohols with HCl, SOCl$_2$, PCl$_5$, PCl$_3$ or POCl$_3$. The bromide is prepared by reacting the corresponding alcohol with HBr while the iodide is prepared by reacting the corresponding alcohol with HI. The fluoride is prepared by reacting the corresponding alcohol with sulfur trifluoride (DAST). Alternatively, the halides can be prepared by halide exchange in accordance with the Finkelstein reaction conditions.

The di- and tri-haloalkyl substituents are similarly prepared.

The following procedure is exemplary for the preparation of the 16 spiro cycloalkyl derivatives:

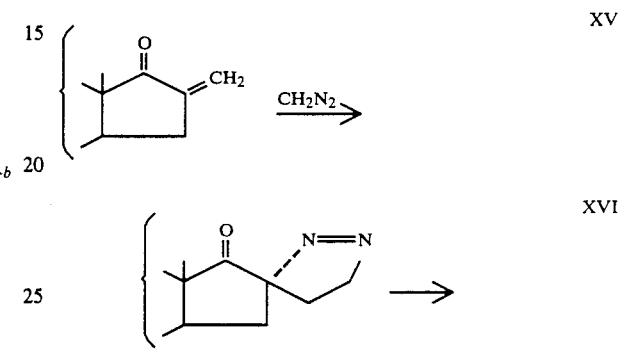

A diazoalkane, e.g., diazomethane, which is generated in situ by known chemical reactions, is reacted with a 16-methylene-17-one to yield the spiro-pyrazoline derivative (XVI) according to the procedure outlined by Bruckner, et al., Chem. Ber. 94, 2897 (1961). Pyrolysis of the spiro pyrazoline intermediate or cleavage in the presence of boron trifluoride etherate affords the 16 spirocyclopropyl steroid.

Similarly, by substituting diazoethane for diazomethane hereinabove, the 16-spirocyclobutyl derivative can also be prepared.

The 16-methylene compound (XV) is prepared from heating 16-dimethylaminomethyl-17-one (XVII) with acetic acid and acetic anhydride. The 16-dimethylamino methyl-17-one (XVIII) derivative is in turn prepared by condensation of the 17-one with dimethylamine hydrochloride and paraformaldehyde, according to the procedure by Julian, et al. JACS, 70 3872 (1948). The sequence for formation of the 16-methylene compound is as follows:

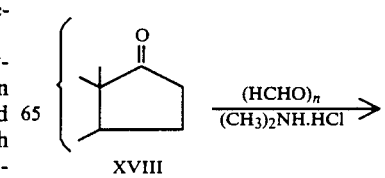

XVIII

-continued

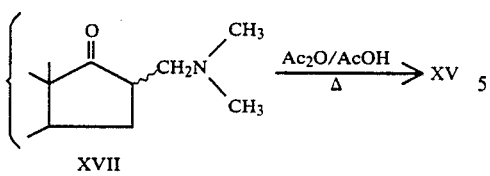

An exemplary procedure for the preparation of 16-oxymethylene derivatives is as follows:

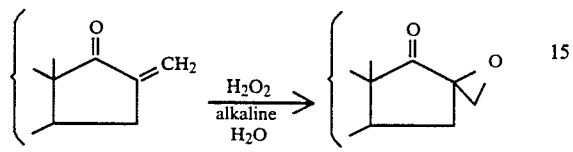

A 16-methylene derivative is reacted with an alkaline aqueous solution of hydrogen peroxide, forming the 16-oxymethylene derivative.

The compounds encompassed by Formulae III–XIII can be prepared from steroids which are known or are readily available. The substituents of these compounds can be added by combination of the representative reactions outlined below.

Preparation of 3-Desoxy Compounds

The 3-desoxy compounds are prepared from the corresponding 3-hydroxy compounds by techniques known in the art. For example,

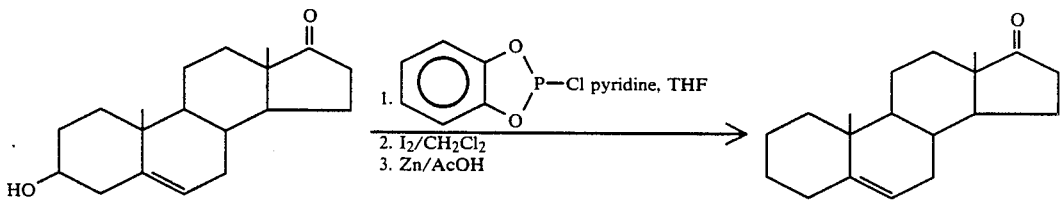

DHEA dissolved in an inert solvent, such as tetrahydrofuran was reacted with O-phenylene phosphorchloroidite. The resulting product was reacted with iodine to form the 3-iodo derivative which in turn is reacted with a Lewis acid, such as zinc in acetic acid to form the corresponding 3-desoxy compound.

ALKYLATION

CARBON-1-ALKYLATION

A representative procedure for alkylation at carbon-1 and specifically the synthesis of a 1α-methyl DHEA 3 a and 1α-methyl-desoxy DHEA 3b is given in Scheme 1.

Scheme 1

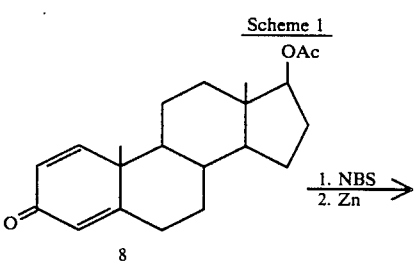

-continued
Scheme 1

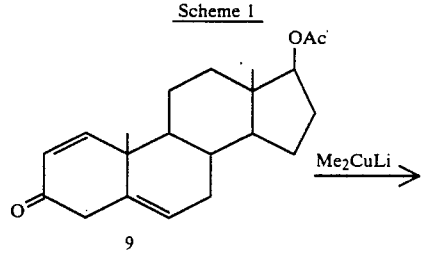

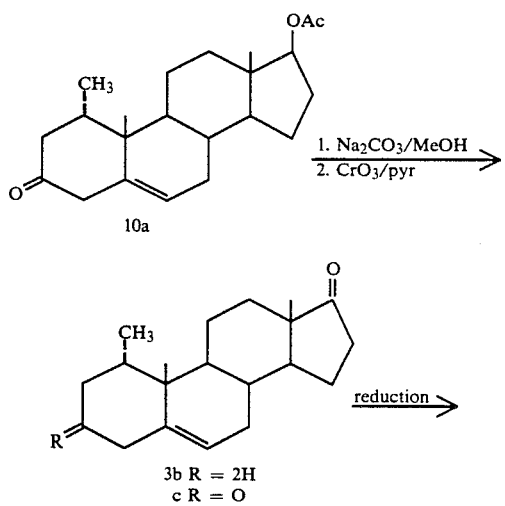

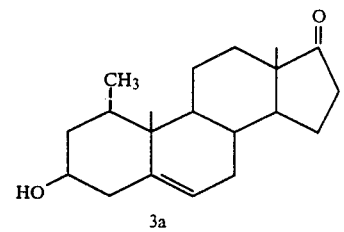

Allylic bromination (e.g. with N-bromosuccinimide (NBS)) of 17 β-acetoxyandrosta-1,4-dien-3-one 8 followed by treatment with zinc affords the non-conjugated enone 9. 1,4-Alkylation with lithiodimethyl cuprate provides the 1α-methyl ketone 10a. At this stage the 10a may be converted to a methylene by Wolff-Kishner reduction or the Huang Minlon modification thereof. These vigorous reaction conditions result in hydrolysis of the resulting carbon-17 acetate thereby yielding the hydroxy desoxy derivative, 17β-hydroxy-1α-methylandrost-5-ene (3b). Both 10a and its desoxy derivative can be converted via standard reactions, i.e., hydrolysis of the 17-acetate with sodium carbonate and methanol followed by chromium trioxide oxidation of the resulting 17-alcohol to the carbon-17 ketone. Selective reduction of the carbon-3 ketone, 3,17-diketone 3c using sodium borohydride pyridine (pyr) yields 1α-methyl dehydroepiandrosterone 3a.

CARBON-2-ALKYLATIONS

The following procedures are illustrative for alkylation at carbon-2 and are figuratively illustrated in Scheme 2 below.

Alkylation of testosterone (I) with an alkylating agent, such as methyl iodide, in the presence of a strong base, such as t-BuOK, sodium t-pentoxide, lithium diisopropylamide (LDA), Na NH$_2$, Et$_2$Ni, n-butyl lithium and the like gives a mixture of the 2α- and 2β-alkyl-17-β-hydroxy-4-androsten-3-one (2 and 3). Treatment of the mixture with a strong base, such as sodium methoxide in methanol, epimerizes the 2β-axial alkyl to the 2-α-equitorial configuration (2). Acetylation of 2 with an acetylating agent, such as acetic anhydride (Ac$_2$O) and p-toluenesulfonic acid (p-TSA) in toluene afforded 2α-methyl-3,17β-dihydroxy-3,5-androstadien-3,17-diacetate (4). Treatment of the diacetate (4) with sodium borohydride in 95% ethanol yielded 2α-methyl-3β,17β-dihydroxy-5-androsten-17-acetate (5). Protection of the 3-hydroxy group as a tetrahydropyranyl ether followed by hydrolysis of the 17-acetate yielded 2α-methyl-3β,17β-dihydroxy-5-androsten-3-tetrahydropyranyl ether 7. Oxidation of the C-17 hydroxy group in 7 followed by hydrolysis of the tetrahydropyranyl ether with hydrochloric acid and aqueous acetone yielded 3β-hydroxy-2α-methylandrost-5-en-17-one (9).

The following is a specific example for the synthesis of 2α-methyl DHEA.

To a solution of diisopropylamine (5.3 ml, 38 mmol) in freshly distilled tetrahydrofuran (80 ml) stirred at −78° C. was added n-butyllithium (29.3 ml of 1.3M in hexane, 38 mmol). This was stirred at −78° C. for 30 minutes then warmed to −30° and 17β-hydroxy-4-androsten-3-one (1) (5.0 g, 17.3 mmol) in tetrahydrofuran (30 ml) was added dropwise. After 30 minutes at −30° C. iodomethane (4 ml, 80 mmol) was added. The mixture was allowed to slowly warm to room temperature with stirring, then saturated ammonium chloride solution was added and the product was extracted with ether. The organic layer was dried and the solvent removed to give a mixture of isomers 2 & 3 as an oil (5.26 g) which was used in the next step.

To a stirred solution of sodium (0.75 g, 32 mmol) dissolved in methanol (100 ml) was added the epimeric mixture of 2-methyl-17β-hydroxy-4-androsten-3-one, 2 & 3 (4.93 g, 16.2 mmol) in methanol (100 ml). After 17 hours at room temperature, saturated ammonium chloride solution was added and most of the solvent was removed in vacuo. The product was extracted with dichloromethane, washed with water, dried and the solvent removed to give a gum (4.86 g) which was purified by column chromatography on silica gel. Elution with hexane ether gave 1.6 g of 2 which crystallized from methanol mp 149°-151° C.;

H$^1$ NMR (CDCl$_3$) δ5.64 (s, 1, H-4), 3.60 (t, 1, H-17, J=9 Hz), 1.24 (s, 3, H-19), 1.13 (d, 3, H-2 methyl, J=6 Hz), 0.83 (s, 3, H-18); MS m/e 302 (M+, 33), 260 (21), 246 (29), 28 (100).

A solution of 2α-methyl-17β-hydroxy-4-androsten-3-one (2) (4.86 g, 16.1 mmol) product mixture from the previous step in acetic anhydride (40 ml) and paratoluene sulfonic acid (200 mg) in toluene (100 ml) was refluxed 3½ hours. Pyridine (1 ml) was added, and the mixture was concentrated on a rotary evaporator, then partitioned between methylene chloride and water. The organic layer was dried and the solvent removed. The product mixture (5.78 g) was separated on a flash silica column to give 2α-methyl-3,17β-dihydroxy-3,5-androstadien-3,17-diacetate (4) 1.81 g (27.4%) crystallized from Et$_2$O-hexane. mp 170°-171° C.

H$^1$ NMR (CDCl$_3$) δ5.57 (s, 1, H-4), 5.40 (m, 1, H-6), 4.55 (t, 1, H-17, J=9 Hz), 2.08 (s, 3, 3-acetate), 2.01 (s, 3,17-acetate), 1.06 (s, 3, H-19), 0.98 (d, 3, 2 methyl, J=6 Hz), 0.83 (s, 3, H-18); MS m/e 386 (M+, 3) 358 (12), 43 (100).

A suspension of 2α-methyl-3,17β-dihydroxy-3,5-androstadien-3,17-diacetate (4) (1.31 g, 3.4 mmol) and sodium borohydride (1.3 g) in 95% ethanol (100 ml) was stirred at room temperature for 3½ hours. The solution was cooled to 0° C. and glacial acetic acid was added, followed by saturated sodium bicarbonate solution. The product was partitioned between dichloromethane and water, the organic layer dried, and the solvent removed to give 1.23 g product mixture which was separated on 40 g of flash silica column eluted to give 5, 0.7 g from ether hexane) mp 179°-182° C.;

$^1$H NMR (CDCl$_3$) δ5.27 (m, 1, H-6), 4.62 (t, 1, H-17, J=9 Hz), 3.03 (t, 1, H-3, J=9 Hz) 2.05 (s, 3,17-acetate), 1.07 (s, 3, H-19), 1.02 (d, 3, 2-methyl, J=8 Hz), 0.83 (s, 3, H-18).

A solution of 2α-methyl-3β,17β-dihydroxy-5-androsten-17-acetate 5 (1.42 g, 4.1 mmol) dihydropyran (DHP) (10 ml) and paratoluene sulfonic acid (100 mg) in ether (50 ml) was stirred at room temperature for 17 hours. The ether solution was washed with saturated sodium bicarbonate solution, then water, and dried, and the solvent was removed to give the product mixture as an oil (1.65 g). The product was not purified but carried on to the next step.

2α-Methyl-3β,17β-dihydroxy-androst-5-ene-3-tetrahydropyranyl ether 17-acetate, 6, from the previous step (1.65 g, 3.84 mmol) was dissolved in a solution of 5% potassium carbonate in 4:1 methanol:water (100 ml) and refluxed 1.5 hours. Most of the solvent was removed under reduced pressure and the product was partitioned between chloroform and water. The organic layer was dried and solvent removed to give 1.45 g of the product 7 which was used in the next step.

The product mixture 7 from the previous step (1.45 g, 3.84 mmol) was dissolved in pyridine (10 ml) and added to the complex formed by mixing chromium trioxide (2 g) in pyridine (20 ml). This was stirred 2½ hours at room temperature, then 1:1 ether:benzene (30 ml) was added and the mixture was filtered through celite then silica gel. The solvent was removed to give the product mixture 8, 1.52 g as an oil, which was carried on to the next step.

A solution consisting of the product mixture 8 from the previous step (1.52 g, 3.94 mmol) and 3N HCl (2 ml) in acetone (40 ml) was stirred at room temperature for 3 hours. Saturated sodium bicarbonate solution was added and the product was extracted with dichloromethane. The organic layer was dried and the solvent removed to give 1.17 g product mixture which was separated on a flash silica column. Elution with 30:70 ether:hexane gave 3β-hydroxy-2α-methyl-androst-5-en-17-one (9) (317 g) which was crystallized from ether:hexane mp 171.5–173;

H$^1$ NMR (CDCl$_3$) δ5.45 (m, 1, H-6), 3.10 (broad m, 1, H-3) 1.13 (s, 3, H-19), 1.07 (d, 3, 2methyl, J=8 Hz), 0.97 (s, 3 H-18).

As stated before, the above reactions involving alkylation at carbon-2 are figuratively illustrated in Scheme 2.

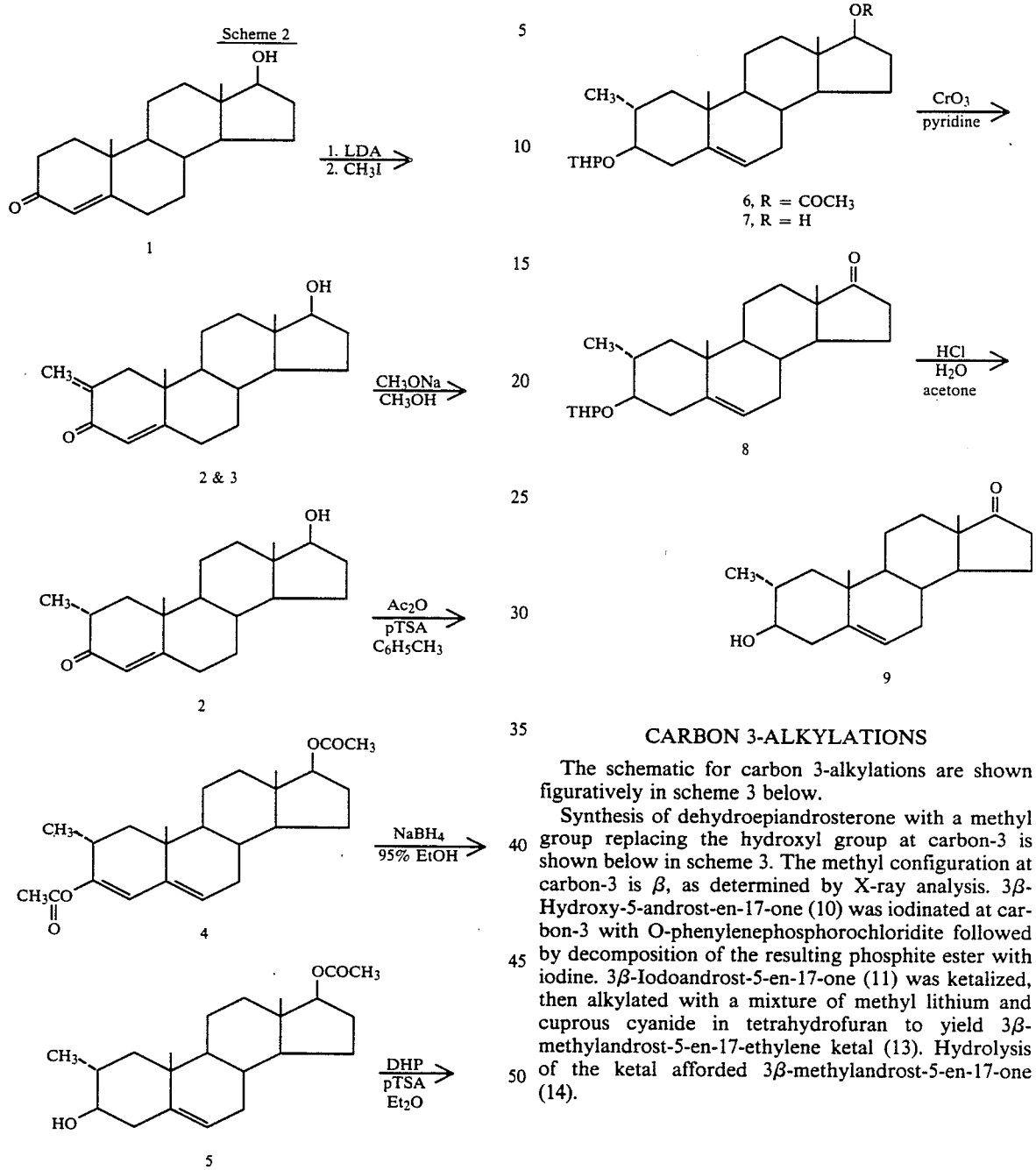

CARBON 3-ALKYLATIONS

The schematic for carbon 3-alkylations are shown figuratively in scheme 3 below.

Synthesis of dehydroepiandrosterone with a methyl group replacing the hydroxyl group at carbon-3 is shown below in scheme 3. The methyl configuration at carbon-3 is $\beta$, as determined by X-ray analysis. 3$\beta$-Hydroxy-5-androst-en-17-one (10) was iodinated at carbon-3 with O-phenylenephosphorochloridite followed by decomposition of the resulting phosphite ester with iodine. 3$\beta$-Iodoandrost-5-en-17-one (11) was ketalized, then alkylated with a mixture of methyl lithium and cuprous cyanide in tetrahydrofuran to yield 3$\beta$-methylandrost-5-en-17-ethylene ketal (13). Hydrolysis of the ketal afforded 3$\beta$-methylandrost-5-en-17-one (14).

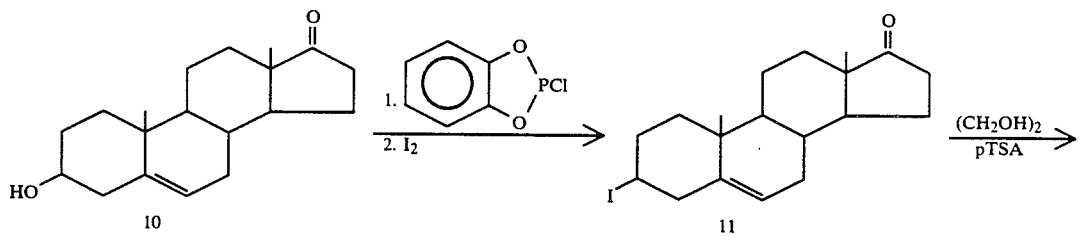

-continued
Scheme 3

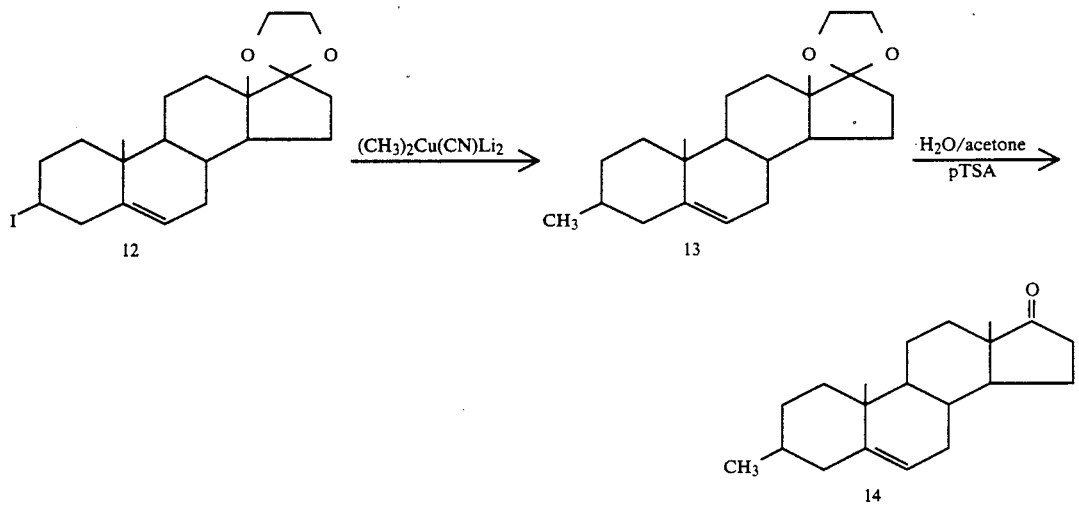

More specifically, 3β-iodoandrost-5-en-17-one (11) (11.83 g, 29.7 mmol), ethylene glycol (20 ml) and p-toluene sulfonic acid (200 mg) in benzene (250 ml) were refluxed under a Dean-Stark trap for 72 hrs. The solution was washed with saturated sodium bicarbonate, water, then dried over magnesium sulfate. Evaporation and recrystallization from ether afforded 11.5 g (87.3%) of 3β-iodoandrost-5-en-17-one-17-ethyleneketal (12): mp 140°–141° C., IR (KBr): 3010, 2940, 1470, 1425, 1375 cm$^{-1}$; $^1$H NMR (CDCl$_3$): δ5.44 (brd J=6 Hz, 1H, H-6), 3.91 (s, 4H, ketal), 1.07 (s, 3H, C-19 Me), 0.88 (s, 3H, C-18 Me); MS (m/e): 442 (M$^+$, 1), 380 (35), 315 (57), 253 (67), 227 (11), 105 (24), 99 (100), 91 (35), 55 (27), 41 (33).

Cuprous cyanide (4.465 g, 49.9 mmol) was placed in a dry 500 ml 3 neck round bottom flask equipped with a magnetic stirrer. The system was flushed with N$_2$, and dry THF (30 ml) was added. The suspension was cooled to −78° C. and MeLi solution, 1.5M (66.5 ml, 99.8 mmol), was added via a syringe. The solution was allowed to warm to 0° C. for 5 min., which resulted in a clear tan solution.

After recooling to −78° C., the 3β-iodo-17-ketal (3) (7.35 g, 16.6 mmol) in 40 ml dry tetrahydrofuran was added via a syringe, and the solution was allowed to warm to room temperature and was stirred for 18 hrs. under N$_2$. The solution was extracted with 100 ml of 90% saturated NH$_4$Cl/10% conc. NH$_4$OH. The organic layer was separated, dried over MgSO$_4$ and evaporated to give 6.69 g of crude product. Chromatography on flash silica (240 g) and elution with 1% Et$_2$O/99% hexane gave 6.41 g of colorless crystals. Recrystallization from methanol (200 ml) gave 3β-methylandrost-5-en-17-one 17-ethyleneketal. mp 121°–122° C.

Anal. Calc. C 80.06, H 10.38. Found C 80.12, H 10.55.
IR (KBr) 3010, 2930, 1450, 1430, 1370 cm$^{-1}$; $^1$H NMR (CDCl$_3$): δ5.33 (brd J=6 Hz, 1H, H-6), 3.90 (s, 4H, ketal), 1.03 (s, 3H, C-19 Me) 0.91 (s, 3H, C-18 Me); 0.97 (d, 3H, C-3 Me); MS (m/e): 330 (M$^+$, 16), 316 (7), 268 (29), 253 (22), 239 (9), 99 (100), 91 (22), 55 (27), 41 (22).

The 3β-methylandrost-5-en-17-one 17-ethylene-ketal (13) (2.20 g 6.7 mmol) was dissolved in acetone (100 ml). p-Toluenesulfonic acid (100 mg) and H$_2$O (20 ml) were added and the solution was refluxed for 2 hrs. The solution was evaporated, taken up in ether (30 ml), washed with saturated NaHCO$_3$, H$_2$O, and then dried over MgSO$_4$. The solution was filtered and evaporated to give a colorless solid which was recrystallized from methanol to give 3β-methylandrost-5-en-17-one (14) as colorless plates, 1.17 g (61%) mp 148°–150° C.; IR (KBr) 3010, 2910, 1740, 1455, 1430, 1365 cm$^{-1}$; $^1$H NMR (CDCl$_3$): δ5.41 (brd, J=6 Hz, 1H, H-6), 1.11 (s, 3H, C-19 Me), 0.99 (s, 3H, C-18 Me), 1.07 (d, 3H, C-3 Me); MS (m/e) 286 (M$^+$, 58), 271 (51), 229 (31), 159 (36), 105 (72), 91 (95), 79 (89), 55 (9), 41 (100).

Anal. Calc. C 83.85, H 10.55. C 83.66, H 10.65.
Similarly, by using 3α-Hydroxyandrost-5-en-17-one, the 3α-methylandrost-5-en-17-one was prepared.

ALKYLATION AT CARBON-4

A procedure for carbon-4 alkylation and the synthesis of 4α-methyl DHEA is given in Scheme 4.

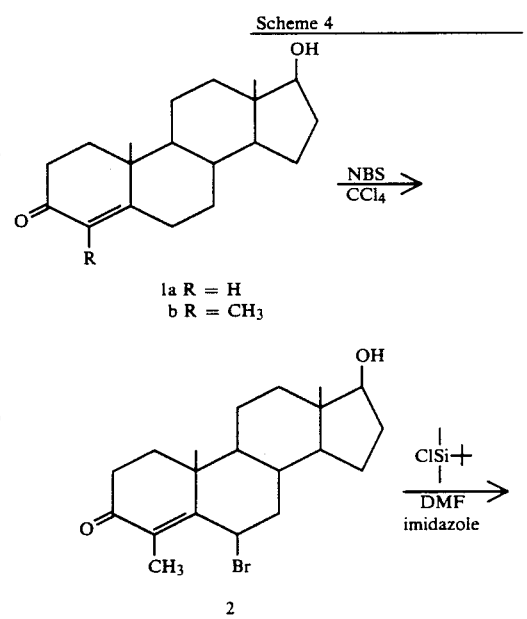

-continued
Scheme 4

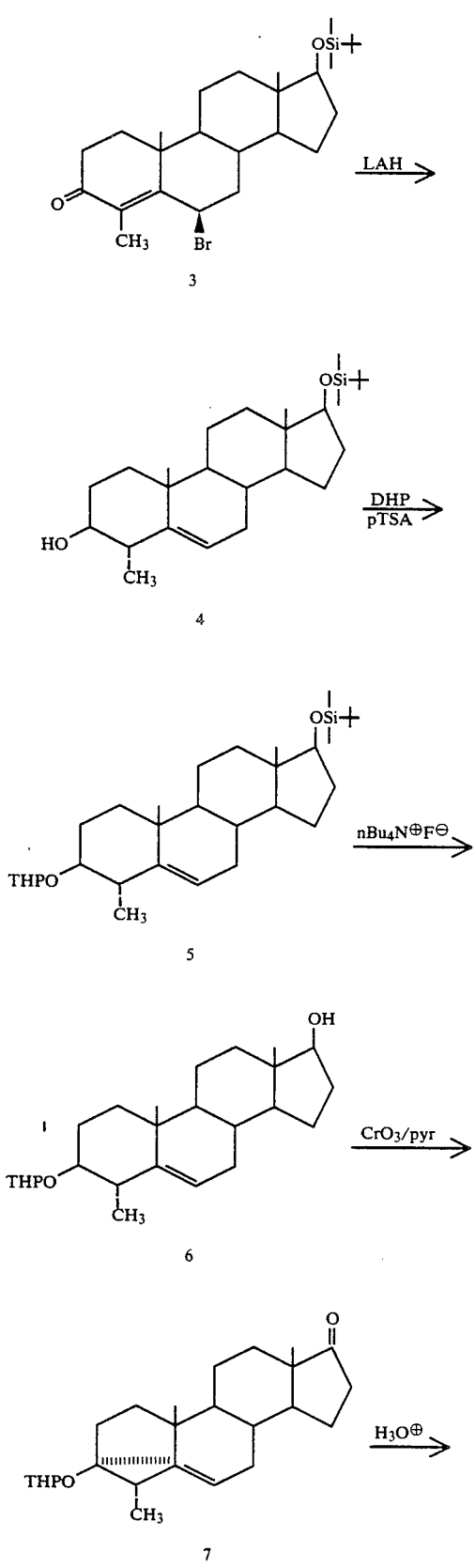

-continued
Scheme 4

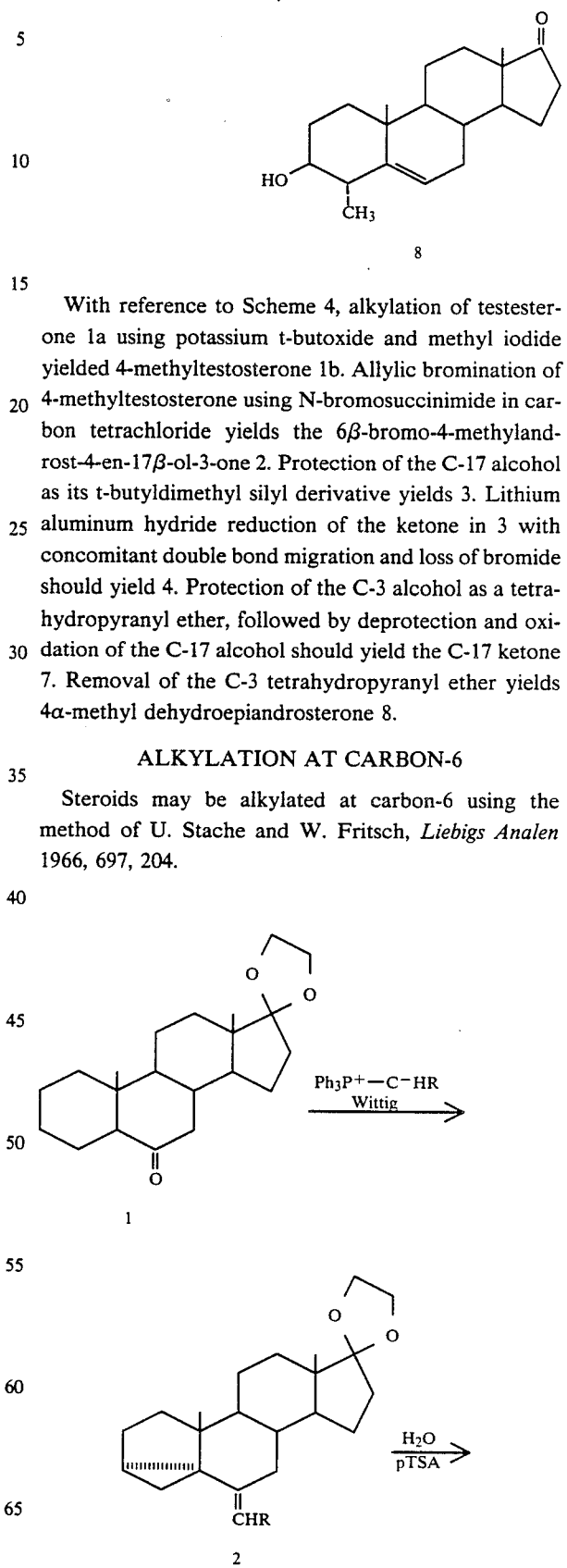

With reference to Scheme 4, alkylation of testesterone 1a using potassium t-butoxide and methyl iodide yielded 4-methyltestosterone 1b. Allylic bromination of 4-methyltestosterone using N-bromosuccinimide in carbon tetrachloride yields the 6β-bromo-4-methylandrost-4-en-17β-ol-3-one 2. Protection of the C-17 alcohol as its t-butyldimethyl silyl derivative yields 3. Lithium aluminum hydride reduction of the ketone in 3 with concomitant double bond migration and loss of bromide should yield 4. Protection of the C-3 alcohol as a tetrahydropyranyl ether, followed by deprotection and oxidation of the C-17 alcohol should yield the C-17 ketone 7. Removal of the C-3 tetrahydropyranyl ether yields 4α-methyl dehydroepiandrosterone 8.

ALKYLATION AT CARBON-6

Steroids may be alkylated at carbon-6 using the method of U. Stache and W. Fritsch, *Liebigs Analen* 1966, 697, 204.

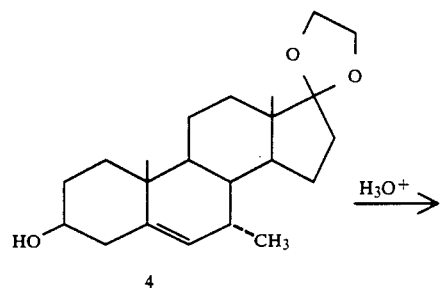

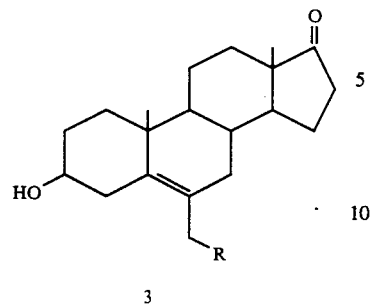

3α, 5-Cyclosteroids such as 3α, 5-cyclo-5α-androstan-6, 17-dione 17 ketal 1 are readily available by solvolysis of steroidal 5-ene-3β-tosylates and mesylates followed by oxidation of the C-6 hydroxyl group. Methylenation of 1 affords 6-methylene-3α, 5-cyclo-5α-androstan-17-one 17-ketal 2 (R=H). Treatment of 2 with aqueous acid results in the addition of water and the formation of 3β-hydroxy-6-methylandrost-5-en-17-one, 3 (R=H). Alkenylated derivatives of 3 may be synthesized starting with the appropriated substituted Witting reagent, such as $Ph_3P^{\oplus}$—$CH^{\ominus}$—$CH=CH_2$.

Alkylation at C-7

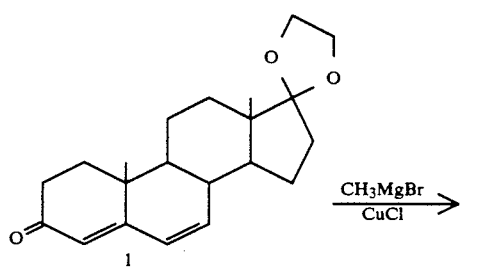

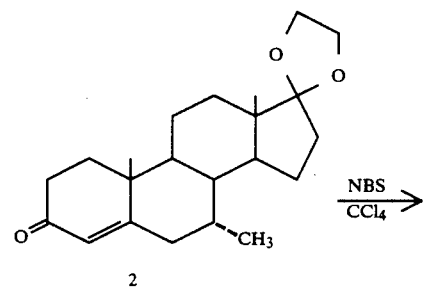

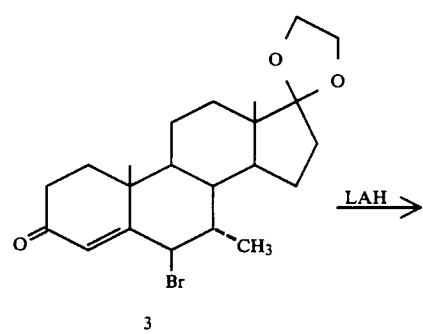

Alkylation of androsta-4,6-dien-3,17-dione 17 ketal 1 with methyl magnesium bromide in the presence of cuprous chloride, proceeds via conjugate addition to yield 7α-methylandrost-5-en-3,17-dione 17 ketal 2. Allylic bromination of 2 using N-bromosuccinimide in carbon tetrachloride yields the 6β-bromo-7α-methylandrost-4-en-3,17-dione 17 ketal 3. Lithium aluminum hydride reduction of the ketone in 3 with concomitant double bond migration and loss of bromide should yield 4. Deprotection of the C-17 ketone with aqueous acid yields 3β-hydroxy-7α-methylandrost-5-en-17-one, 5. Higher homologues may be synthesized using the substituted Grignard reagent i.e. R=CH₃, C₂H₅, C₃H₇. The 7β-epimer can be synthesized by treatment of 2 with DDQ-dichlorodicyanoquinone to generate another olefin at C-7. Catalytic reduction of this olefin should occur from the α face of the steroid to yield the 7β-methyl steroid i.e. 7β-methylandrost-5-en-3,17-dione 17 ketal. Following the same sequence as above yields 3β-hydroxy-7β-methylandrost-5-en-17-one.

Alkylation at Carbon-11

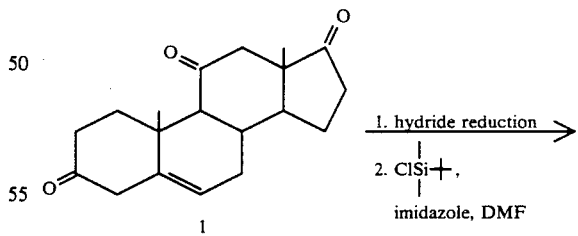

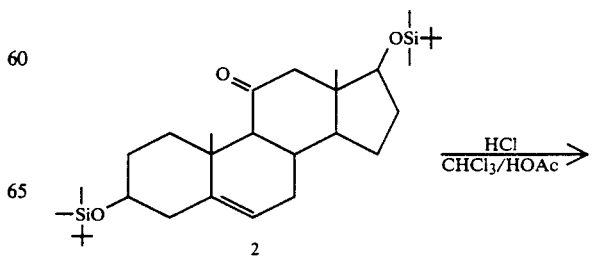

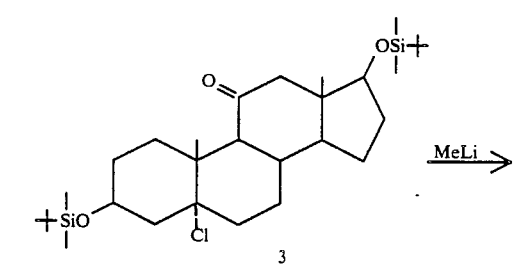
3

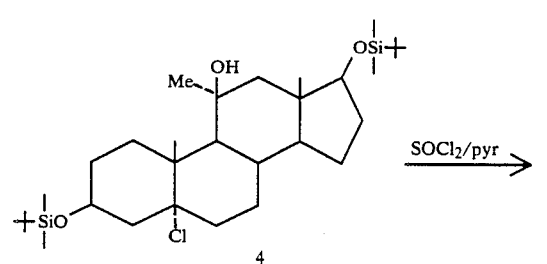
4

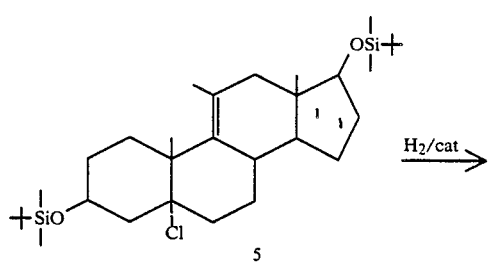
5

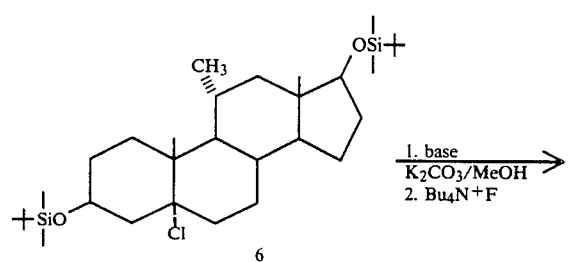
6

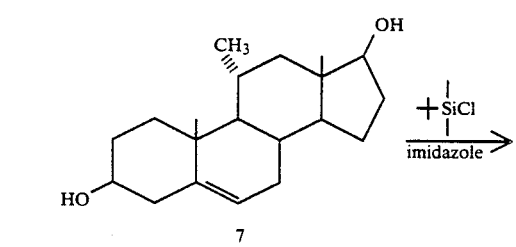
7

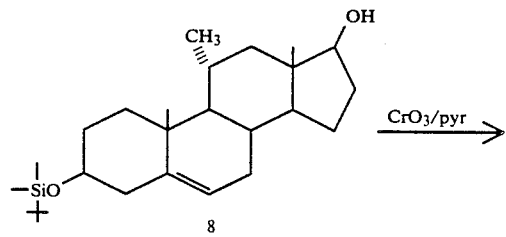
8

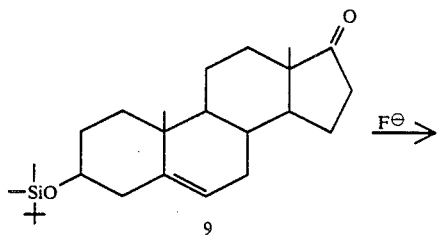
9

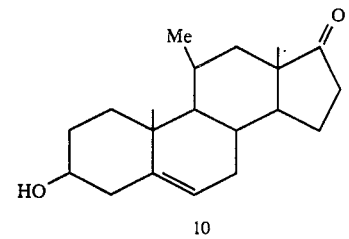
10

Due to the hindered nature of the C-11 ketone, selective reduction of androst-5-en-3,11,17-trione 1 with hydride should yield the C-3, C-17 dihydroxy steroid 2a, R=H which is protected as its bis(dimethyl-tert-butylsilyl)ether 2b R=Si(CH$_3$)$_2$t-Bu. Addition of hydrogen chloride across the C-5 olefin affords 5α-chloro-3β,17β-dihydroxyandrost-5-en-11-one 3,17-bis(dimethyl-t-butylsilyl) ether 3. Alkylation with methyl lithium proceeds from the less hindered α face to yield 5α-chloro-11α-methylandrostan-3β,11β,17β-triol-3,17-bis(dimethyl-t-butylsilyl) ether 4. Dehydration of the methylcarbinol 4 with thionyl chloride in pyridine provides the olefin 5. Catalytic hydrogenation of 5 gives the saturated 11α-methyl-5αchloro-bis (silyl) ether 6. Treatment of the chloro silyl ether 6 with base followed by tetrabutyl ammonium fluoride affords 11α-methylandrost-5-en-3β,17β-diol 7. Selective silylation yields 11α-methylandrost-5-en-3β,17β-diol 3-dimethyl t-butylsilyl ether 8. Oxidation of the C-17 alcohol in 8 yields 9 and deprotection of the 3-alcohol yields 11α-methylandrost-5-en-3β-ol-17-one 10. (11β-methyl DHEA).

The following procedures illustrate hydroxylation at Carbon-1, 2, 4, 7, 11 or 16.

C-1 HYDROXYLATION

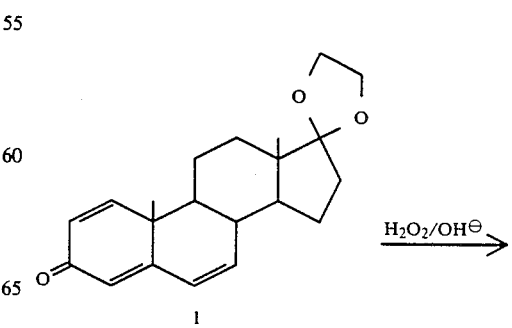
1

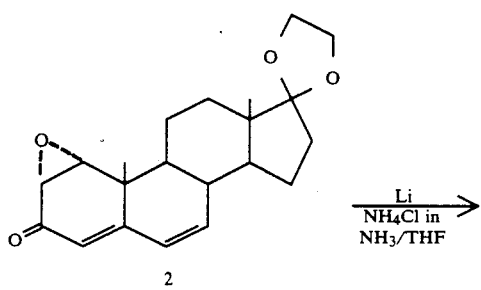

2

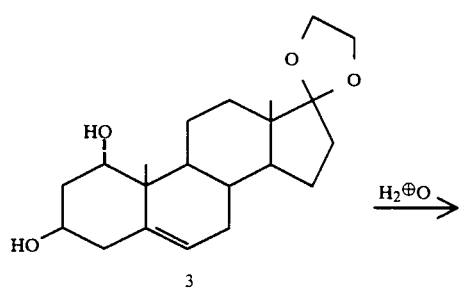

3

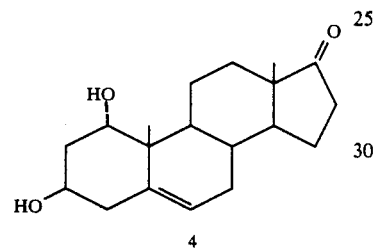

4

Alkaline hydrogen peroxide expoxidation of androsta-1,4,6-triene-3,17-dione 17-ketal 1 with basic hydrogen peroxide yields the 1α,2α-epoxide 2. Treatment of 1α,2α-epoxyandrosta-4,6-dien-3,17-dione 17-ketal 2 with a large excess each of lithium metal and ammonium chloride in ammonia-tetrahydrofuran (1:1) under reflux leads to 1α,3β-dihydroxyandrost-5-en-17-one 17-ketal 3. Hydrolysis of the ketal affords 1α,3β-dihydroxyandrost-5-en-17-one, 4. Also, fermentation of DHEA with *Penicillium aspergillus* affords 4, i.e. *Penicillium aspergillus* may be able to 1α-hydroxylate other substrates.

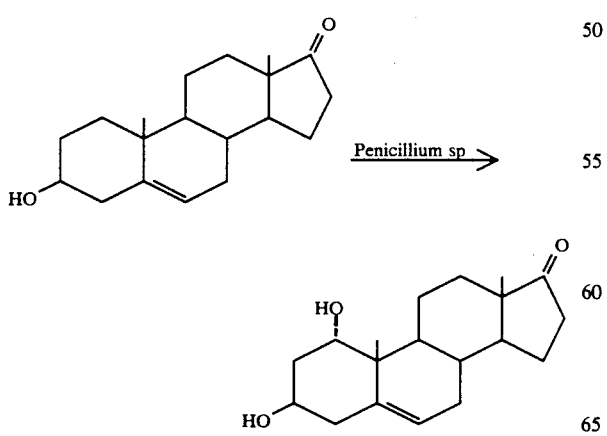

Dodson, R. M., Goldkamp, A. M., and Muir, R. D., *JACS*, 1957, 79, 3921.

Dodson, R. M., Goldkamp, A. M., and Muir, R. D., *JACS*, 1960, 82, 4026.

Penicillium hydroxylates DHEA at C-1 in the α-position. Therefore, other substrates that look like DHEA should by hydroxylated at C-1 by this enzyme.

C-2 HYDROXYLATION

2α,3β-dihydroxyandrost-5-en-17-one

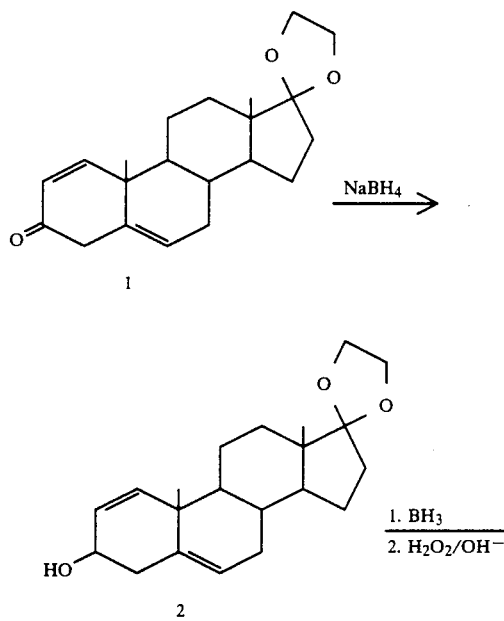

Reduction of androsta-1,5-dien-3,17-dione-17-ketal 1 with sodium borohydride yields 3β-hydroxyandrosta-1,5-diene-17-one 17-ketal 2. Hydroxylation of the C-1 double bond by hydroboration followed by oxidation with alkaline hydrogen peroxide affords 2α,3β-dihydroxyandrost-5-en-17-one 17-ketal 3. Deprotection of the C-17 ketone with aqueous acid yields 2α,3β-dihydroxyandrost-5-en-17-one, 4.

CARBON-4 HYDROXYLATION

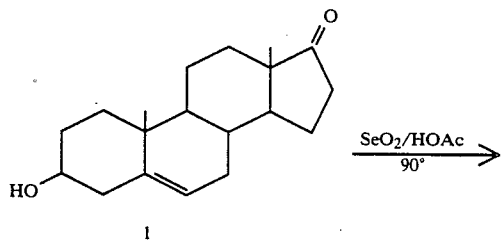

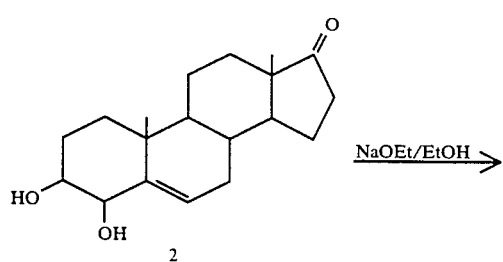

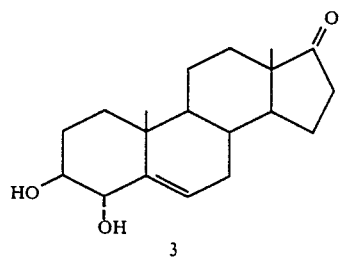

Selenium dioxide oxidation of 3β-hydroxyandrost-5-en-17-one yields 3β,4β-dihydroxyandrost-5-en-17-one 2. The axial C-4 alcohol may be epimerized to the equatorial position by reaction with sodium ethoxide in ethanol to yield 3β,4α-dihydroxyandrost-5-en-17-one, 3.

CARBON-7 HYDROXYLATION

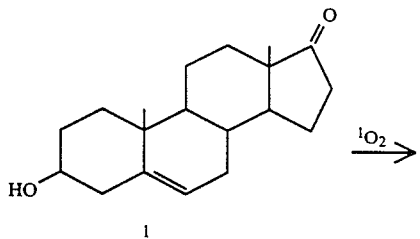

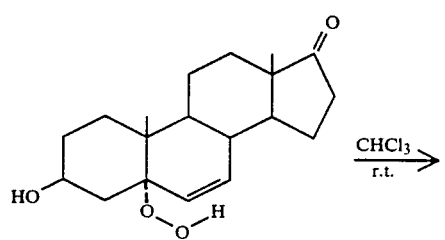

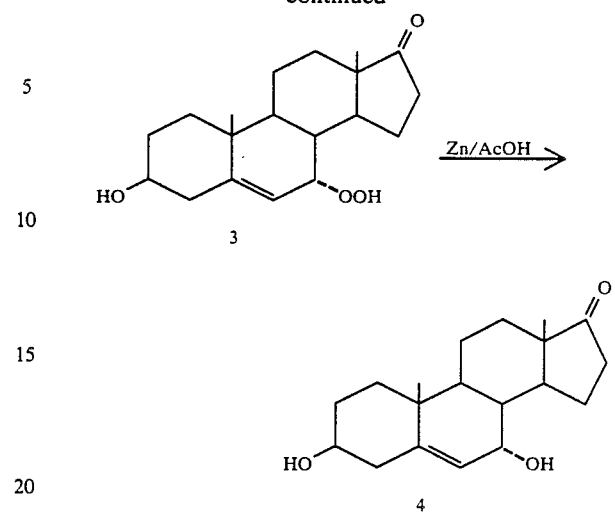

3β-Hydroxyandrost-5-en-17-one (DHEA) 1 reacts with singlet oxygen to yield 5α-hydroperoxy-3β-hydroxyandrost-6-en-17-one 2. This hydroperoxide undergoes a rearrangement when in chloroform solution to yield 7α-hydroperoxy-3β-hydroxyandrost-5-en-17-one, 3. Treatment of the hydroperoxide with zinc and acetic acid yields 3β,7α-dihydroxy-androst-5-en-17-one, 4.

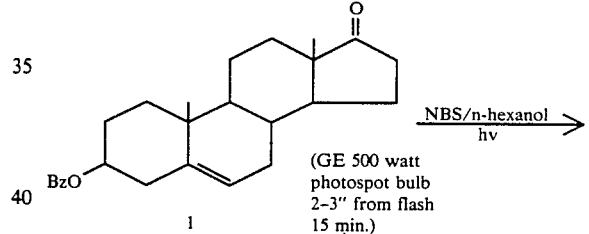

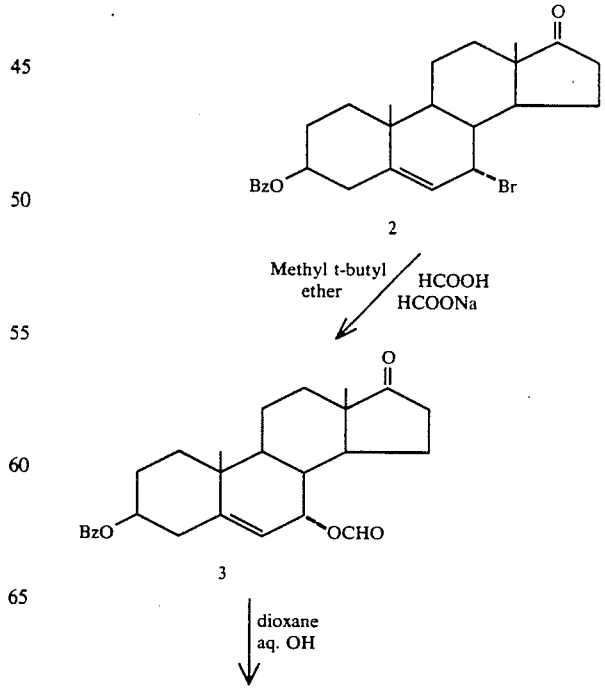

-continued

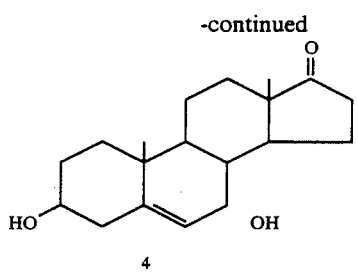

Alternatively, irradiation for approximately 15 minutes of 3β-benzyloxy-5-androsten-17-one 1 in the presence of NBS produces the 7-αBromo-3β-benzyloxy-5-androsten-17-one 2. The light source is provided by a G.E. 500 watt photospot bulb, which is placed 2–3" from the flask. Reaction of 2 with sodium formate in the presence of methyl t-butyl ether produces the formate ester 3. Substitution with aqueous base, such as OH−, results in the 3,7-dihydroxy-5-androsten-17-one 4.

CARBON-11 HYDROXYLATION

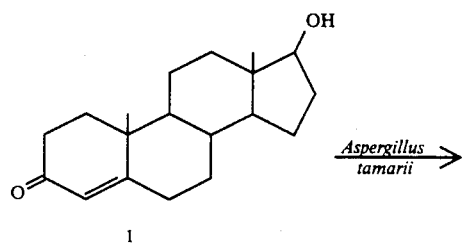

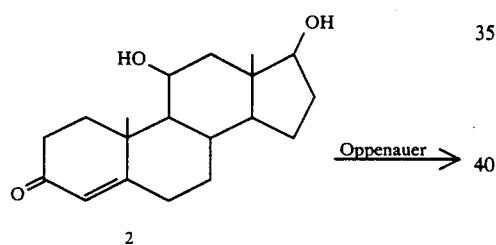

D. R. Brannon, J. Martin, A. C. Ochlschlager, N. N. Durham, and L. H. Zalkow, J. Org. Chem. 1965. 30, 760.

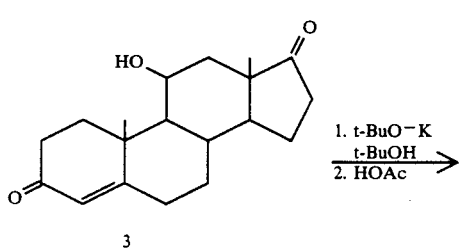

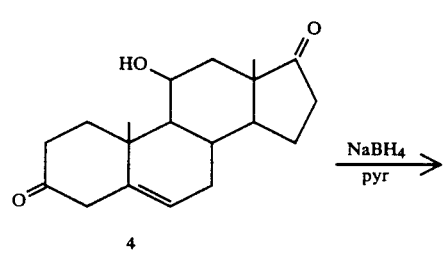

-continued

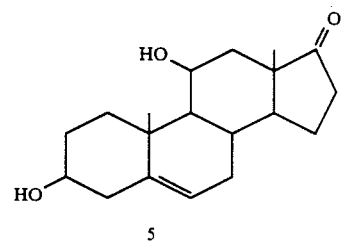

Hydroxylation of testosterone 1 at Carbon-11 using *Aspergillus tamarii* affords 11β,17β-dihydroxyandrost-4-en-3-one 2. Oppenauer oxidation of 2 oxidizes the 17β-alcohol in the presence of the hindered 11β-hydroxyl group to yield 11β-hydroxyandrost-4-en-3,17-dione, 3. Migration of the double bond out of conjunction by treatment with potassium t-butoxide followed by protonation with acetic acid yields 11β-hydroxyandrost-5-en-3,17-dione 4. Selective reduction of 4 yields 3β,11β-dihydroxyandrost-5-en-17-one, 5.

HYDROXYLATION AT CARBON-16

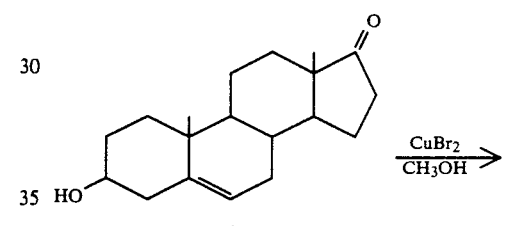

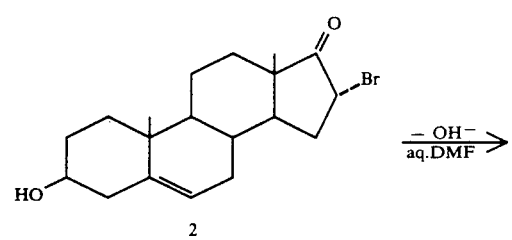

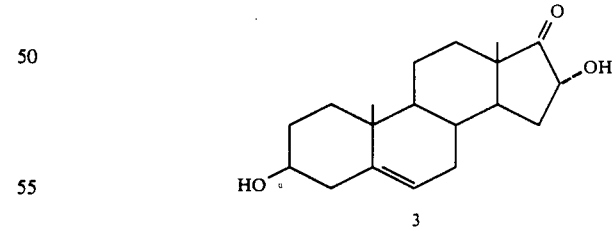

Bromination of DHEA (1) with cupric bromide yields 16α-bromo-DHEA, 2. Treatment of the bromo ketone 2 with sodium hydroxide in aqueous dimethylformamide gave 3β,16α-dihydroxyandrost-5-en-17-one, 3. See M. Numazawa, M. Nagaoka, Y. Osawa, J. Org. Chem. 1982, 47, 4024.

The following procedures are representative of procedures for halogenation at Carbon-1, 2, 3, 4, 6, 7, 11 or 16.

HALOGENATION AT CARBON-1

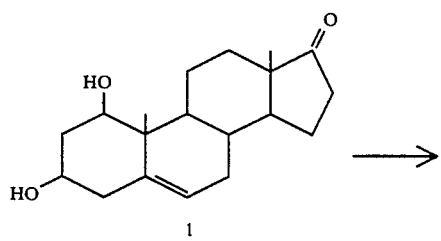

1

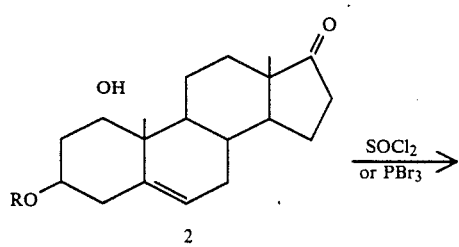

2

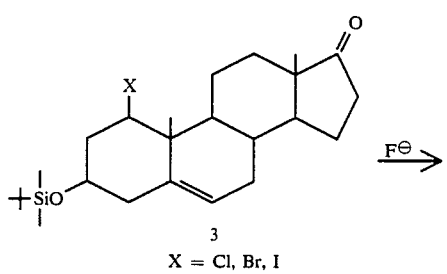

3
X = Cl, Br, I

Selective protection of the Carbon-3 hydroxyl in the presence of the 1α-hydroxyl group should yield 2. For example, 1α,3β-dihydroxyandrost-5-en-17-one 1 reacts with t-butyl-dimethyl silyl chloride in the presence of imidazole using dimethylformamide as a solvent to yield 1α,3β-dihydroxyandrost-5-en-17-one 3t-butyl-dimethylsilyl ether, 2. Reaction of 2 with thionyl chloride, or phosphorous tribromide or catechol phosphochloridate followed by iodine yields the corresponding 1β-chloro, bromo or iodo derivatives 3. Reaction of 3 (R=Cl, Br, I) with tetrabutyl ammonium fluoride yields 1β-halo-3β-hydroxy androst 5-en-17-one, 4 (R=Cl, Br or I). The fluoride (4, R=F) may be synthesized via a similar route using an ester as the protecting group at C-3 and reacting the 1α-hydroxyl group with diethyl (2-chloro-1,1,2-trifluoroethyl)amine. Hydrolysis should yield 1,β-fluoro-3β-hydroxyandrost-5-en-17-one, 4, R=F.

HALOGENATION AT CARBON-2

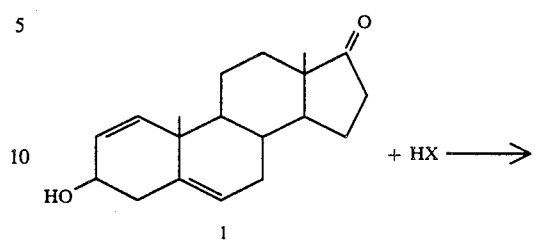

1

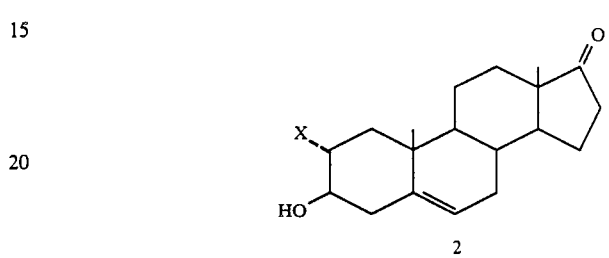

2

Addition of HX across the C-1 double bond in 3β-hydroxyandrosta-1,5-diene-17-one, 1, yields a mixture of the C-1 and C-2 halogenated steroids. Separation affords 2-halo-3β-hydroxyandrost-5-en-17-one (2, R=F, Cl, Br, I).

HALOGENATION AT CARBON-3

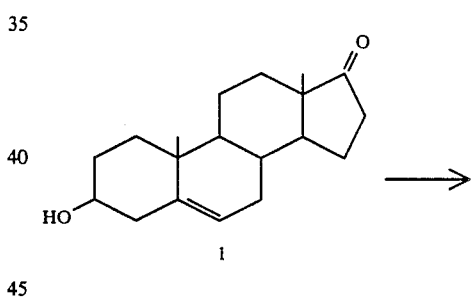

1

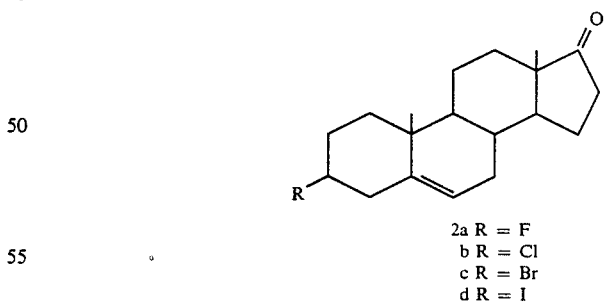

2a R = F
b R = Cl
c R = Br
d R = I

Reaction of 3β-hydroxyandrost-5-en-17-one 1 with diethyl (2-chloro-1,1,2-trifluoroethyl) amine yields 3β-fluoroandrost-5-en-17-one 1. Reaction of 1 with thionyl chloride yields 3β-chloroandrost-5-en-17-one, 2b. Reaction of 1 with phosphorus tribromide yields 3β-bromoandrost-5-en-17-one, 2c. Reaction of 1 with catechol phosphochloridate followed by iodine yields 3β-iodoandrost-5-en-17-one 2d.

HALOGENATION AT CARBON-4

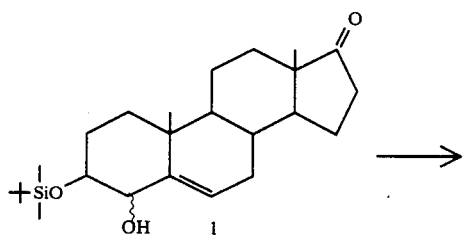

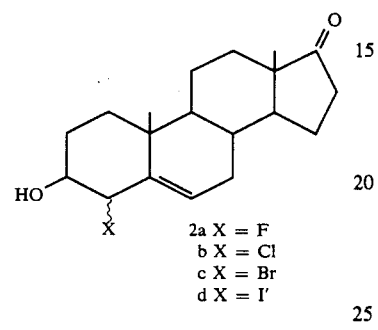

2a X = F
b X = Cl
c X = Br
d X = I'

With the 3β-hydroxyl group protected as its t-butyldimethylsilyl ether the C-4 hydroxyl may be chlorinated using thionyl chloride. Treatment with fluoride ion cleaves the silyl ether to yield 4ξchloro-3β-hydroxyandrost-5-en-17-one, 2b. Reaction of 3,4-dihydroxyandrost-5-en-17-one 3-t-butyldimethylsilyl ether 1 with O-phenylene phosphochloridite, followed by displacement with bromide ion and cleavage of the silyl ether with fluoride ion yields 4ξbromo-3β-hydroxyandrost-5-en-17-one, 2c. Reaction of 1 with catechol phosphochloridate, followed by iodine and cleavage of the silyl ether with fluoride yields 4ξiodo-3β-hydroxyandrost-5-en-17-one, 2d. Fluorination of 3β,4ξdihydroxyandrost-5-en-17-one 3-acetate with diethyl (2-chloro-1,1,2-trifluoroethyl) amine followed by hydrolysis of the ester yields 4ξfluoro-3β-hydroxyandrost-5-en-17-one, 2a.

HALOGENATION AT CARBON-6

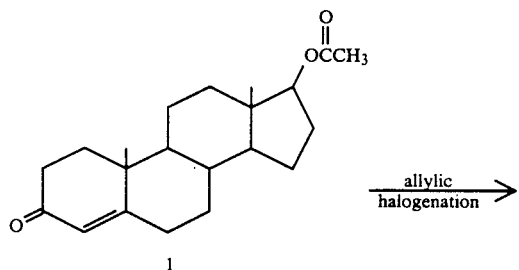

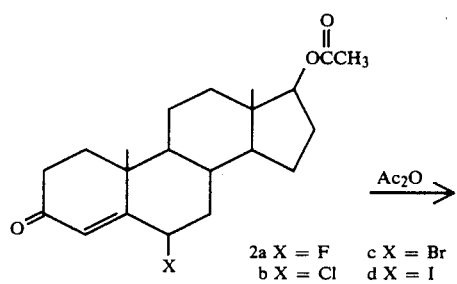

2a X = F    c X = Br
b X = Cl    d X = I

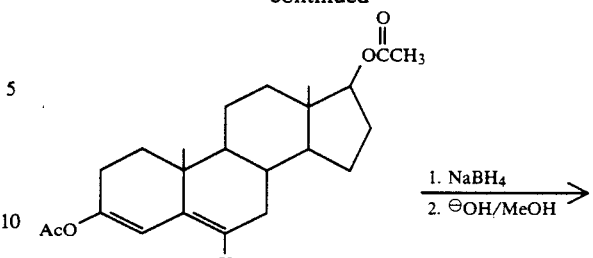

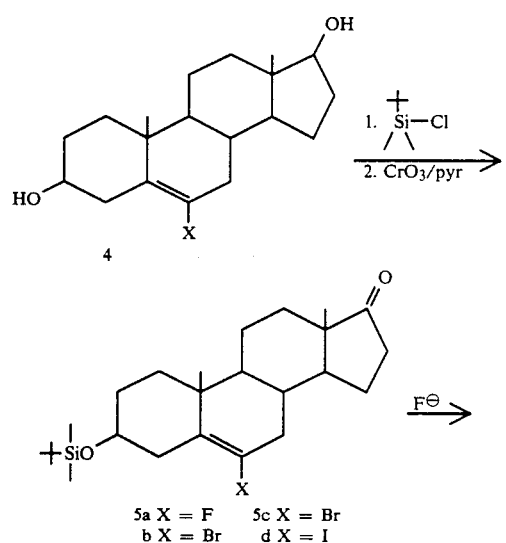

5a X = F    5c X = Br
b X = Br    d X = I

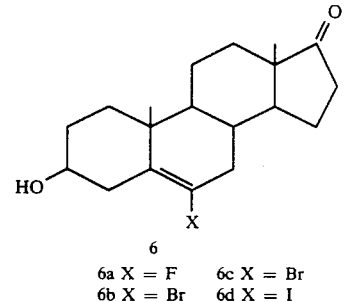

6a X = F    6c X = Br
6b X = Br   6d X = I

Allylic bromination of 17β-hydroxyandrost-4-en-3-one 17-acetate 1 using N-bromosuccinimide together with a radical initiator such as light or benzoyl peroxides or aliphatic azo compounds [RR'C(CN)—N=N—C(CN) RR'] e.g. azobisisobutyronitrile yields 6β-bromo-17β-hydroxyandrost-4-en-3-one 17-acetate, 2. Allylic chlorination of 1 using sulfuryl chloride together with a radical initiator such as light or benzoyl peroxide or aliphatic azo compounds yields 6β-chloro-17β-hydroxyandrost-4-en-3-one 17-acetate, 2c. Allylic iodination of 1 using mercuric iodide and light yields 6β-iodo-17β-hydroxyandrost-4-en-3-one-17-acetate, 2d. Acetylation of 2 with acetic anhydride and p-toluene sulfonic acid in toluene yields 6-halo-3,17β-dihydroxyandrosta-3,5-diene 3,17-diacetate 3. Sodium borohydride reduction of 3 followed by basic hydrolysis of the C-17 acetate yields 6-haloandrost-5-en-3β,17β-diol, 4. Selective protection of the C-3 hydroxyl group as its t-butyldimethylsilyl ether followed by chromium trioxide oxidation of the C-17-hydroxyl group yields 6-halo-3β-hydroxyandrost-5-en-17-one 3-t-butyldimethylsilyl ether 5. Treatment of 5 with fluoride ion yields 6-halo-3β-hydroxyandrost-5-en-17-one, 6. The C-6 fluoro analogue may be synthesized from the C-6 bromo diacetate, 3c, by treatment with silver fluoride. Following the above sequence, reaction of 6-fuloro-3,17β-dihydroxyandrosta-3,5-diene-3,17-diacetate, 3a with sodium borohydride yields, 6-fluoro-3β-hydroxyandrost-5-en-17-one, 6a.

HALOGENATION AT CARBON-7

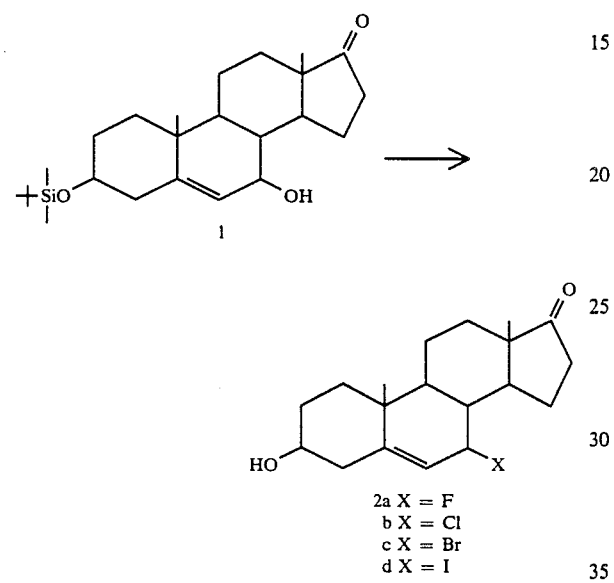

2a X = F
b X = Cl
c X = Br
d X = I

Reaction of 3β,7-dihydroxyandrost-5-en-17-one-3-t-butyldimethylsilyl ether 1 with thionyl chloride yields the C-7 chloro-steroid. Deprotection of the 3β-hydroxyl group affords 7-chloro-3β-hydroxyandrost-5-en-17-one, 2b. Reaction of 1 with catechol phosphochloridate followed by displacement with bromide ion and deprotection yields 7-bromo-3β-hydroxyandrost-5-en-17-one, 2c. Similarly reaction of 1 with catechol phosphochloridate followed by displacement with iodine and deprotection yields 7-iodo-3β-hydroxyandrost-5-en-17-one, 2d. Fluorination of 3β,7-dihydroxyandrost-5-en-17-one 3-acetate with diethyl (2-chloro-1,1,2-trifluoro-ethyl) amine followed by hydrolysis of the ester yields 7-fluoro-3β-hydroxyandrost-5-en-17-one, 2a.

Halogenation at Carbon-9

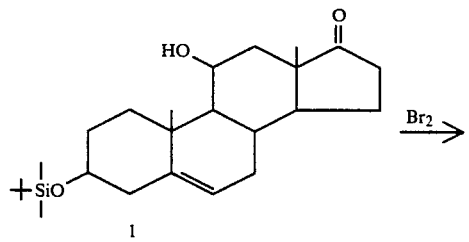

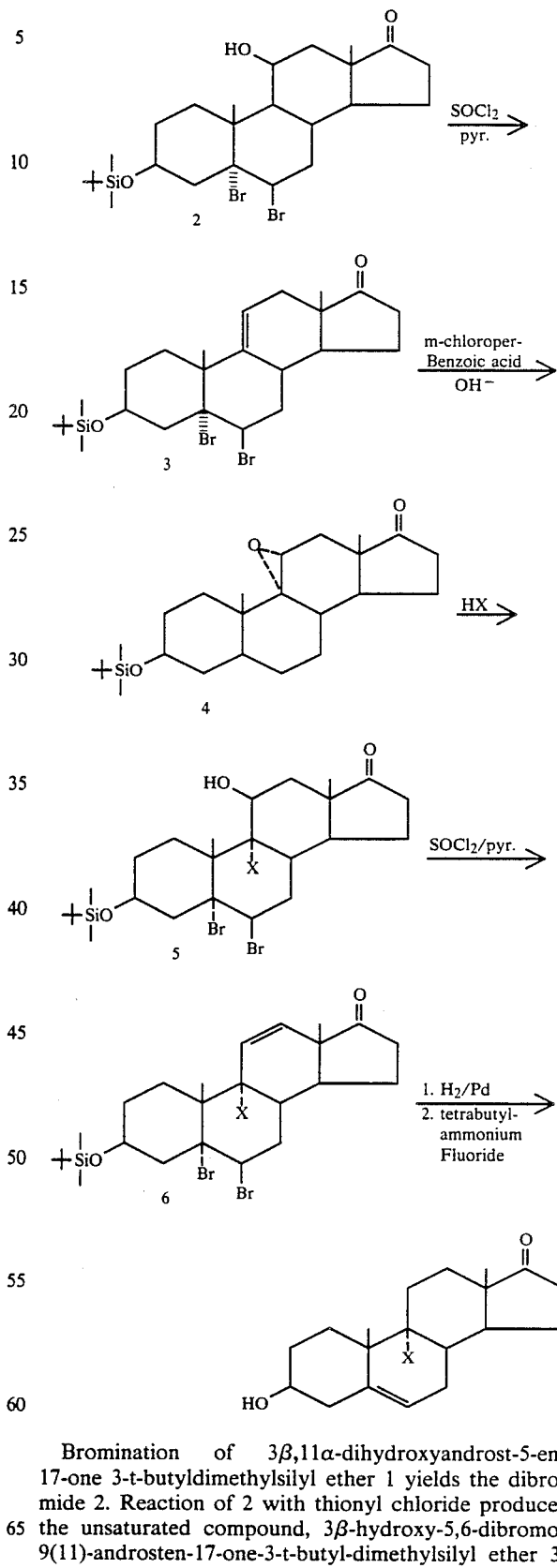

Bromination of 3β,11α-dihydroxyandrost-5-en-17-one 3-t-butyldimethylsilyl ether 1 yields the dibromide 2. Reaction of 2 with thionyl chloride produces the unsaturated compound, 3β-hydroxy-5,6-dibromo-9(11)-androsten-17-one-3-t-butyl-dimethylsilyl ether 3. 3 is epoxidized with perbenzoic acid forming 4. Reaction of 4 with hydrohalic acid, such as HCl, HBr, forms the 9α-halo derivative 5. Dehydration of 5 with thionyl chloride produces the unsaturated compound, the 3β-hydroxy-5,6-dibromo-11-androsten-17-one-3-t-butyldimethylsilyl ether 6. Catalytic hydrogenation of 6 followed by removal of the protecting group forms the 3-βhydroxy-9-α-halo-5-androsten-17-one (1).

HALOGENATION AT CARBON-11

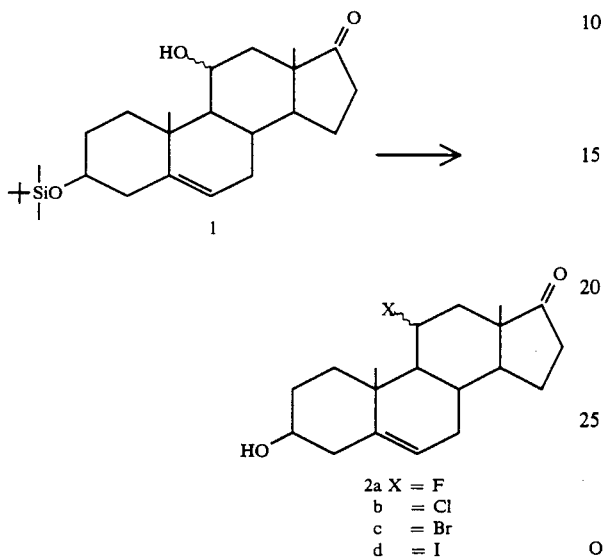

2a X = F
b = Cl
c = Br
d = I

Reaction of 3β,11α-dihydroxyandrost-5-en-17-one 3-t-butyldimethylsilyl ether 1 with OPPC followed by chloride yields the C-11 chloro steroid. Deprotection of the 3β-hydroxyl group affords 11ξ-chloro-3β-hydroxyandrost-5-en-17-one, 2b. Reaction of 1 with OPPC followed by displacement with bromide ion and deprotection yields 11ξ-bromo-3β-hydroxy-androst-5-en-17-one, 2c. Similarly reaction of 1 with OPPC followed by displacement with iodine and deprotection yields 11ξ-iodo-3β, hydroxyandrost-5-en-17-one 2d. Fluorination of 3β,11α-dihydroxyandrost-5-en-17-one 3-acetate with diethyl (2-chloro-1,1,2-trifluoroethyl)amine followed by hydrolysis of the ester yields 11ξ-fluoro-3β-hydroxy-androst-5-en-17-one, 2a.

HALOGENATION AT CARBON-16

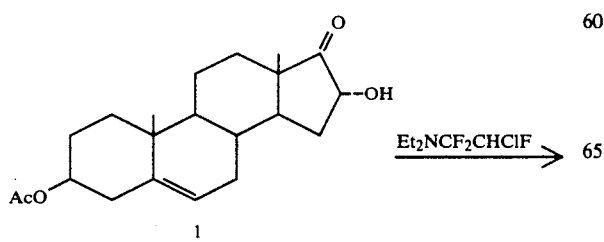

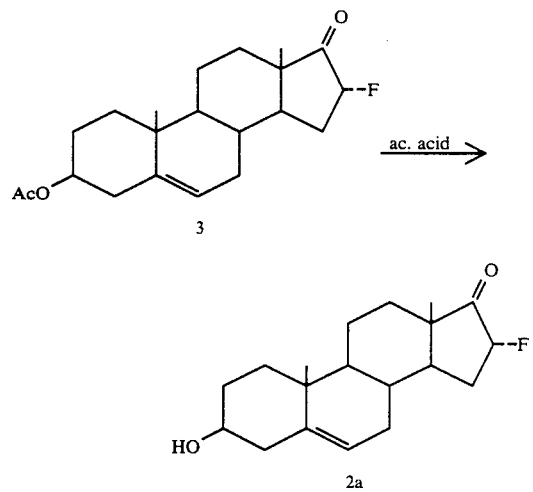

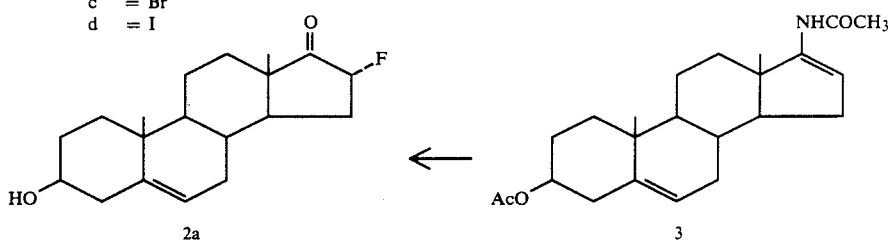

Reaction of 3β,16α-dihydroxyandrost-5-en-17-one 3β-acetate 1 with a fluorinating agent such as diethyl (2-chloro-1,1,2-trifluoroethyl)amine affords 16α-fluoro-3β-hydroxyandrost-5-en-17-one 3-acetate 3. Hydrolysis of the ester with aqueous acid yields 16α-fluoro-3β-hydroxyandrost-5-en-17-one 2a.

Alternatively, 2a could be prepared by treating an enamide, e.g., the enamide of Formula 3 with a fluorinating agent, such as perchloryl fluoride. Hydrolysis of the fluoro enamide acetate with aqueous acid gives 2a.

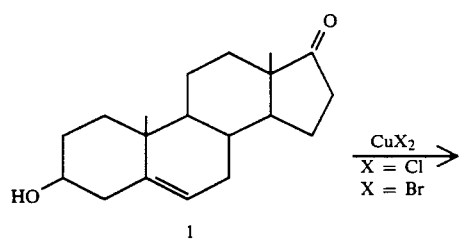

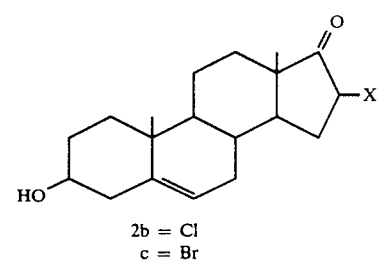

2b = Cl
c = Br

Reaction of 3β-hydroxyandrost-5-en-17-one 1 with cupric bromide yields 16α-bromo-3βhydroxyandrost-5- en-17-one, 2c[1]. Similarly, reaction of 1 with cupric chloride yields 16α-chloro-3β-hydroxyandrost-5-en-17-one, 2b[2].

[1] E. R. Glazier J. Org. Chem. 1962, 27, 4397
[2] E. M. Kosower, et al., J. Org. Chem. (1963), 28, 630

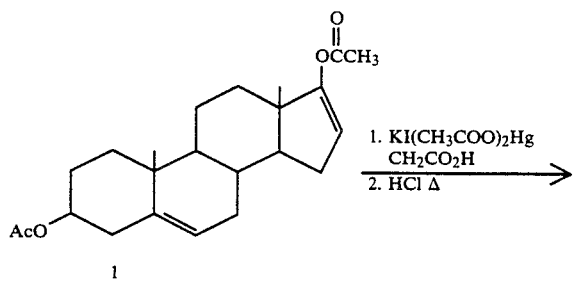

1

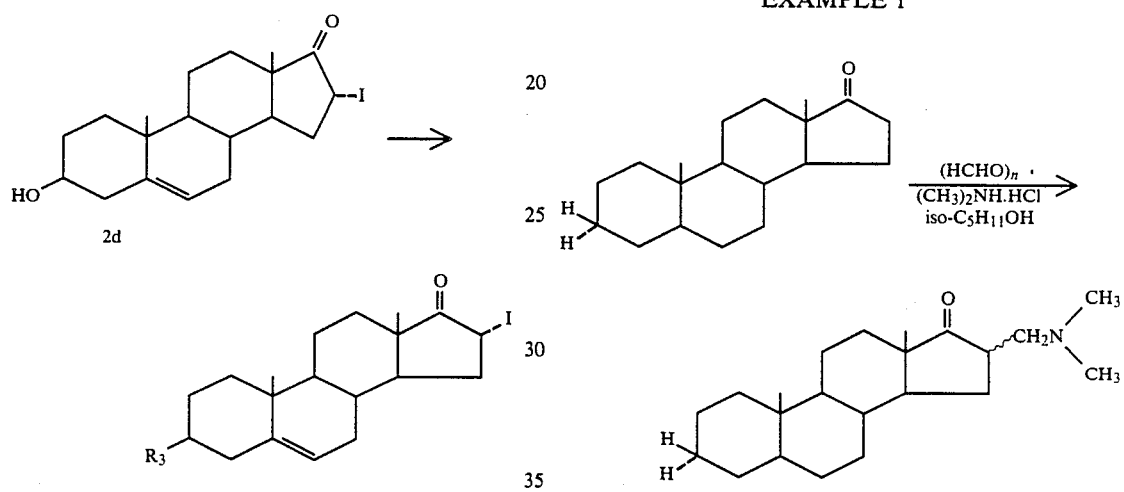

2d

Reaction of 3β,17-dihydroxyandrosta-5,16-diene 17-acetate 1 with mercuric acetate followed by treatment with potassium iodide yields the C-16αiodide which hydrolyses with acid to yield 3β-hydroxy-16α-iodoandrost-5-en-17-one, 2d. Reaction of 2d with silver fluoride yields 3β-hydroxy-16α-fluoroandrost-5-en-17-one, 2a.

Alternatively, 2d can be formed from the reaction of 1 with N-iodo-succinimide. In addition, the reaction of 2c with NaI/acetone overnight results in a mixture of 16α and 16βI-3β-hydroxy-5-androsten-17-ones.

ALKOXYLATION

The alkoxy groups at the various positions denoted $R_1$–$R_{15}$ in FIGS. I and II are derived from the corresponding alcohols and are prepared in a similar manner to the 16-alkoxylations discussed hereinabove. The methoxy substituent for example is formed by reacting the corresponding alcohol in methylene chloride with boron trifluoride and etheral diazomethane according to the procedure of Caserio, et al., JACS, 80, 2584 (1958). Similarly, the ethoxy substituent is formed by reacting the corresponding alcohol in methylene chloride with boron trifluoride and etheral diazoethane, generated in situ. Alternatively, the alkoxy substituents can also be added to the steroid ring by reacting the alcohol under Williamson reaction conditions with RX, where X is an organic leaving group such as halide tosylate or mesylate and R is loweralkyl. Any base normally employed to deprotonate an alcohol may be used, such as sodium hydride, sodium amide, sodium, sodium hydroxide, triethylamino or disopropyl ethylamine. Reaction temperatures are in the range of −78° C. to reflux. The reaction is carried out in a solvent that will dissolve both reactants and is inert to both reactants and products as well. Solvents include, but are not limited to, diethyl ether, tetrahydrofuran, N,N-dimethylformamide, methylene chloride, and the like.

The ketone should be protected with protecting groups known in the art. Examples of many of the possible protecting groups that may be utilized are found in "Protective Groups in Organic Synthesis," by T. W. Green, John Wiley and Sons, 1981. For example, the ketone may be protected as the ethyleneketal.

The following examples further illustrate the invention:

EXAMPLE 1

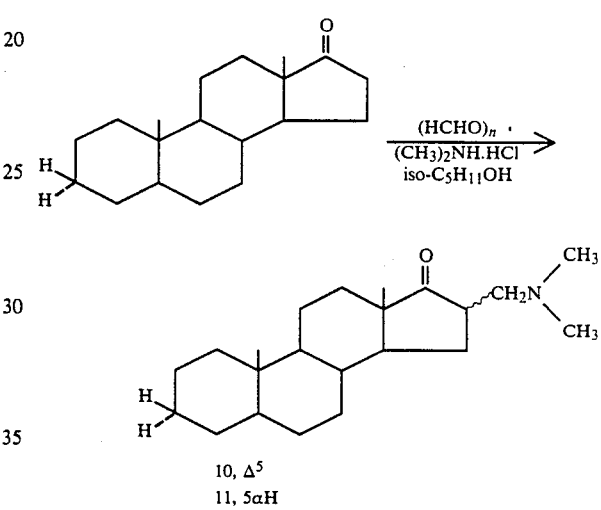

10, Δ⁵
11, 5αH

16-Dimethylamino methyl-17-ones 10 and 11 (See Julian, et al., JACS, 70, 3872, 1948)

Condensation of the 17-one with dimethylamine hydrochloride and paraformaldehyde in isoamyl alcohol yields the Mannich bases 10 and 11.

EXAMPLE 2

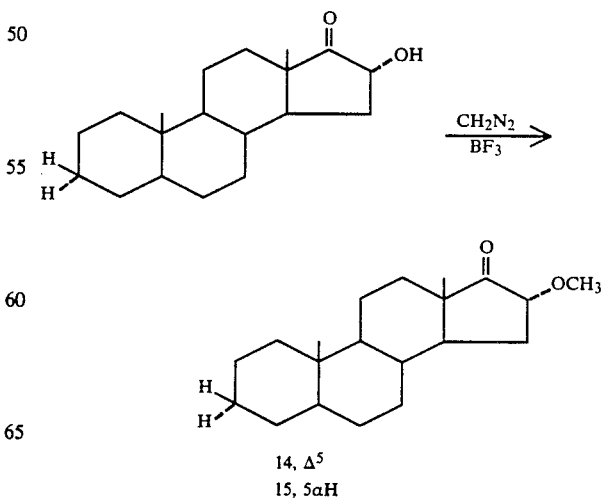

14, Δ⁵
15, 5αH

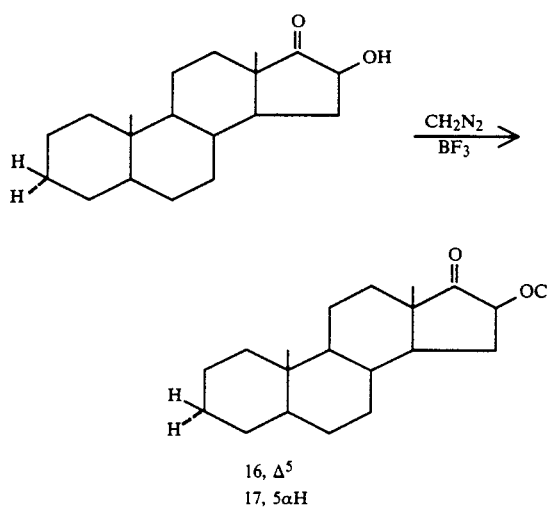

16α- and 16β-Methoxy-5-Androsten-17-ones (14, 16) and 16α- and 16β-Methoxy-5α-Androstan-17-ones (15, 17)

Treatment of the appropriate 16α- or 16β-ol in methylene chloride with borontrifluoride and ethereal diazomethane by the procedure of Caserio, et al., JACS 80, 2584, 1958, affords the corresponding methyl ethers.

EXAMPLE 3

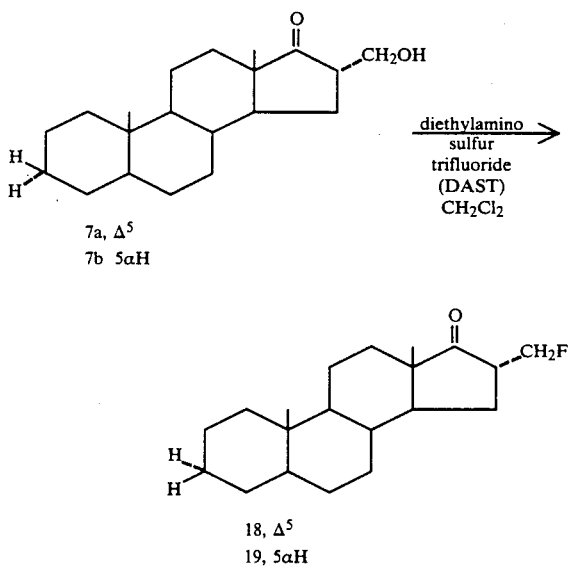

16α-Fluoromethyl-5-Androsten-17-one (18) and 16α-Fluoromethyl-5α-Androstan-17-one (19)

Treatment of 16α-hydroxymethyl-5-androsten-17-one (7a) in methylene chloride with DAST at 5° affords the alkyl fluoride 18. Similar treatment of 16α-hydroxymethyl-5α-androstan-17-one (7b) or catalytic hydrogenation of 18 furnishes 19.

EXAMPLE 4

A. Formation of 16-methylene 17-ones

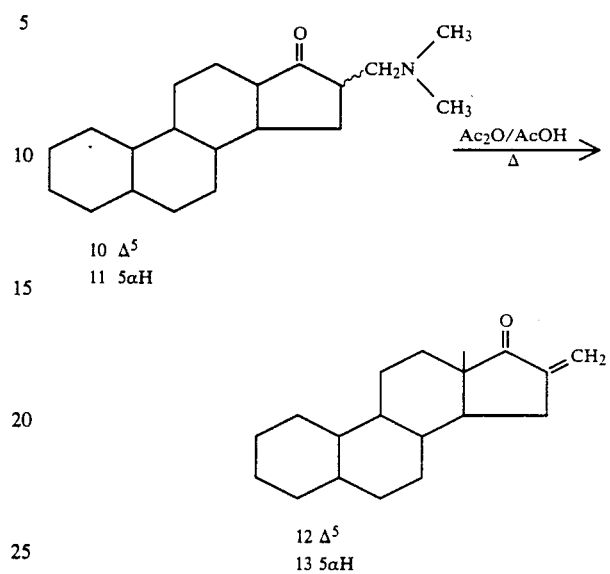

The 16 dimethylaminomethyl substituent 10 and 11, prepared in Example 1 is heated with a 1:1 solution of acetic acid to form the corresponding 16 methylene derivative 12($\Delta^5$) and 13(5αH).

B.

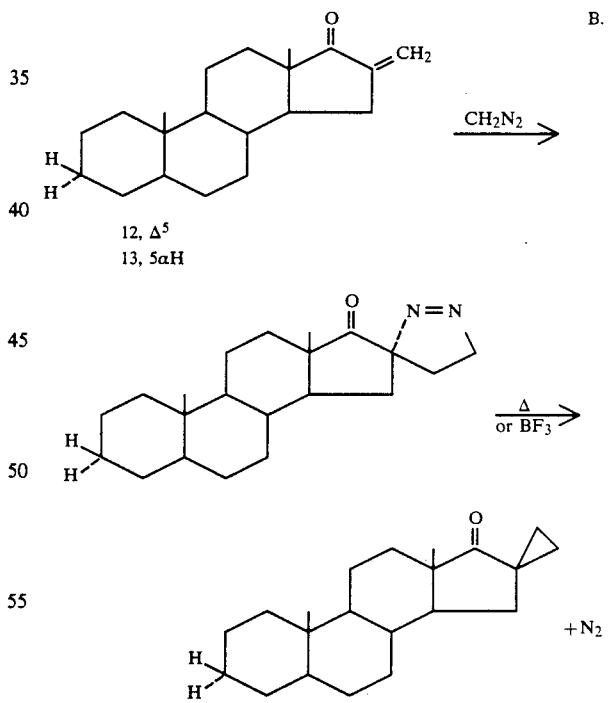

B. 16-Cyclopropyl-5-Androsten-17-one (22) and 16-Cyclopropyl-5α-Androstan-17-one (23)

Treatment of the appropriate 16-methylene compound (12 or 13) with diazomethane yields the spiropyrazoline derivatives [see Bruckner, et al., Chem.

Ber. 94, 2897 (1961)]. Pyrolysis of the spiro-pyrazoline intermediates or cleavage in the presence of boron trifluoride etherate affords the 16-spirocyclopropyl steroids 22 and 23.

C. 16-cyclobutyl-5-Androsten-17-one (24) and 16-cyclobutyl 5α-Androstan-17-one (25)

Similarly by following the procedure of B and substituting diazoethane for diazomethane, the above products are prepared.

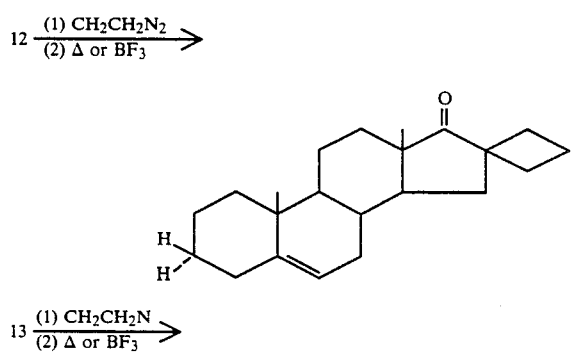

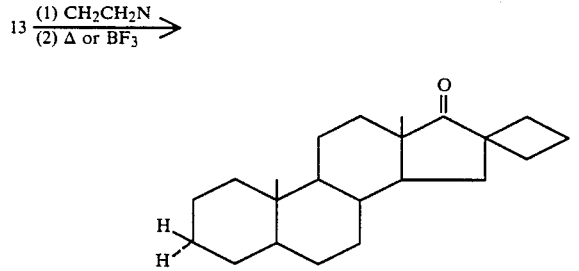

EXAMPLE 5

16-Hydroxymethylene-5-Androsten-17-one (5) and 16-Hydroxymethylene-5α-Androstan-17-one (6)

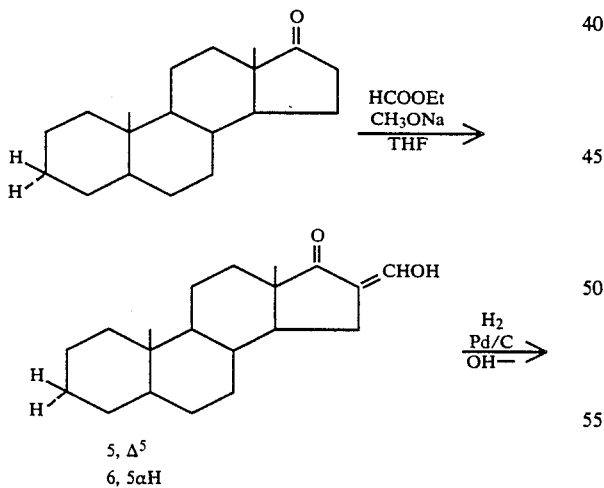

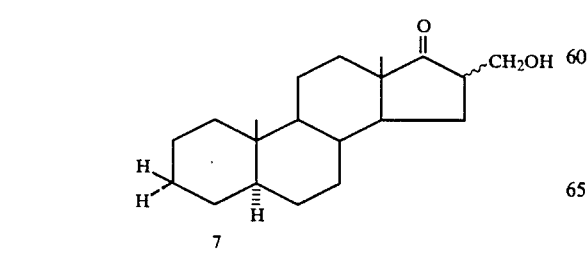

Formylation of the 17-ones by the procedure of C. H. Robinson, et al., J. Org. Chem., 28, 975, 1963, gives the 16-hydroxy-methylenes.

Catalytic hydrogenation in aqueous alkoxide of either 5 or 6 gives the hydroxymethyl 17-one 7.

EXAMPLE 6

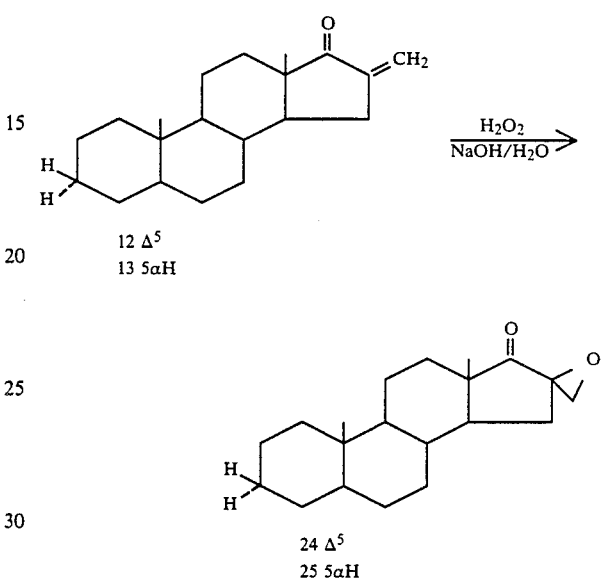

Treatment of the appropriate 16 methylene compound (12) or (13) (prepared as in Example 1) in an alkaline solution of hydrogen peroxide affords the 16-oxymethylene derivatives (24) or (25).

EXAMPLE 7

See Tetrahedron Letters, No. 42, pp 4071–4072 (1979).

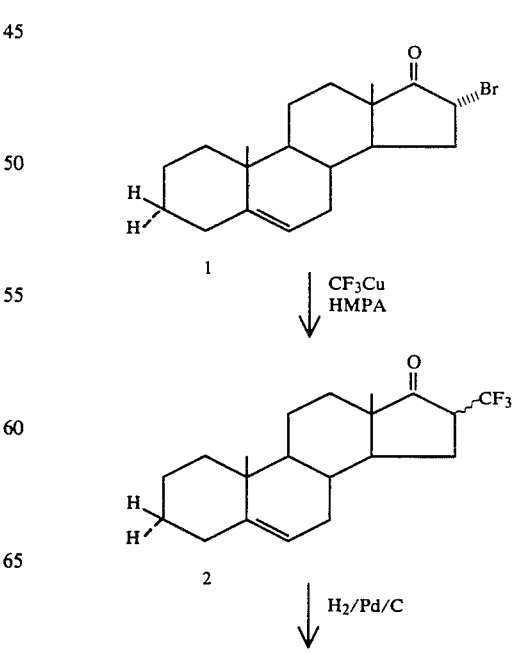

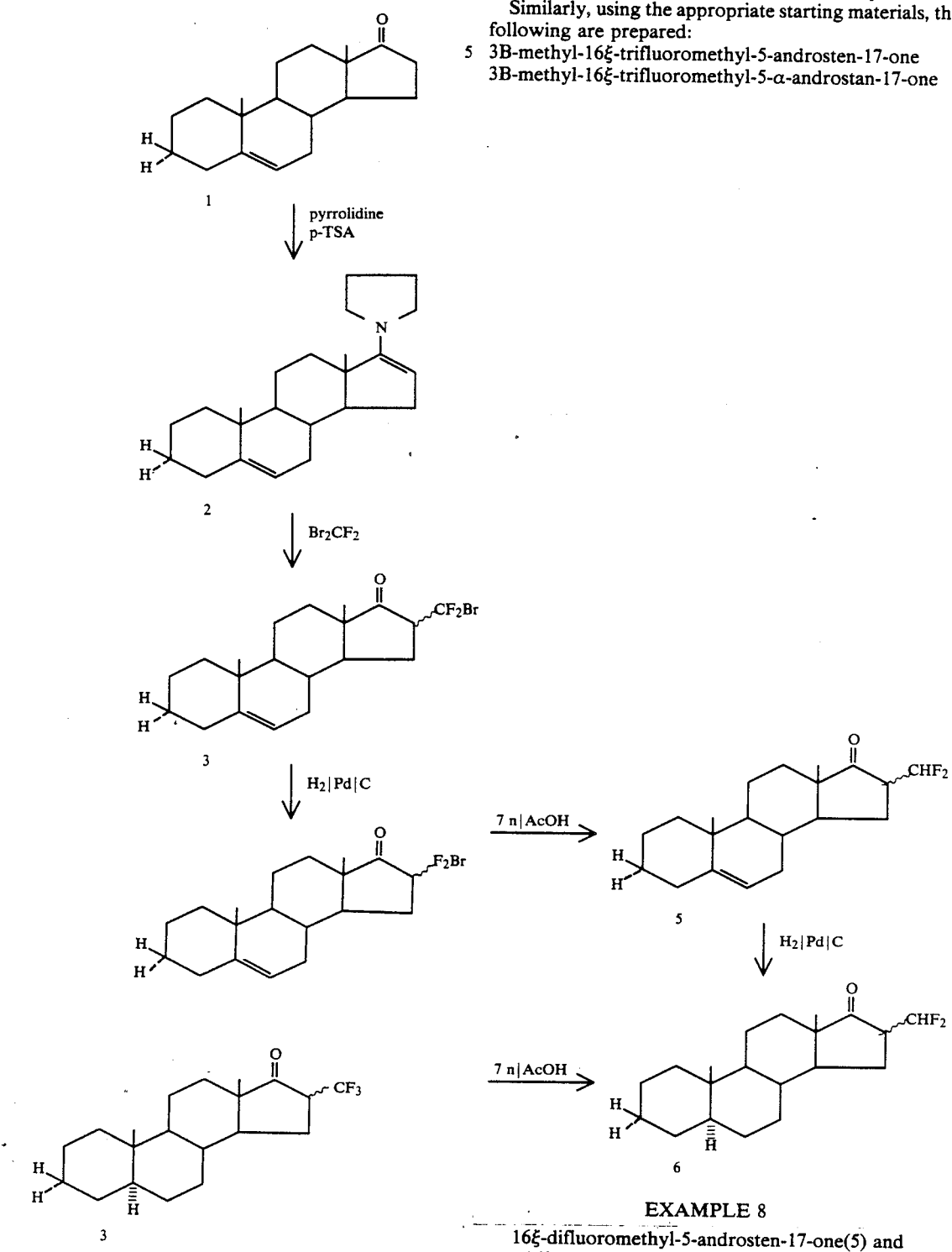

affords 2 in good yield catalytic hydrogenation of 2 in ethanol with 5% Pd on C gives the saturated product, 3.

Similarly, using the appropriate starting materials, the following are prepared:

3B-methyl-16ξ-trifluoromethyl-5-androsten-17-one
3B-methyl-16ξ-trifluoromethyl-5-α-androstan-17-one 16ξ-trifluoromethyl-5-androsten-17-one(2) and
16ξ-trifluoromethyl-5-α-androstan-17-one(3)

Treatment of 16ξ-bromo505androsten-17-one(1) with trifluoromethyl copper (prepared by heating trifluoromethyl iodide and copper powder in hexomethyl phosphoramide in a sealed stainless steel tube at 120° for 2.5 h) at 70° under nitrogen according to the procedure by Kobayashi, et al. in *Tetrahedron Letters,* 42, 4071 (1979)

EXAMPLE 8

16ξ-difluoromethyl-5-androsten-17-one(5) and
16ξ-difluoromethyl-5α-androsten-17-one(6)

Conversion of 5-androsten-17-one(1) to the enamine (2) is accomplished by reaction with pyrrolidine containing a catalytic amount of p-toluene sulfonic acid. Reaction of 2 with dibromodifluoromethane in pentane solution affords after hydrolysis the 16-bromodifluoromethyl product, 3. Reaction of 3 with zinc dust in acetic acid gives the 16ξ-difluoromethyl-17-one 5. Catalytic hydrogenation of 5 affords the saturated bromodifluoromethyl-17-one,4. Zinc/acetic acid treatment of 4 gives the 16ξ-difluoromethyl-17-one, 6. Alternatively, 6 can be prepared from 5 by catalytic hydrogenation.

Similarly, using the appropriate starting materials, the following are prepared:
3B-methyl-16ξ-difluoromethyl-5-androsten-17-one
3B-methyl-16ξdifluoromethyl-5α-androstan-17-one

EXAMPLE 9

16-carbomethoxy-5-androsten-17-one 5 androsten-17-one is reacted with cupric bromide according to the procedure of E. R. Glazier, J. Organic Chem, 1962, 27, 4397 to form the 16-bromo-5-androsten-17-one. The 16-bromo product, ethylene glycol and P-toluene sulfonic acid in benzene is then refluxed under a Dean Stark trap for 72 hours. The resulting product is washed with saturated sodium bicarbonate, water and then dried over magnesium sulfate. Evaporation affords the 16-bromo-5-andtostene-17-one-17-ethylene ketal. The resulting product is then disolved in THF and magnesium turnings are added to form the corresponding grignard reagent. Dry ice is added to the grignard reagent. Acid work-up affords the 16-carboxy-5-androsten-17-one. Fischer esterification with P-toluene-sulfonic acid in methanol affords the above-identified product.

Similarly, using the appropriate starting materials the following compounds are also forms:
16-carbomethoxy-5-androstan-17-one
3β-methyl-16-carbomethoxy-5-androsten-17-one
3β-methyl-16-carbomethoxy-5-androstan-17-one

EXAMPLE 10

Using the procedures described herein and the appropriate starting materials, the following compounds are formed:

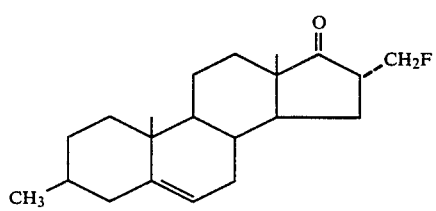

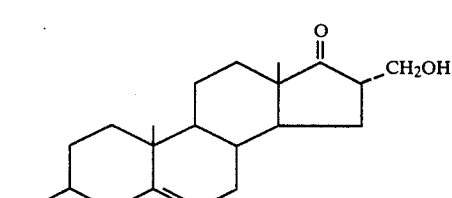

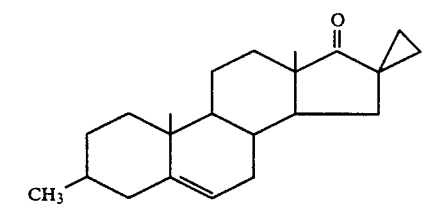

-continued

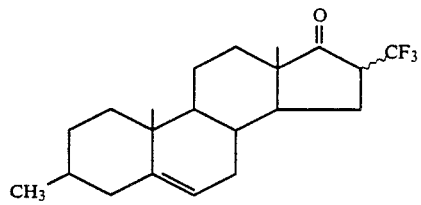

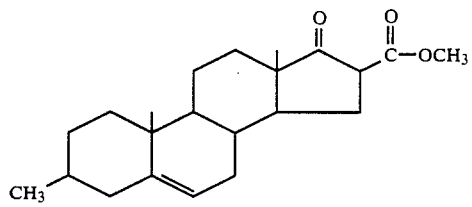

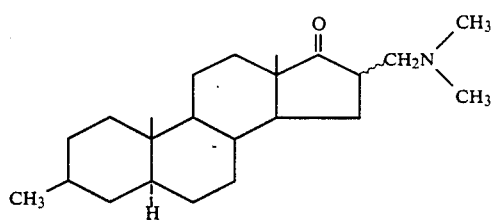

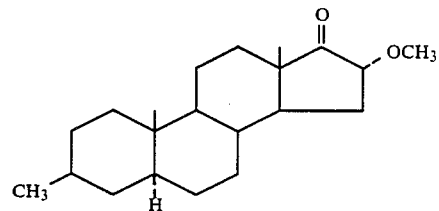

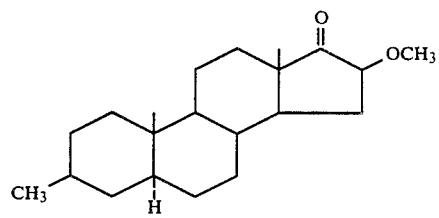

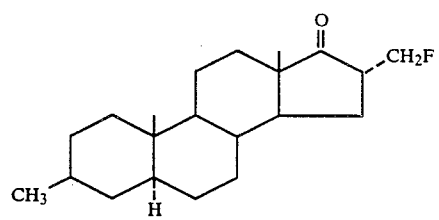

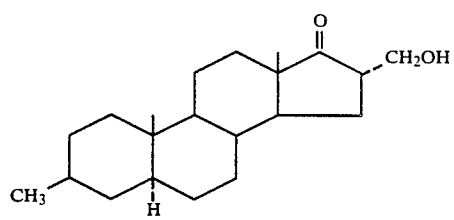

-continued

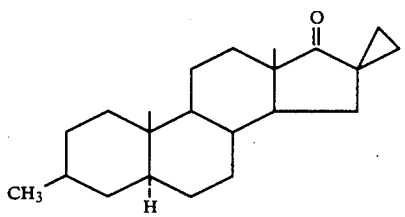

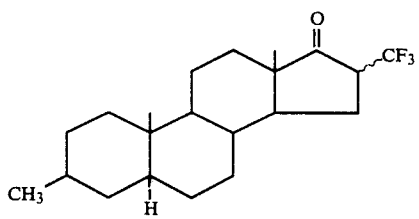

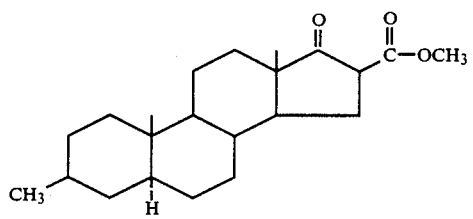

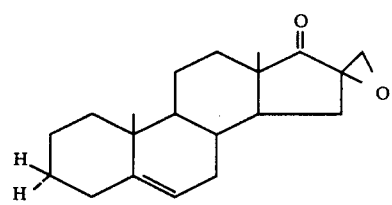

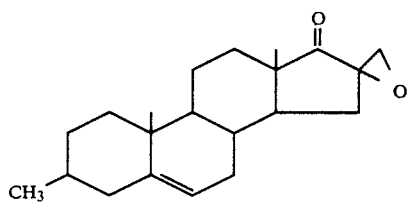

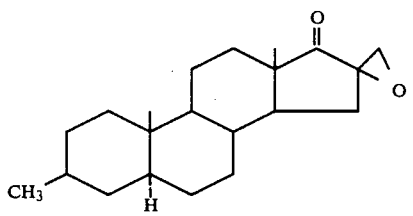

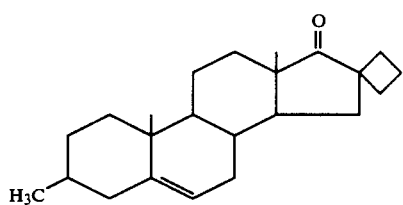

-continued

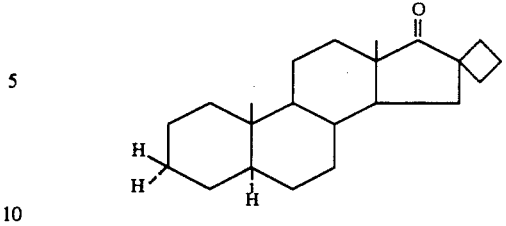

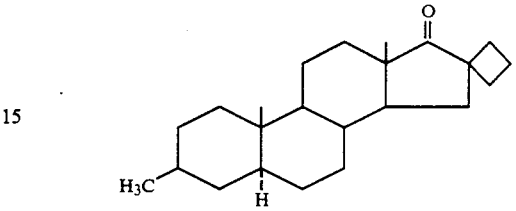

A compound's efficacy in the inhibition of mammalian glucose 6-phosphate dehydrogenase (G6 PDH inhibition) is an accurate indicator of its cancer prophylatic activity. The assay for testing the inhibition of purified bovine adrenal G6PDH is described by Oertel, G. W. and Rebebun, F., in *Biochem. Biophys. Acta*, 184, 459–460 (1969).

The results of representative compounds are shown below:

| Compound | Conc | Percent G6PDH Inhibition |
|---|---|---|
| DHEA | $10^{-5}M$ | 54, 51 |
|  | $10^{-6}M$ | 24, 20 |
| 16α-Methoxy-5α-androstan-17-one | $10^{-5}M$ | 58, 58 |
|  | $10^{-6}M$ | 28, 29 |

Compounds of the present invention are both effective as in the prophylaxis and treatment of cancer. It has been shown that compounds of this sort are effective inhibitors of G6PDH dehydrogenase.

Compounds of the present invention are also effective in the prophylaxis and treatment of obesity. In fact, the compounds wherein the B ring of the steroid contains a double bond in the 5,6 position are more effective with respect to anti-obesity than the saturated counterpart, which has some effectiveness in the obesity test. On the other hand, the saturated couterparts are more effective in the anti-cancer tests than are the unsaturated steroids containing a double bond in the 5,6 position, which by the way also exhibit anti-cancer activity. Therefore, the anti-cancer effect and the anti-obesity effect can be separated out. As a result, the physician can prescribe drugs wherein he can emphasize one effect relative to the other.

The compounds of the present invention are also effective anti-hyperglycemic agents, anti-hypercholesterolemic agents and anti-aging agents, both with respect to the prophylaxis and treatment of the aforesaid diseases, conditions or disorders. Moreover, the compounds of the present invention are effective anti-auto-immune agents, and are effective in the prophylaxis and treatment of auto-immune diseases such as lupus erythematosis and Coomb's positive hemolytic anemia.

The compounds of the present invention do not possess the side effects that are exhibited by other steroids. Unlike other steroids such as DHEA, the compounds of the present invention do not exhibit an estrogen effect.

Furthermore, the compounds of the present invention do not exhibit liver enlargement, which is prevalent with other steroids, such as DHEA.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. For parental administration they may be used in the form of a sterile solution containing other solutes, for example, enough saline or glucose to make the solution isotomic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages, substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with those other therapeutic agents.

When given orally, the therapeutic doses of the compounds of the present invention are generally in the range of from about 4 to about 450 mg/kg/day depending upon the particular mammalian host and the particular effect desired, e.g. cancer preventive, anti-obesity, anti-diabetes, etc. When given parenterally, the compounds are administered generally in dosages of, for example, 0.5 to about 15 mg/kg/day, also depending upon the host and effect desired.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A compound of the formula:

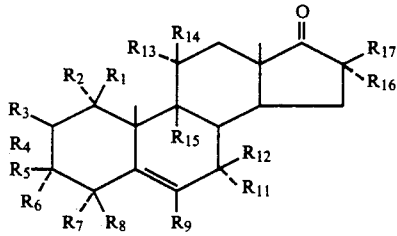

wherein $R_1$, $R_2$, $R_3$, $R_4$, $R_7$, $R_8$, $R_{11}$, $R_{12}$, $R_{13}$, $R_{14}$, and $R_{15}$ independently hydrogen, lower alkyl, halogen, hydroxy, or lower alkoxy;

$R_5$ and $R_6$ are independently hydrogen, lower alkyl, halogen, or lower alkoxy;

$R_9$ is hydrogen, lower alkyl or halogen and $R_{16}$ and $R_{17}$ are independently hydrogen, amino, loweralkylamino, diloweralkylamino, aminoloweralkyl, loweralkylamino loweralkyl, diloweralkylaminolower alkyl, loweralkoxyloweralkyl, lower alkoxy, hydroxy lower alkyl, monohaloloweralkyl, dihaloloweralkyl, trihaloloweralkyl, loweralkanoyl, formyl, lower carbalkoxy, or lower alkonoyloxy or $R_{16}$ and $R_{17}$ taken together with the carbons to which they are attached form a lower cycloalkyl or a cyclic ether containing 1 ring oxygen atom and up to 5 ring carbon atoms. with the proviso that $R_{16}$ and $R_{17}$ are not hydrogen simultaneously.

2. The compound according to claim 1 wherein lower alkyl and lower alkoxy groups contain 1-3 carbon atoms.

3. The compound according to claim 1 wherein lower alkyl is methyl.

4. The compound according to claim 1 wherein halogen is fluorine.

5. The compound according to claim 1 wherein $R_5$ is hydrogen or methyl and $R_6$ is hydrogen.

6. The compound according to claim 1 wherein at most one of $R_1$, $R_2$, $R_3$, $R_4$, $R_7$, $R_8$, $R_9$, $R_{11}$, $R_{12}$, $R_{13}$, $R_{14}$ or $R_{15}$ is other than hydrogen.

7. The compound according to claim 1 wherein $R_1$, $R_2$, $R_3$, $R_4$, $R_7$, $R_8$, $R_9$, $R_{11}$, $R_{12}$, $R_{13}$, $R_{14}$ or $R_{15}$ are hydrogen.

8. The compound according to claim 1 wherein $R_{17}$ and $R_{16}$ are independently hydrogen, methoxy, trifluoromethyl, difluoromethyl, monofluoromethyl, hydroxy methyl, dimethylaminomethyl or carbomethoxy or $R_{17}$ and $R_{16}$ taken together with the carbon to which they are attached form a cyclopropyl or an oxirane ring.

9. A compound of the formula:

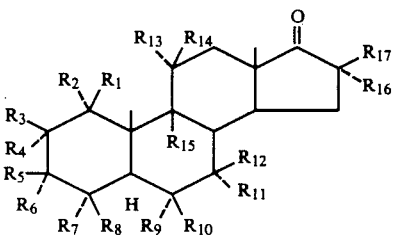

wherein
$R_1$, $R_2$, $R_3$, $R_4$, $R_5$, $R_6$, $R_7$, $R_8$, $R_{11}$, $R_{12}$, $R_{13}$, $R_{14}$ and $R_{15}$ are independently hydrogen, lower alkyl, halogen, hydroxy or lower alkoxy;

$R_9$ and $R_{10}$ are independently lower alkyl, hydrogen or halogen; and $R_{16}$ and $R_{17}$ are independently hydrogen, amino, lower alkylamino, diloweralkyl amino, aminoloweralkyl, loweralkyl, aminoloweralkyl, diloweralkylamino loweralkyl, lower alkoxy, hydroxyloweralkyl, monohaloloweralkyl, dihaloloweralkyl, trihaloloweralkyl, loweralkoxy-loweralkyl, loweralkanoyl, formyl, or lower carbalkoxy; or $R_{16}$ and $R_{17}$ taken together with the carbon to which they are attached form a lower cycloalkyl or a cyclic ether containing 1 ring oxygen atom and up to 5 ring carbon atoms with the proviso that $R_{16}$ and $R_{17}$ are not hydrogen simultaneously and with the further proviso that when $R_1$-$R_{15}$ and $R_{17}$ are hydrogen, then $R_{16}$ is not ethoxy.

10. The compound according to claim 9 wherein lower alkyl and lower alkoxy groups contain 1-3 carbon atoms.

11. The compound according to claim 9 wherein lower alkyl is methyl.

12. The compound according to claim 9 wherein halogen is fluorine.

13. The compound according to claim 9 wherein $R_5$ is hydrogen or methyl and $R_6$ is hydrogen.

14. The compound according to claim 9 wherein at most one of $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ is other than hydrogen.

15. The compound according to claim 9 wherein $R_1$, $R_2$, $R_3$, $R_4$, $R_7$, $R_8$, $R_9$, $R_{10}$, $R_{11}$, $R_{12}$, $R_{13}$, $R_{14}$ or $R_{15}$ are hydrogen.

16. The compound according to claim 9 wherein $R_{16}$ and $R_{17}$ are independently hydrogen, methoxy, trifluoromethyl, difluoromethyl, monofluoromethyl, hydroxy methyl, dimethylaminomethyl or carbomethoxy or $R_{16}$ and $R_{17}$ taken together with the carbon to which they are attached form a cyclopropyl or an oxirane ring.

17. A compound of the formula:

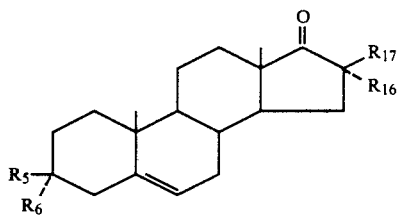

wherein
$R_5$ and $R_6$ are independently lower alkyl or hydrogen; and $R_{16}$ and $R_{17}$ are independently hydrogen, amino, lower alkylamino, diloweralkyl amino, aminoloweralkyl, loweralkyl aminoloweralkyl, diloweralkylamino loweralkyl, lower alkoxy, hydroxyloweralkyl, monohaloloweralkyl, dihaloloweralkyl, trihaloloweralkyl, loweralkoxy-loweralkyl, loweralkanoyl, formyl, lower carbalkoxy or lower alkanoyloxy; or $R_{16}$ and $R_{17}$ taken together with the carbon to which they are attached form a lower cycloalkyl or a cyclic ether containing 1 ring oxygen atom and up to a total of 5 ring carbon atoms with the proviso that $R_{16}$ and $R_{17}$ are not hydrogen simultaneously.

18. The compound according to claim 17 wherein lower alkyl and lower alkoxy groups contain 1-3 carbon atoms.

19. The compound according to claim 17 wherein lower alkyl is methyl.

20. The compound according to claim 17 wherein halogen is fluorine.

21. The compound according to claim 1 wherein $R_5$ is hydrogen or methyl and $R_6$ is hydrogen.

22. The compound according to claim 17 wherein $R_{16}$ and $R_{17}$ are independently hydrogen, methoxy, trifluoromethyl, difluoromethyl, monofluoromethyl, hydroxy methyl, dimethylaminomethyl or carbomethoxy or $R_{16}$ and $R_{17}$ taken together with the carbon to which they are attached form a cyclopropyl or an oxirane ring.

23. A compound of the formula:

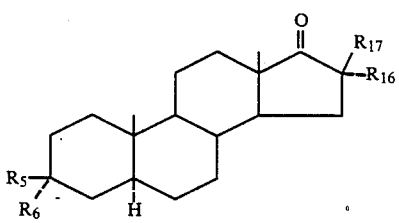

wherein $R_5$ and $R_6$ are independently lower alkyl or hydrogen; and $R_{16}$ and $R_{17}$ are independently hydrogen, amino, lower alkylamino, diloweralkyl amino, aminoloweralkyl, loweralkyl, aminoloweralkyl, diloweralkylamino loweralkyl, lower alkoxy, hydroxyloweralkyl, monohaloloweralkyl, dihaloloweralkyl, trihaloloweralkyl, loweralkoxy-loweralkyl, loweralkanoyl, formyl, lower carbalkoxy; or $R_{16}$ and $R_{17}$ taken together with the carbon to which they are attached form a lower cycloalkyl or a cyclic ether containing 1 ring oxygen atom and up to 5 ring carbon atoms with the proviso that $R_{16}$ and $R_{17}$ are not hydrogen simultaneously and with the further proviso that when $R_1$–$R_{15}$ and $R_{17}$ are hydrogen, then $R_{16}$ is not ethoxy.

24. The compound according to claim 23 wherein lower alkyl and lower alkoxy groups contain 1–3 carbon atoms.

25. The compound according to claim 23 wherein lower alkyl is methyl.

26. The compound according to claim 23 wherein halogen is fluorine.

27. The compound according to claim 23 wherein $R_5$ is hydrogen or methyl and $R_6$ is hydrogen.

28. The compound according to claim 23 wherein $R_{16}$ and $R_{17}$ are independently hydrogen, methoxy, trifluoromethyl, difluoromethyl, monofluoromethyl, hydroxy methyl, dimethylaminomethyl or carbomethoxy or $R_{16}$ and $R_{17}$ taken together with the carbon to which they are attached form a cyclopropyl or an oxirane ring.

29. A compound of the formula:

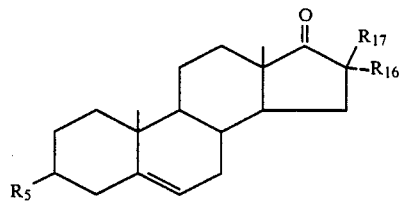

wherein $R_5$ is loweralkyl or hydrogen; and $R_{16}$ and $R_{17}$ are independently hydrogen, amino, lower alkylamino, diloweralkyl amino, aminoloweralkyl, loweralkyl, aminoloweralkyl, diloweralkylamino loweralkyl, lower alkoxy, hydroxyloweralkyl, monohaloloweralkyl, dihaloloweralkyl, trihaloloweralkyl, loweralkoxy-loweralkyl, loweralkanoyl, formyl, lower carbalkoxy or lower alkanoyloxy; or $R_{16}$ and $R_{17}$ taken together with the carbon to which they are attached form a lower cycloalkyl or a cyclic ether containing 1 ring oxygen atom and up to 5 ring carbon atoms with the proviso that $R_{16}$ and $R_{17}$ are not hydrogen simultaneously.

30. The compound according to claim 29 wherein lower alkyl and lower alkoxy groups contain 1–3 carbon atoms.

31. The compound according to claim 29 wherein lower alkyl is methyl.

32. The compound according to claim 29 wherein halogen is fluorine.

33. The compound according to claim 29 wherein $R_5$ is hydrogen or methyl.

34. The compound according to claim 29 wherein $R_{16}$ and $R_{17}$ are independently hydrogen, methoxy, trifluoromethyl, difluoromethyl, monofluoromethyl, hydroxy methyl, dimethylaminomethyl or carbomethoxy or $R_{16}$ and $R_{17}$ taken together with the carbon to which they are attached form a cyclopropyl or an oxirane ring.

35. A compound of the formula:

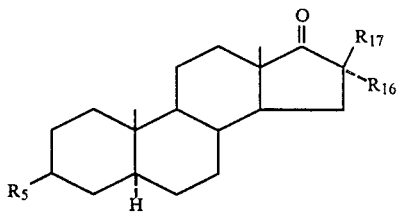

wherein $R_5$ is loweralkyl or hydrogen; and $R_{16}$ and $R_{17}$ are independently hydrogen, amino, lower alkylamino, diloweralkyl amino, aminoloweralkyl, loweralkyl, aminoloweralkyl, diloweralkylamino loweralkyl, lower alkoxy, hydroxyloweralkyl, monohaloloweralkyl, dihaloloweralkyl, trihaloloweralkyl, loweralkoxy-loweralkyl, loweralkanoyl, formyl, or lower carbalkoxy; or $R_{16}$ and $R_{17}$ taken together with the carbon to which they are attached form a lower cycloalkyl or a cyclic ether containing 1 ring oxygen atom and up to 5 ring carbon atoms with the proviso that $R_{16}$ and $R_{17}$ are not hydrogen simultaneously, and with the further proviso that when $R_5$ and $R_{17}$ are hydrogen, then $R_{16}$ is not ethoxy.

36. The compound according to claim 35 wherein lower alkyl and lower alkoxy groups contain 1-3 carbon atoms.

37. The compound according to claim 35 wherein lower alkyl is methyl.

38. The compound according to claim 35 wherein halogen is fluorine.

39. The compound according to claim 35 wherein $R_5$ is hydrogen or methyl.

40. The compound according to claim 35 wherein $R_{16}$ and $R_{17}$ are independently hydrogen, methoxy, trifluoromethyl, difluoromethyl, monofluoromethyl, hydroxy methyl, dimethylaminomethyl or carbomethoxy or $R_{15}$ and $R_{16}$ taken together with the carbon to which they are attached form a cyclopropyl or an oxirane ring.

41. The compound according to claim 1 having the formula:

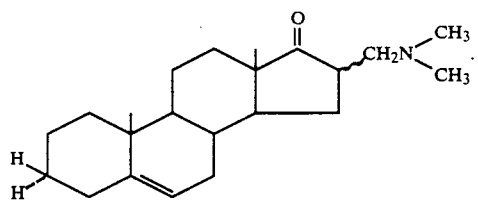

42. The compound according to claim 1 having the formula:

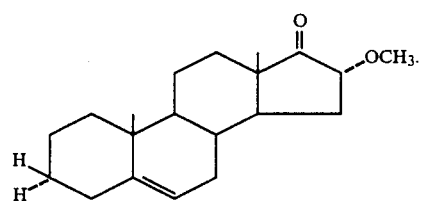

43. The compound according to claim 1 having the formula:

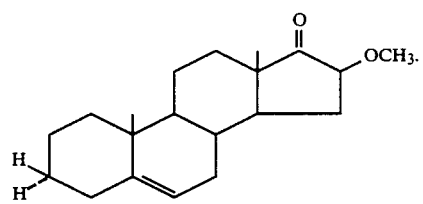

44. The compound according to claim 1 having the formula:

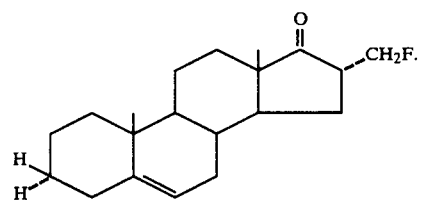

45. The compound according to claim 1 having the formula:

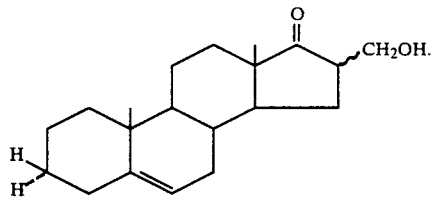

46. The compound according to claim 1 having the formula:

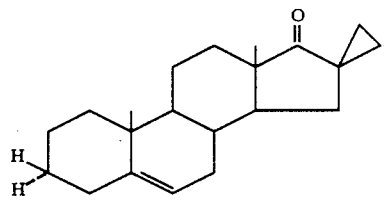

47. The compound according to claim 1 having the formula:

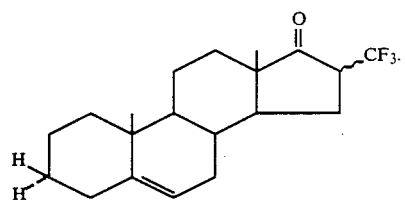

48. The compound according to claim 1 having the formula:

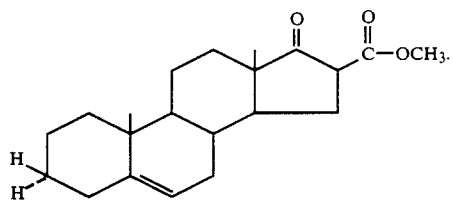

49. The compound according to claim 9 having the formula:

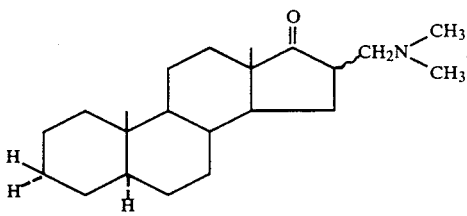

50. The compound according to claim 9 having the formula:

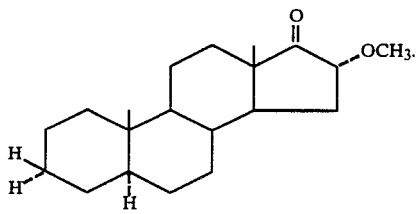

51. The compound according to claim 9 having the formula:

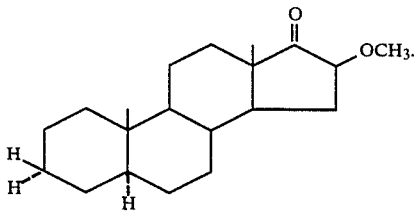

52. The compound according to claim 9 having the formula:

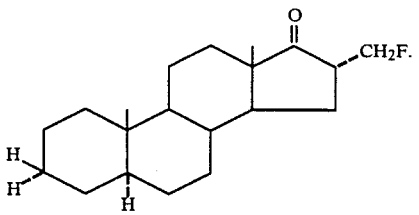

53. The compound according to claim 9 having the formula:

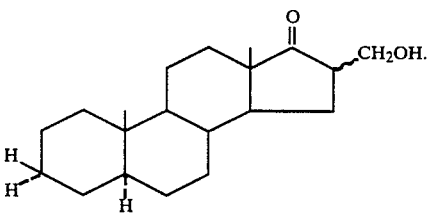

54. The compound according to claim 9 having the formula:

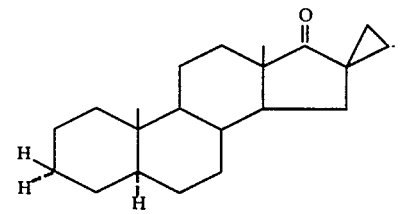

55. The compound according to claim 9 having the formula:

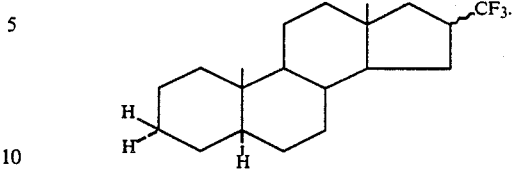

56. The compound according to claim 9 having the formula:

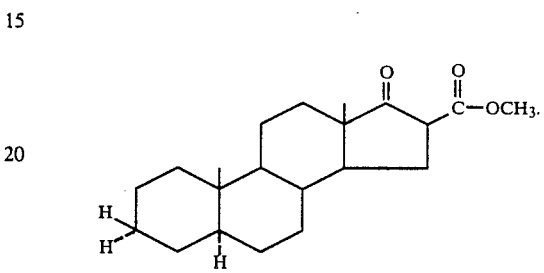

57. The compound according to claim 1 having the formula:

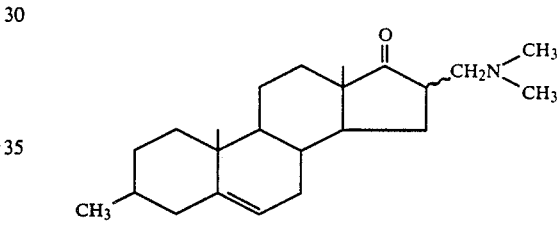

58. The compound according to claim 1 having the formula:

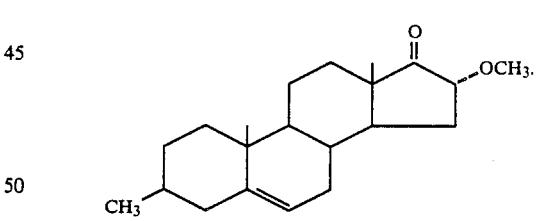

59. The compound according to claim 1 having the formula:

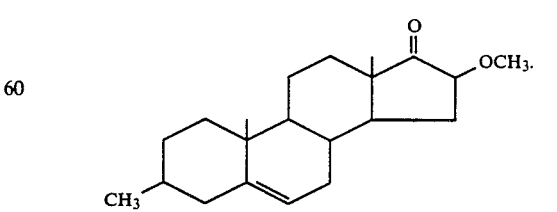

60. The compound according to claim 1 having the formula:

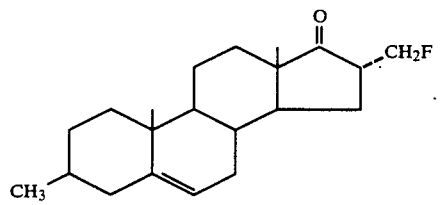

61. The compound according to claim 1 having the formula:

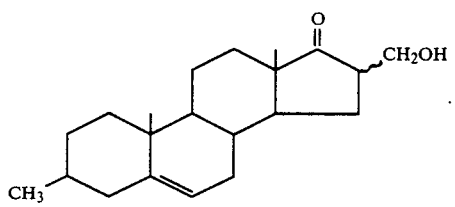

62. The compound according to claim 1 having the formula:

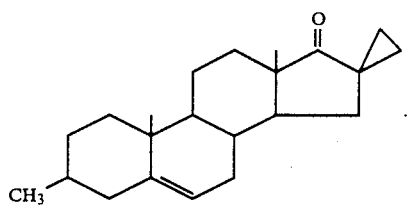

63. The compound according to claim 1 having the formula:

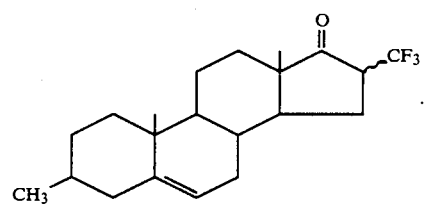

64. The compound according to claim 1 having the formula:

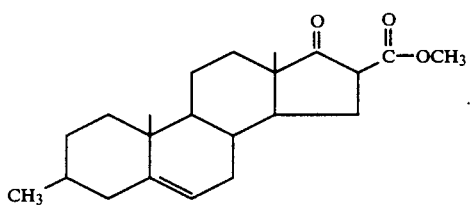

65. The compound according to claim 9 having the formula:

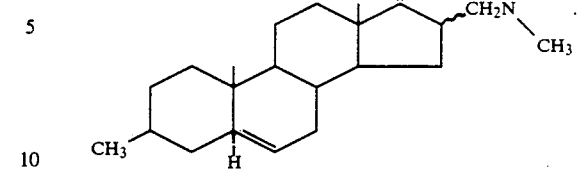

66. The compound according to claim 9 having the formula:

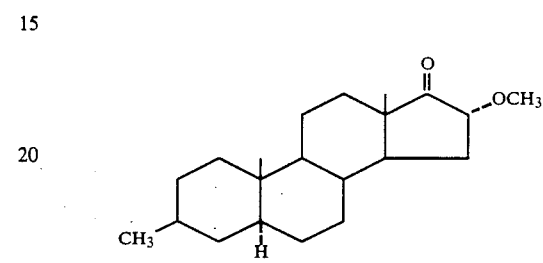

67. The compound according to claim 9 having the formula:

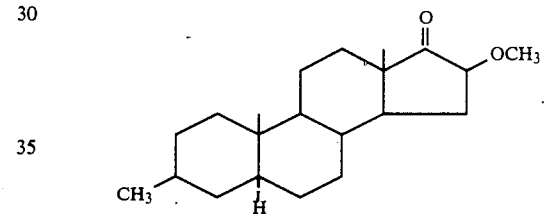

68. The compound according to claim 9 having the formula:

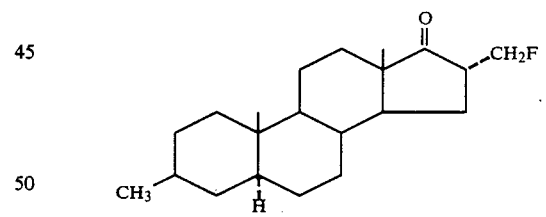

69. The compound according to claim 9 having the formula:

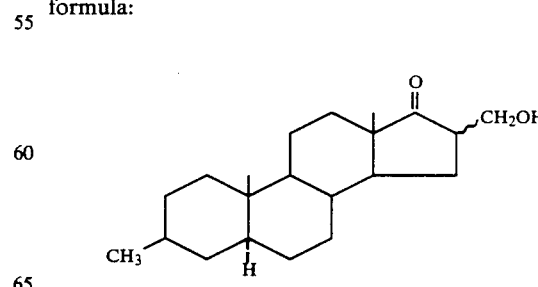

70. The compound according to claim 9 having the formula:

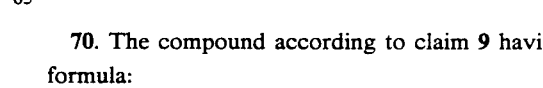

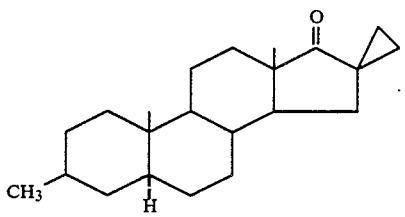

71. The compound according to claim 9 having the formula:

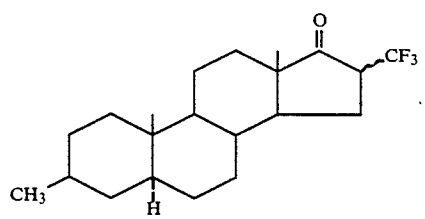

72. The compound according to claim 9 having the formula:

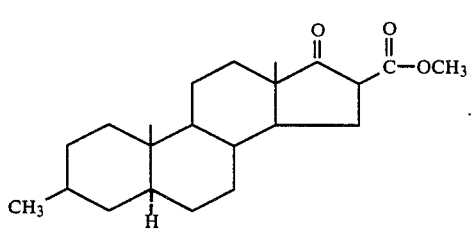

73. The compound according to claim 1 having the formula:

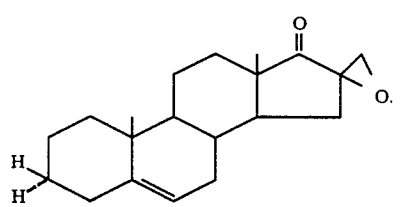

74. The compound according to claim 1 having the formula:

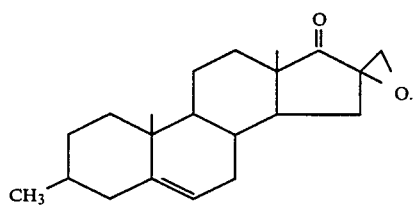

75. The compound according to claim 9 having the formula:

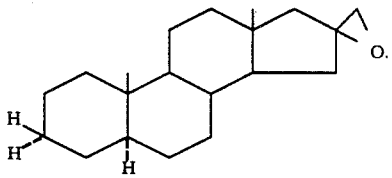

76. The compound according to claim 9 having the formula:

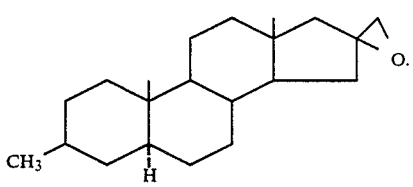

77. The compound according to claim 1 having the formula

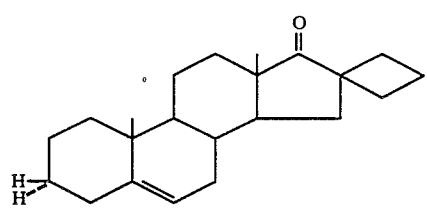

78. The compound according to claim 1 having the formula

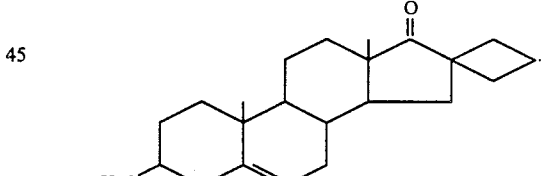

79. The compound according to claim 9 having the formula

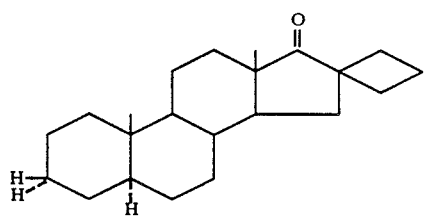

80. The compound according to claim 9 having the formula:

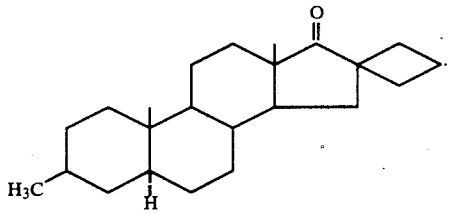

81. The compound according to claim 1 having the formula:

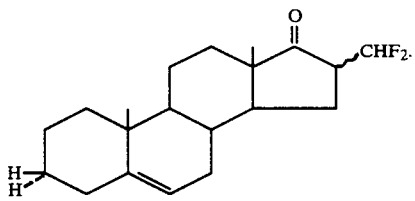

82. The compound according to claim 1 having the formula

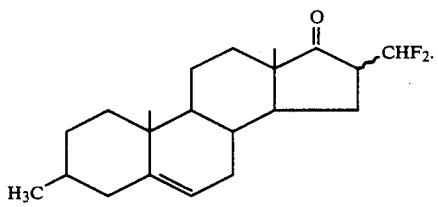

83. The compound according to claim 9 having the formula

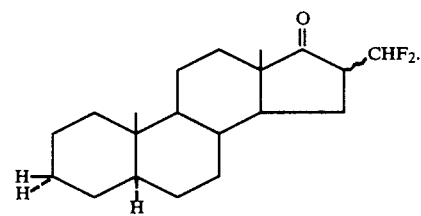

84. The compound according to claim 9 having the formula

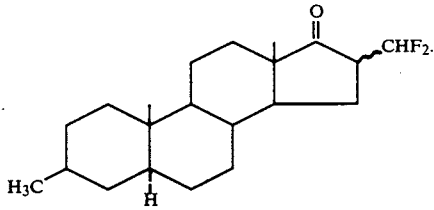

85. A pharmaceutical composition comprising a pharmaceutically effective amount of a compound according to claim 1 and a pharmaceutical carrier therefor.

86. A pharmaceutical composition comprising a pharmaceutically effective amount of a compound according to claim 9 and a pharmaceutical carrier therefor.

87. A process for the prophylaxis of cancer in a host, said process comprising administering to a host a cancer-prophylactically effective amount of a compound according to claim 1.

88. A process for the prophylaxis of cancer in a host, said process comprising administering to a host a cancer-prophylactically effective amount of a compound according to claim 9.

89. A process for the prophylaxis of hyperlipidemia in a host, said process comprising administering to a host an anti-hyperlipidemically effective amount of a compound according to claim 1.

90. A process for the prophylaxis of hyperlipidemia in a host, said process comprising administering to a host an anti-hyperlipidemically effective amount of a compound in accordance with claim 9.

91. A process for the prophylaxis of obesity in a host, said process comprising administering to a host an anti-obesity effective amount of a compound according to claim 1.

92. A process for the prophylaxis of obesity in a host, said process comprising administering to a host an anti-obesity effective amount of a compound according to claim 9.

93. A process for the treatment of diabetes in a host said process comprising administering to a host an anti-diabetic effective amount of a compound according to claim 1.

94. A process for the treatment of diabetes in a host said process comprising administering to a host an anti-diabetic effective amount of a compound according to claim 9.

95. A process for the prophylaxis of auto-immune disease in a host, said process comprising administering to a host an auto-immune prophylatically effective amount of a compound according to claim 1.

96. The process according to claim 95 wherein said disease is lupus erythematosis.

97. A process for the prophylaxis of auto-immune disease in a host, said process comprising administering to a host an auto-immune prophylatically effective amount of a compound according to claim 9.

98. The process according to claim 95 wherein said disease is lupus erythematosis.

99. A process for the treatment of cancer in a host, which process comprises administering to said host an anti-cancer effective amount of a compound according to claim 1.

100. A process for the treatment of cancer in a host, which process comprises administering to said host an anti-cancer effective amount of a compound according to claim 9.

* * * * *

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

Page 1 of 11

It is certified that error appears in the above-indentified patent and that said Letters Patent is hereby corrected as shown below:

Column 9, line 5: "J. W. Green" should read --T. W. Green--

Column 10, line 35: "interchaging" should read --interchanging--

Column 12, line 59: "knonw" should read --known--

Column 13, lines 32-55:

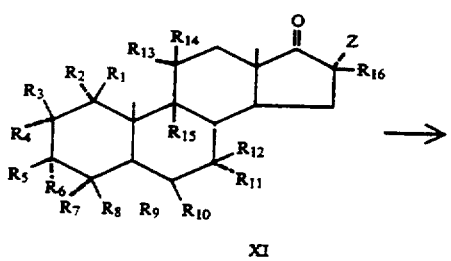 → 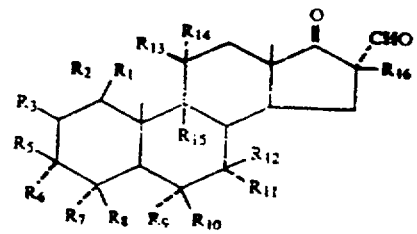

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

should read

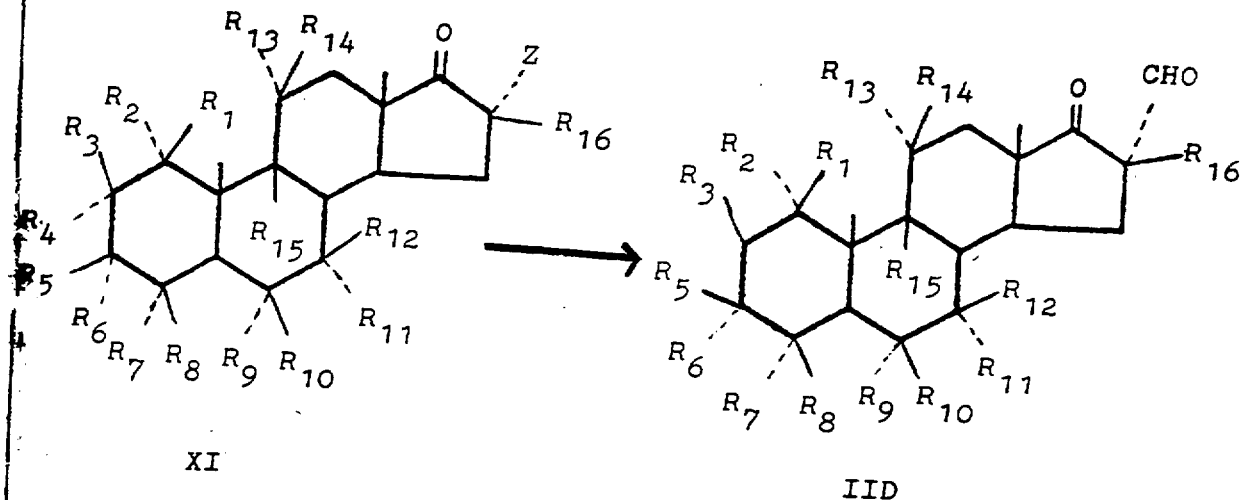

Column 18, line 42: "spiro pyrazoline" should read --spiro-pyrazoline--

Column 18, line 44: "16 spirocyclopropyl" should read --16-spiro-cyclopropyl--

Column 19, line 54: "3 a" should read --3a--

UNITED STATES PATENT AND TRADEMARK OFFICE
CERTIFICATE OF CORRECTION

PATENT NO.  : 5,001,119
DATED       : March 19, 1991
INVENTOR(S) : Arthur Schwartz, et al.

Page 3 of 11

It is certified that error appears in the above-indentified patent and that said Letters Patent is hereby corrected as shown below:

Column 22, line 67: "2methyl" should read --2-methyl--

Column 22, line 68: "3 H-18" should read --3, H-18--

Column 27, lines 55-65:

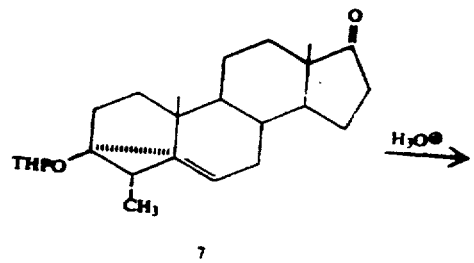

should read

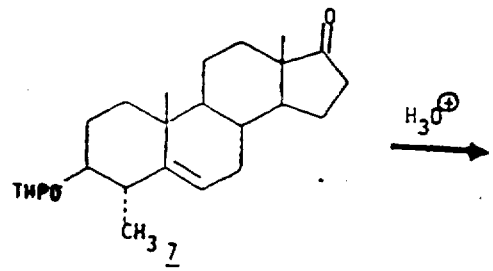

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 28, lines 40-55:

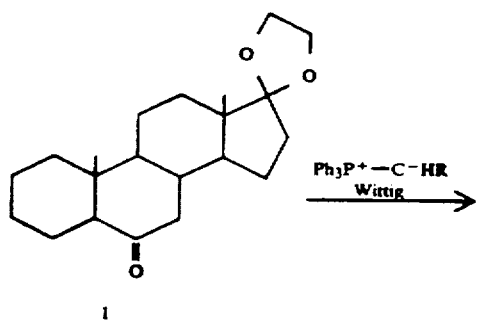

should read

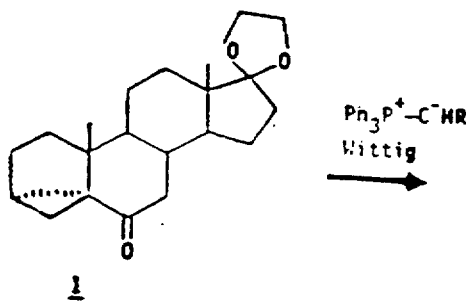

UNITED STATES PATENT AND TRADEMARK OFFICE
CERTIFICATE OF CORRECTION

PATENT NO.  :  5,001,119
DATED       :  March 19, 1991
INVENTOR(S) :  Arthur Schwartz, et al.

It is certified that error appears in the above-indentified patent and that said Letters Patent is hereby corrected as shown below:

Column 37, lines 1-10:

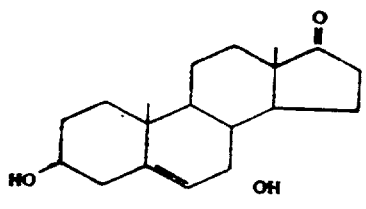

should read

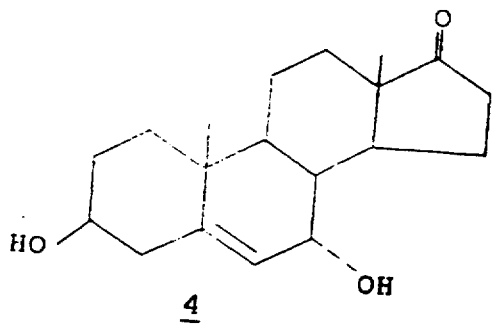

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 39, lines 15-22:

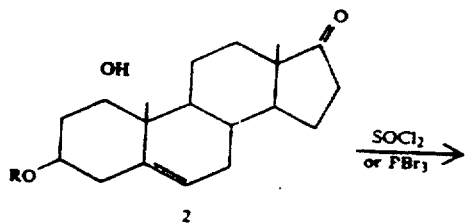

should read

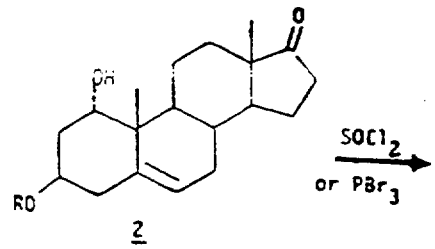

Column 43, line 6: "6-fuloro-3" should read --6-fluoro-3--

Column 47, line 38: "C-16αiodide" should read --C-16α-iodide--

UNITED STATES PATENT AND TRADEMARK OFFICE
CERTIFICATE OF CORRECTION

Page 7 of 11

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 50, line 68: "spiropyrazoline" should read --spiro-pyrazoline--

Column 53, lines 40-48:

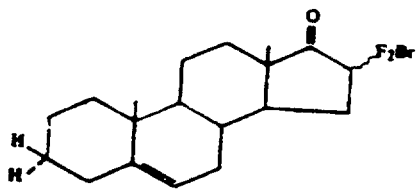

should read

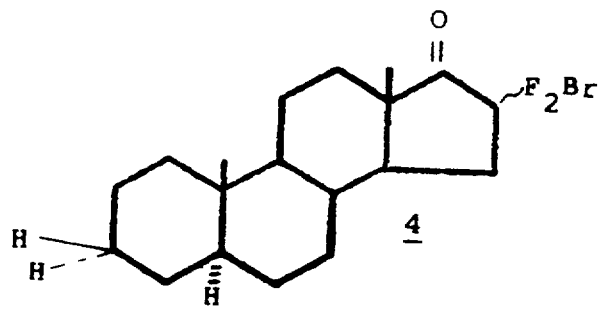

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 53, lines 50-59: delete the following:

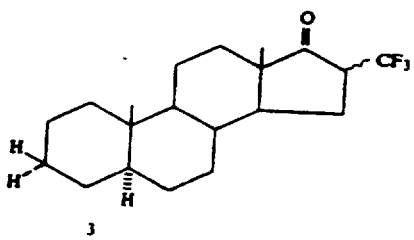

Column 55, line 8: "16 ξ difluoromethyl" should read --16 ξ-difluoromethyl--

Column 55, line 23: "disolved" should read --dissolved--

Column 58, line 48: "couterparts" should read --counterparts--

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 61, lines 1-10:

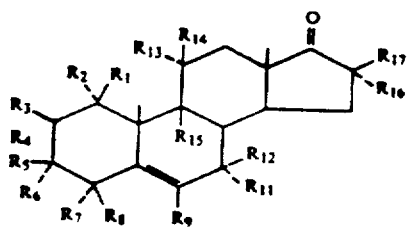

should read

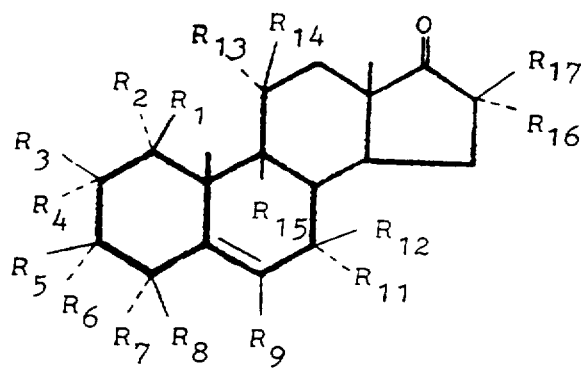

UNITED STATES PATENT AND TRADEMARK OFFICE
CERTIFICATE OF CORRECTION

PATENT NO.   :   5,001,119
DATED        :   March 19, 1991
INVENTOR(S)  :   Arthur Schwartz, et al.

It is certified that error appears in the above-indentified patent and that said Letters Patent is hereby corrected as shown below:

Column 61, lines 55-63:

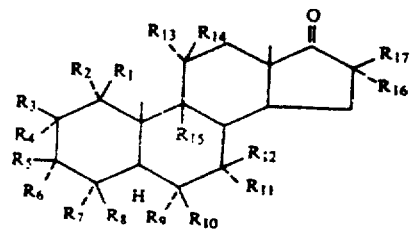

should read

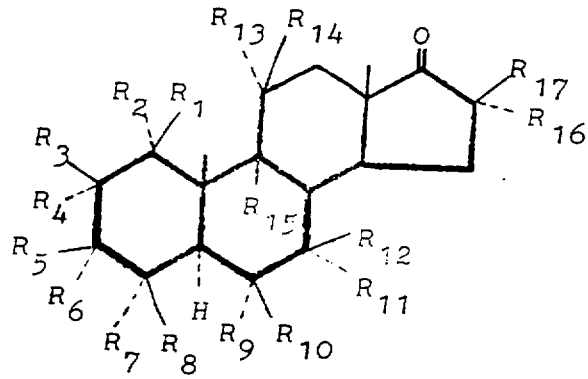

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

Column 70, lines 1-10:

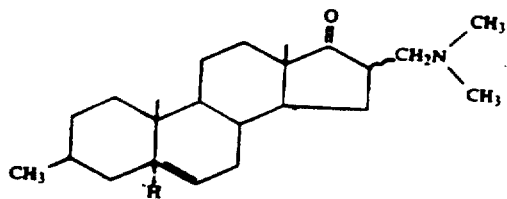

should read

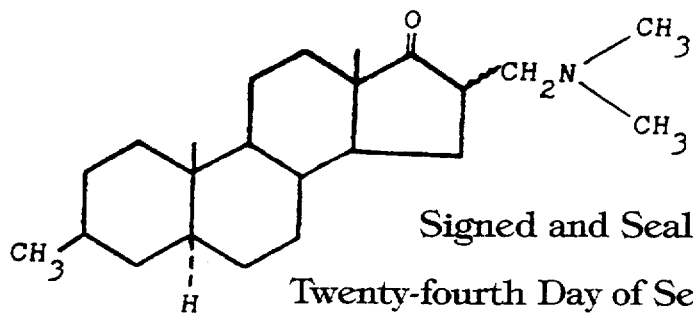

Signed and Sealed this

Twenty-fourth Day of September, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,001,119
DATED : March 19, 1991
INVENTOR(S) : Arthur Schwartz, et al.

It is certified that error appears in the above-indentified patent and that said Letters Patent is hereby corrected as shown below:

```
     Column 62, line 5:  "loweralkyl, aminoloweralkyl
should read --lower alkylamino loweralkyl--;
     Column 62, line 55: "loweralkyl aminoloweralkyl"
should read --lower alkyl amino lower alkyl--;
     Column 63, line 34: "loweralkyl, aminoloweralkyl"
should read --lower alkyl amino loweralkyl--;
     Column 64, line 16: "loweralkyl, aminoloweralkyl"
should read--loweralkylamino loweralkyl--;
     Column 64, line 59: "loweralkyl, aminoloweralkyl
should read -- loweralkylamino lower alkyl--;
```

Signed and Sealed this

Sixth Day of May, 1997

*Attest:*

BRUCE LEHMAN

*Attesting Officer*      *Commissioner of Patents and Trademarks*